(12) United States Patent
Willey

(10) Patent No.: US 7,476,502 B2
(45) Date of Patent: Jan. 13, 2009

(54) METHODS AND COMPOSITIONS FOR ASSAYING ANALYTES

(76) Inventor: James C. Willey, 4235 Deepwood La., Toledo, OH (US) 43614

(*) Notice: Subject to any disclaimer, the term of this patent is extended or adjusted under 35 U.S.C. 154(b) by 226 days.

(21) Appl. No.: 11/103,397

(22) Filed: Apr. 11, 2005

(65) Prior Publication Data

US 2005/0239116 A1 Oct. 27, 2005

Related U.S. Application Data

(60) Provisional application No. 60/561,841, filed on Apr. 12, 2004.

(51) Int. Cl.
 *C12Q 1/68* (2006.01)
 *C12P 19/34* (2006.01)

(52) U.S. Cl. .......................... 435/6; 435/91.2

(58) Field of Classification Search ................. None
See application file for complete search history.

(56) References Cited

U.S. PATENT DOCUMENTS

| | | | |
|---|---|---|---|
| 5,496,699 A | 3/1996 | Sorenson | |
| 5,639,606 A | 6/1997 | Willey | |
| 5,643,765 A | 7/1997 | Willey | |
| 5,712,125 A | 1/1998 | Uhlen | |
| 5,747,251 A | 5/1998 | Carson et al. | |
| 5,876,978 A | 3/1999 | Willey et al. | |
| 5,888,740 A | 3/1999 | Han | |
| 6,027,889 A | 2/2000 | Barany et al. | |
| 6,174,670 B1 | 1/2001 | Wittwer et al. | |
| 6,197,520 B1 | 3/2001 | Wittwer et al. | |
| 6,235,504 B1 | 5/2001 | Zhang et al. | |
| 6,245,514 B1 | 6/2001 | Wittwer et al. | |
| 6,268,148 B1 | 7/2001 | Barany et al. | |
| 6,355,431 B1 | 3/2002 | Chee et al. | |
| 6,534,269 B2 | 3/2003 | Liu et al. | |
| 2002/0132244 A1 | 9/2002 | Li-Sucholeiki | |
| 2003/0077611 A1 | 4/2003 | Slepnev | |
| 2003/0082616 A1 | 5/2003 | Tomita et al. | |
| 2003/0092051 A1 | 5/2003 | Liu et al. | |
| 2003/0143584 A1 | 7/2003 | Li-Sucholeiki | |
| 2003/0148335 A1 | 8/2003 | Shen et al. | |
| 2003/0207295 A1 | 11/2003 | Gunderson et al. | |
| 2003/0211489 A1 | 11/2003 | Shen et al. | |
| 2003/0215821 A1 | 11/2003 | Gunderson et al. | |
| 2004/0018491 A1 | 1/2004 | Gunderson et al. | |
| 2004/0081993 A1 | 4/2004 | Cantor et al. | |
| 2006/0194216 A1 | 8/2006 | Willey et al. | |

FOREIGN PATENT DOCUMENTS

| EP | 1092782 | | 4/2001 |
|---|---|---|---|
| EP | 1179600 | | 2/2002 |
| EP | 1270738 | A1 | 1/2003 |
| WO | WO 93/15229 | A2 | 8/1993 |
| WO | WO 94/09156 | | 4/1994 |
| WO | WO/94/23023 | | 10/1994 |
| WO | WO 93/15229 | A3 | 3/1995 |
| WO | WO 97/46707 | | 12/1997 |
| WO | WO 98/58083 | | 12/1998 |
| WO | WO 99/14376 | | 3/1999 |
| WO | WO 99/51773 | | 10/1999 |
| WO | WO 99/63109 | A1 | 12/1999 |
| WO | WO 00/40755 | | 7/2000 |
| WO | WO 00/63437 | | 10/2000 |
| WO | WO 01/14539 | | 3/2001 |
| WO | WO 01/16352 | | 3/2001 |
| WO | WO 01/55454 | | 8/2001 |
| WO | WO 01/62975 | | 8/2001 |
| WO | WO 01/84146 | A2 | 11/2001 |
| WO | WO 01/84146 | A3 | 4/2002 |
| WO | WO 03/006677 | | 1/2003 |
| WO | WO 03/035841 | | 5/2003 |
| WO | WO 04/001062 | | 12/2003 |
| WO | WO 2004/007755 | | 1/2004 |

OTHER PUBLICATIONS

Allen, et al. Enhanced insulin-like growth factor binding protein-related protein 2 (Connective tissue growth factor) expression in patients with idiopathic pulmonary fibrosis and pulmonary sarcoidosis. Am J Respir Cell Mol Biol. 1999; 21(6): 693-700.

Amabile, et al. Real-time quantification of different types of bcr-abl transcript in chronic myeloid leukemia. Haematologica. 2001; 86(3): 252-9.

Apostolakos, et al. Measurement of gene expression by multiplex competitive polymerase chain reaction. Anal Biochem. 1993; 213(2): 277-84.

Celi, et al. A rapid and versatile method to synthesize internal standards for competitive PCR. Nucleic Acids Res. 1993; 21(4): 1047.

Crawford, et al. Multiplex standardized RT-PCR for expression analysis of many genes in small samples. Biochem Biophys Res Commun. 2002; 293(1): 509-16.

Crawford, et al. Normal bronchial epithelial cell expression of glutathione transferase P1, glutathione transferase M3, and glutathione peroxidase is low in subjects with bronchogenic carcinoma. Cancer Res. 2000; 60(6): 1609-18.

Crawford, et al. Quantitative end-point RT-PCR expression measurement using the Agilent 2100 Bioanalyzer and standardized RT-PCR. Agilent Application. 2001; 1-8.

Crawford, et al. Reproducible gene expression measurement among multiple laboratories obtained in a blinded study using standardized RT (StaRT)-PCR. Mol Diagn. 2001; 6(4): 217-25.

Demuth, et al. The gene expression index c-myc×E2F-1/p21 is highly predictive of malignant phenotype in human bronchial epithelial cells. Am J Respir Cell Mol Biol. 1998; 19(1): 18-24.

(Continued)

*Primary Examiner*—James Martinell
(74) *Attorney, Agent, or Firm*—Wilson Sonsini Goodrich & Rosati

(57) ABSTRACT

The present invention is directed to methods and compositions for assaying one or more analytes in a sample with improved sensitivity, reproducibility and/or lower detection limits, as well as applications employing such compositions and methods. In particular, the present invention provides methods and compositions for assaying one or more non-nucleic acid analytes with one or more other nucleic acid and/or non-nucleic acid analytes that serve as controls.

25 Claims, 9 Drawing Sheets

(6 of 9 Drawing Sheet(s) Filed in Color)

OTHER PUBLICATIONS

Devereux, et al. A comprehensive set of sequence analysis programs for the VAX. Nucleic Acids Res. 1984; 12(1 Pt 1): 387-95.

Ding, et al. A high-throughput gene expression analysis technique using competitive PCR and matrix-assisted laser desorption ionization time-of-flight MS. Proc Natl Acad Sci USA. 2003; 100(6): 3059-64.

Giulietti, et al. An overview of real-time quantitative PCR: applications to quantify cytokine gene expression. Methods. 2001; 25(4): 386-401.

Hedenfalk, et al. Gene-expression profiles in hereditary breast cancer. N Engl J Med. 2001; 344(8): 539-48.

Lee, et al. Seven-color, homogeneous detection of six PCR products. Biotechniques. 1999; 27(2): 342-9.

Loitsch, et al. Reverse transcription-competitive multiplex PCR improves quantification of mRNA in clinical samples—application to the low abundance CFTR mRNA. Clin Chem. 1999; 45(5): 619-24.

Meijerink, et al. A novel method to compensate for different amplication efficiencies between patient DNA samples in quantitative real-time PCR. J Mol Diagn. 2001; 3(2): 55-61.

Meksem, et al. A high-resolution map of the vicinity of the RI locus on chromosome V of potato based on RFLP and AFLP markers. Mol Gen Genet. 1995; 249(1): 74-81.

Mollerup, et al. Sex differences in lung CYP1A1 expression and DNA adduct levels among lung cancer patients. Cancer Res. 1999; 59(14): 3317-20.

Ross, et al. Quantitative approach to single-nucleotide polymorphism analysis using MALDI-TOF mass spectrometry. Biotechniques. 2000; 29(3): 620-4, 626, 628-9.

Rots, et al. Circumvention of methotrexate resistance in childhood leukemia subtypes by rationally designed antifolates. Blood. 1999; 94(9): 3121-8.

Rots, et al. mRNA expression levels of methotrexate resistance-related proteins in childhood leukemia as determined by standardized competitive template-based RT-PCR method. Leukemia. 2000; 14(12): 2166-75.

Siebert, et al. PCR MIMICS: competitive DNA fragments for use as internal standards in quantitative PCR. Biotechniques. 1993; 14(2): 244-9.

Vondracek, et al. Transcript profiling of enzymes involved in detoxification of xenbiotics and reactive oxygen in human normal and simian virus 40 T antigen-immortalized oral keratinocytes. Int J Cancer. 2002; 99(6): 776-82.

Willey, et al. Expression measurement of many genes simultaneously by quantitative RT-PCR using standardized mixtures of competitive templates. Am J Respir Cell Mol Biol. 1998; 19(1): 6-17.

Willey, et al. Quantitative RT-PCR measurement of cytochromes p450 1A1, 1B1, and 2B7, microsomal epoxide hydrolase, and NADPH oxidoreductase expression in lung cells of smokers and nonsmokers. Am J Respir Cell Mol Biol. 1997; 17(1): 114-24.

Adler, et al. A real-time immuno-PCR assay for routine ultrasensitive quantification of proteins. Biochem Biophys Res Commun. Aug. 22, 2003;308(2):240-50.

Supplementary European Search Report dated May 14, 2008 for EP 05777370.7.

METHODS AND COMPOSITIONS FOR ASSAYING ANALYTES

RELATED APPLICATION

This application claims priority to provisional application U.S. Pat No. 60/561,841, filed Apr. 12, 2004, which is incorporated herein in its entirety.

GOVERNMENT INTERESTS

Certain embodiments of the present invention were made under Research Grant No. NCI 85147 and CA 91129 from the National Cancer Institute, who may have certain rights thereto.

STATEMENT AS TO FEDERALLY SPONSORED RESEARCH

This invention was made with the support of the United States government under Contract No. CA085147 by the National Cancer Institute.

BACKGROUND OF THE INVENTION

Immunoassays are important tools used in the detection of a large variety of antigens. Immuno-polymerase chain reaction (iPCR) combines the analyte specificity conferred by immunoassays with the signal amplification provided by PCR to detect low levels of antigens. Development of this method, however, has progressed somewhat slowly over the last 10 years.

The completion of the human genome and the mushrooming of proteomics bring increased interests in detecting and/or quantifying low analyte abundance. In particular, there remains a need for standardized protocol employing high affinity, stable reagents, as well as GLP-compatible laboratory methods for analyzing multiple different types of analytes.

The present invention provides methods and compositions directed to these and other needs. Other methods and compositions are provided in U.S. patent application Ser. No. 10/109,349, filed Mar. 28, 2002, and Ser. No. 10/471,473, filed Mar. 12, 2002, International Applications PCT/US03/09428, filed Mar. 27, 2003; and U.S. Provisional Application Ser. Nos. 60/368,288 and 60/368,409, filed Mar. 28, 2002; 60/550,279 filed Mar. 5, 2004; and 60/646,157, filed Jan. 21, 2005, each of which are herein incorporated by reference, as is U.S. Provisional Application Ser. No. 60/561,841, filed Apr. 12, 2004.

BRIEF DESCRIPTION OF THE INVENTION

One aspect of the instant invention relates to a method for assaying an analyte in a sample, comprising allowing the analyte to couple to a first nucleic acid; mixing the analyte with a known amount of an antagonist for the analyte wherein the antagonist is coupled to a competitive template for the first nucleic acid; exposing the mixture to a receptor that can form complexes with both the antagonist and the analyte; obtaining a first relation, the first relation comparing amplified product of the first nucleic acid that complexed with the receptor to co-amplified product of the competitive template for the first nucleic acid that complexed with the receptor; mixing a reference nucleic acid in the first sample with a known amount of a competitive template for the reference nucleic acid wherein the reference nucleic acid is a control for loading; obtaining a second relation, the second relation comparing amplified product of the reference nucleic acid to co-amplified product of the competitive template for the reference nucleic acid; and comparing the first and the second relations, thereby assaying the analyte.

In some embodiments, the antagonist comprises the analyte. In some embodiments, the receptor is immobilized on a substrate. In some embodiments, the reference nucleic acid comprises a sequence substantially identical to the first nucleic acid. In some embodiments, the method further comprises diluting the co-amplified products of the first nucleic acid and of the competitive template for the first nucleic acid; and further co-amplifying the diluted amplified products. In some embodiments, the allowing step follows the first mixing and/or the exposing step. In some embodiments, the receptor is a peptoid. In some embodiments, the analyte is coupled to the first nucleic acid via a peptoid and/or the antagonist is coupled to the competitive template for the first nucleic acid via a peptoid. In some embodiments, obtaining the first and the second relations does not involve taking real-time measurements. In some embodiments, at least one of the amplified products is obtained from beyond an exponential phase of amplification.

Some embodiments of the instant invention provide a method for assessing a first analyte in a sample, comprising allowing the first analyte to couple to a first nucleic acid; allowing a second analyte in the sample to couple to a second nucleic acid; mixing the first and the second analytes with known amounts of an antagonist for the first analyte coupled to a competitive template for the first nucleic acid and an antagonist for the second analyte coupled to a competitive template for the second nucleic acid; exposing the mixture to a first receptor that can form complexes with the antagonist for the first analyte and with the first analyte and to a second receptor that can form complexes with the antagonist for the second analyte and with the second analyte; obtaining a first relation, the first relation comparing amplified product of the first nucleic acid that complexed with the first receptor to co-amplified product of the competitive template for the first nucleic acid that complexed with the first receptor; obtaining a second relation, the second relation comparing amplified product of the second nucleic acid that complexed with the second receptor to co-amplified product of the competitive template for the second nucleic acid that complexed with the second receptor; and comparing the first and the second relations; thereby assessing an amount of the first analyte.

In some embodiments, the second analyte serves as a reference analyte to control for loading. In some embodiments, the reference analyte is alpha-fetoprotein. In some embodiments, the known amounts of the antagonists are provided in a standardized mixture, e.g., where the antagonist for the first analyte is at a known concentration relative to the antagonist for the second analyte in the standardized mixture. In some embodiments, the antagonist for the first analyte is at a series of known concentrations relative to the antagonist for the second analyte in a series of the standardized mixtures. In some embodiments, the first receptor or the second receptor is immobilized on a substrate. In some embodiments, at least one of the amplified products is obtained from beyond an exponential phase of the amplification. In some embodiments, the method can enumerate less than about 100 molecules of the first analyte in the sample. In some embodiments, the method can enumerate less than about 10 molecules of the first analyte in the sample. In some embodiments, at least one step is computer implemented. In some embodiments, the assessed amount is provided as a numerical value that indicates a biological state. In some embodiments, the assessed amount is used to provide a numerical index that indicates a biological state.

Some embodiments of the instant invention provide a method for assessing an analyte in a sample, comprising allowing the analyte to couple to a first nucleic acid; mixing the analyte with a known amount of an antagonist for the analyte wherein the antagonist is coupled to a competitive template for the first nucleic acid; exposing the mixture to a receptor that can form complexes with both the antagonist and the analyte; co-amplifying the first nucleic acid that complexed with the receptor and the competitive template for the first nucleic acid that complexed with the receptor; and obtaining a relation wherein the relation is substantially constant beyond an exponential phase of the co-amplification; thereby assessing an amount of the analyte.

In some embodiments, obtaining the substantially constant relation comprises obtaining a first relation, the first relation comparing amplified product of the first nucleic acid that complexed with the receptor to co-amplified product of the competitive template for the first nucleic acid that complexed with the receptor; obtaining a second relation, the second relation comparing amplified product of a reference nucleic acid to co-amplified product of a competitive template for the reference nucleic acid; and comparing the first and the second relations.

Another aspect of the instant invention relates to compositions for assaying analytes, methods of preparing such compositions and kits comprising one or more of such compositions. In some embodiments, a kit is provided comprising a standardized mixture of reagents, the reagents comprising an antagonist for a first analyte in a sample, the antagonist for the first analyte being coupled to a competitive template for a first nucleic acid; and a competitive template for a second analyte in the sample, the second analyte comprising a nucleic acid, wherein the standardized mixture allows direct comparison between amounts of the first analyte in the sample and in at least about 4 other samples with a coefficient of variation of less than about 20%, each of the 5 samples comprising less than about 100 molecules of the first analyte. In some embodiments, a kit is provided comprising a standardized mixture of reagents, the reagents comprising an antagonist for a first analyte in a sample, the antagonist for the first analyte being coupled to a competitive template for a first nucleic acid; and an antagonist for a second analyte in the sample, the antagonist for the second analyte being coupled to a competitive template for a second nucleic acid, wherein the standardized mixture allows direct comparison between amounts of the first analyte in the sample and in at least about 4 other samples with a coefficient of variation of less than about 20%, each of the 5 samples comprising less than about 100 molecules of the first analyte.

In some kit embodiments, the coefficient of variation is less than about 10%. In some kit embodiments, the coefficient of variation is less than about 5%. In some embodiments, the kits further comprise a first receptor that can form complexes with both the first analyte and the antagonist for the first analyte. In some embodiments, the kits further comprise a second receptor that can form complexes with both the second analyte and the antagonist for the second analyte. In some embodiments, the kits further comprise a substrate for immobilizing the complexes. In some embodiments, the kits further comprise the first nucleic acid wherein the first nucleic acid is coupled to a ligand for coupling to the first analyte. In some embodiments, the kits further comprise the second nucleic acid wherein the second nucleic acid is coupled to a ligand for coupling to the second analyte.

In some kit embodiments, the antagonist for the first analyte is at a known concentration relative to the competitive template for the second analyte. In some kit embodiments, the antagonist for the first analyte is at a series of known concentrations relative to the competitive template for the second analyte. In some kit embodiments, the antagonist for the first analyte is at a known concentration relative to the antagonist for the second analyte. In some kit embodiments, the antagonist for the first analyte is at a series of known concentrations relative to the antagonist for the second analyte.

In some kit embodiments, the first analyte comprises a microbe and the second analyte comprises a nucleic acid corresponding to a gene indicating viability of the microbe. In some kit embodiments, the first analyte comprises a microbe and the second analyte comprises a nucleic acid corresponding to a gene indicating a host response to the microbe. In some kit embodiments, first analyte comprises a microbe and the second analyte comprises a nucleic acid corresponding to a gene indicating a host response to a treatment of the microbe. In some kit embodiments, first analyte comprises a drug and the second analyte comprises a nucleic acid corresponding to a gene indicating a response to the drug. In some kit embodiments, the first and the second analytes comprise biological and/or chemical warfare agents. In some kit embodiments, the first analyte comprises a biological and/or chemical warfare agent and the second analyte comprises a nucleic acid corresponding to a gene indicating a response to of the agent.

In some kit embodiments, the standardized mixture comprises sufficient reagents for assessing amounts of the first analyte in more than about $10^6$ samples. In some kit embodiments, the standardized mixture comprises sufficient reagents for assessing amounts of the first analyte in more than about $10^8$ samples. In some kit embodiments, the reagents further comprise antagonists for at least about 2 additional analytes in the first sample wherein the antagonists are coupled to competitive templates for at least about 2 additional nucleic acids. In some kit embodiments, the reagents further comprise antagonists for at least about 50 additional analytes in the first sample wherein the antagonists are coupled to competitive templates for at least about 50 additional nucleic acids.

Another aspect of the instant invention relates to a database comprising numerical values, the numerical values corresponding to amounts of a non-nucleic acid analyte in a number of samples wherein the numerical values are directly comparable between about 5 of the samples with a coefficient of variation of less than about 20%, each of the 5 samples comprising less than about 100 molecules of the non-nucleic acid analyte. Another aspect of the instant invention relates to a database comprising numerical indices, the numerical indices obtained by mathematical computation of 2 numerical values, the 2 numerical values corresponding to amounts of a non-nucleic acid analyte and another analyte in a number of samples wherein the numerical values are directly comparable between about 5 of the samples with a coefficient of variation of less than about 20%, each of the 5 samples comprising less than about 100 molecules of the non-nucleic acid analyte. In some database embodiments, the coefficient of variation is less than about 10%. In some database embodiments, the coefficient of variation is less than about 5%.

Other aspects of the instant invention relate to applications using one or more methods, compositions, kits, and/or database embodiments, e.g., in diagnosis, drug development, and/or detection of biological and/or chemical warfare agents.

BRIEF DESCRIPTION OF THE FIGURES

The file of this patent contains at least one drawing executed in color. Copies of this patent with color drawing(s) will be provided by the Patent and Trademark Office upon request and payment of necessary fee.

The novel features of the invention are set forth with particularity in the appended claims. A better understanding of the objects, features and advantages of the present invention will be obtained by reference to the following detailed description that sets forth illustrative embodiments, in which the principles of the invention are utilized, and the accompanying drawings of which:

Each of these figures provides an illustration only, and is in no way intended to be limiting with respect to the present invention. For example, those skilled in the art will readily appreciate variations and modifications of the schemes illustrated based on the teachings provided herein.

DETAILED DESCRIPTION OF THE INVENTION

The present invention is directed to methods and compositions for assaying analytes, including non-nucleic acid analytes, methods of preparing such compositions, and applications employing such compositions and methods.

I. Methods for Assaying Analytes

One aspect of the present invention relates to methods for assaying one or more analytes in a sample. Analytes can comprise nucleic acid and/or non-nucleic acid analytes, including any antigen. In some embodiments, methods of the instant invention comprise the use of endogenous and/or exogenous standards with various types of immunoassays to improve sensitivity, reproducibility, and/or accuracy, lowering detection limits and/or reducing coefficients of variation for analyte measurements. Nucleic acid analytes can be co-amplified with known amounts of corresponding competitive templates. Non-nucleic acid analytes can be coupled to nucleic acid tags and the tags can be co-amplified with known amounts of corresponding competitive templates. Further comparing relative amounts of amplified products for two or more analytes can allow robust, quality-controlled, standardized assays for quantifying multiple analytes in a sample. Such assays find use in diagnostics and research, e.g., by facilitating early diagnosis or detailed bioavailability studies, as well as in military defense, e.g., by detecting minute amounts of agents of biological and/or chemical warfare.

A. Immunoassays

Figure 1:
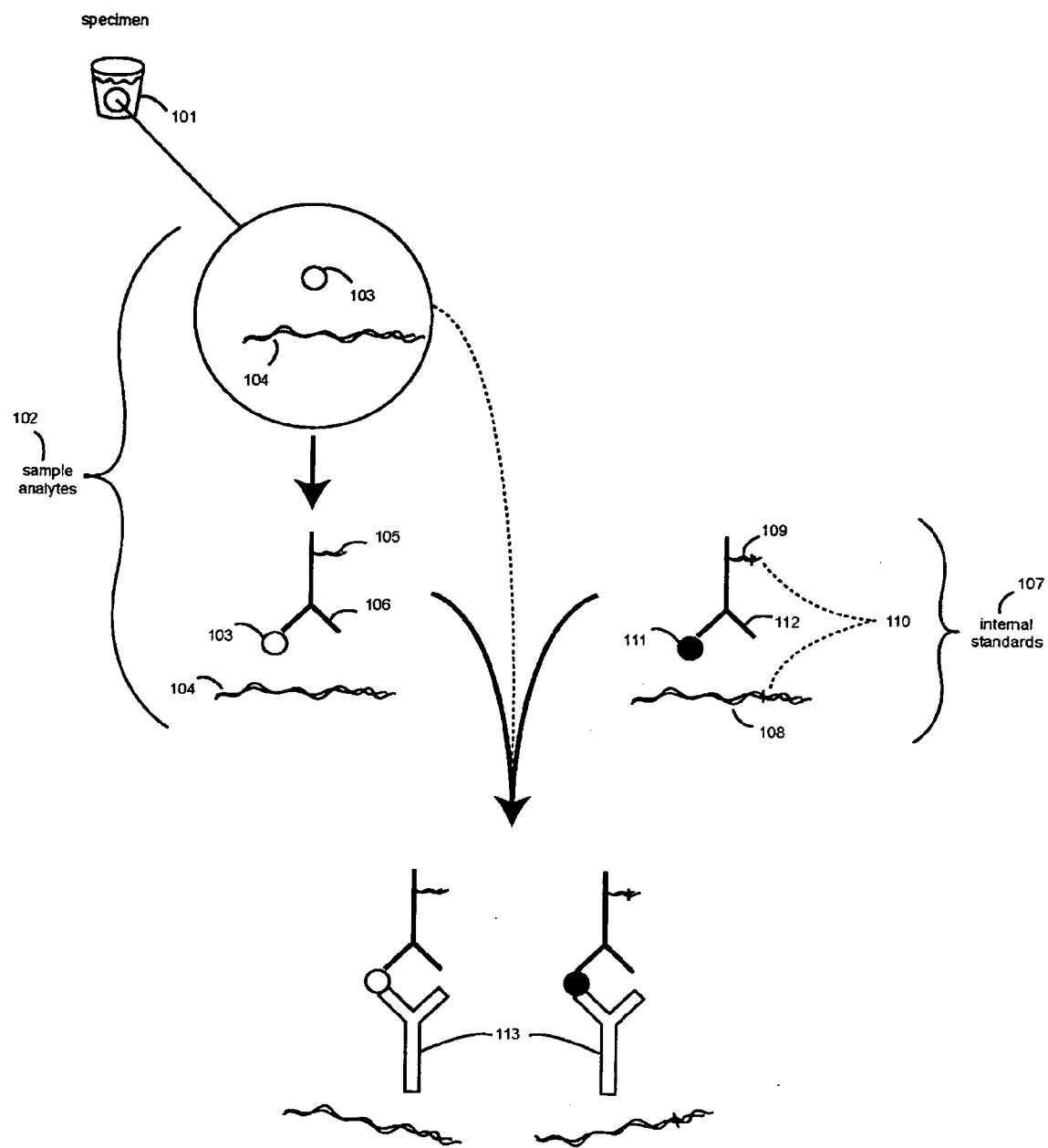
FIG. 1 illustrates an overall process for assaying analytes in some embodiments of the present invention.

FIG. 1 illustrates an overall process for assaying analytes in some embodiments of the present invention. In some embodiments, assaying refers to assessing, evaluating and/or measuring an analyte, e.g., to provide a measure of the amount of an analyte in a specimen and/or sample. In some embodiments, assaying refers to detecting a presence or absence of the analyte of interest. In some embodiments, assaying refers to quantifying an amount of an analyte, e.g., providing a measure of concentration or degree of analyte abundance. For example, quantifying an amount may comprise obtaining an index, percentage, relation, visual or other value indicative of the level of analyte in a sample. Assaying may be direct or indirect, e.g., the chemical species detected and/or quantified need not be the analyte molecule itself, but may be for example, a derivative thereof or a species corresponding thereto. In some embodiments, assaying refers to enumerating the number of molecules of analyte present in a sample and/or specimen, e.g., to determine an antigen copy number. In preferred embodiments, the invention allows quantification of small amounts of an analyte, for example, where the analyte is present in low amounts in a sample, where only small amounts of the analyte remain intact and/or where only small amounts of a specimen are provided.

As FIG. 1 illustrates, a specimen 101 is obtained comprising sample analytes 102 to be assayed. "Specimen" as used herein can refer to material collected for analysis, e.g., a swab of culture, a pinch of tissue, a biopsy extraction, or a vial of a biological fluid. Tissue can include, e.g., organs, tumors, lymph nodes, arteries, aggregates of cells and/or individual cells. Biological fluids can include, e.g., saliva, tears, mucus, lymph fluids, sputum, stool, pleural fluid, pericardial fluid, lung aspirates, exudates, peritoneal fluid, plasma, blood, serum, white blood cells, cerebral spinal fluid, synovial fluid, amniotic fluid, milk, semen, urine, and the like, as well as cell suspensions, cell cultures, or cell culture supernatants. A specimen may be taken for research, diagnostic or other purposes from any biological entity or other source, e.g., sources suspected of being contaminated. "Biological entity" as used herein can refer to any entity, including any species, e.g., a virus, bacterium, fungus or other pathogen, a cell, a tissue, an in vitro culture, a plant, an animal, a human patient, and/or a subject participating in a clinical trial. Sources can include, e.g., soil,crop materials, aerosols, water supplies, food or ingredients for consumption, microbial habitats and the like, including materials of environmental, industrial, medical, military, nutritional, and/or veterinary significance.

"Sample" as used herein can refer to specimen material used for a given assay, reaction, run, trial, and/or experiment. For example, a sample may comprise an aliquot of the specimen material collected, up to and including all of the specimen. Samples may be crude samples or processed samples, e.g., obtained after various processing or preparation steps carried out on the original specimen. For example, various cell separation methods, e.g., magnetically activated cell sorting, may be applied to separate or enrich analytes of interest in a biological fluid, such as blood. A sample may also comprise a dilution of a specimen, e.g., diluted serum or dilutions of other complex and/or protein-rich mixtures. For example, in some embodiments, a specimen may be serially diluted to provide a number of serially-diluted samples for analysis. As used herein the terms assay, reaction, run, trial and/or experiment can be used interchangeably. Preferred embodiments of the present invention can be practiced using small starting amounts of analytes to yield quantifiable results.

As FIG. 1 illustrates, sample analytes 102 can comprise non-nucleic acid analytes 103 and/or nucleic acid analytes 104. A non-nucleic acid analyte can refer to any moiety at least a portion of which comprises other than nucleic acid material. Non-nucleic acid analytes, include, e.g., small molecules, drugs or pharmaceuticals, toxins, metabolites, steroids, enzymes, hormones, proteins, peptides, glycoproteins, domains or motifs, amino acids, lectins, lipids, carbohydrates, sugars, polymers, tissues, cells, cell surface components, cellular components, subcellular organelles, whole or parts of microbes (such as pathogens, parasites, viruses, bacteria, fungi, and the like), biological and chemical warfare agents, or any combinations thereof. Non-nucleic acid analytes preferably include any antigen or any antigen-like moiety for which an antibody can be prepared, including nucleic acids in some cases, and including haptens.

A nucleic acid analyte can refer to any moiety at least a portion of which comprises nucleic acid material. "Nucleic acid" as used herein can refer to a polymeric form of nucleotides and/or nucleotide-like molecules of any length. For example, a nucleic acid can comprise naturally occurring DNA, e.g., genomic DNA, RNA, e.g., mRNA, and/or can comprise a synthetic molecule, including but not limited to cDNA, or recombinant molecules or molecules generated in any manner, such as by chemical synthesis, reverse transcription, DNA replication or a combination of these generating methods. The linkage between the subunits can be provided by phosphates, phosphonates, phosphoramidates, phosphorothioates, or the like, or by nonphosphate groups as are known in the art, such as peptide-type linkages utilized in peptide nucleic acids (PNAs). The linking groups can be chiral or achiral. Nucleic acids can have any three-dimensional structure, encompassing single-stranded, double-stranded, and triple helical molecules that can be, e.g., DNA, RNA, or hybrid DNA/RNA molecules. In some embodiments the sample comprises RNA to be measured, e.g., mRNA expressed in a tissue culture. In some embodiments the sample comprises DNA to be measured, e.g., cDNA reverse transcribed from transcripts. In some embodiments, the nucleic acid analyte to be measured is provided in a heterogeneous mixture of other nucleic acid molecules and/or other non-nucleic acid analytes. A nucleotide-like molecule can refer to a structural moiety that can act substantially like a nucleotide, for example exhibiting base complementarity with one or more of the bases that occur in DNA or RNA and/or being capable of base-complementary incorporation.

The terms "polynucleotide," "polynucleotide molecule," "nucleic acid molecule," "polynucleotide sequence" and "nucleic acid sequence," can be used interchangeably with "nucleic acid" herein. The nucleic acid and/or non-nucleic acid analytes of interest may be referred to as target analytes. Where nucleic acid analytes are measured, assaying can determine amounts of transcripts, corresponding to the level of expression of a gene. As used herein, the term "gene" can refer to nucleic acid molecules comprising an open reading frame. In some embodiments, a nucleic acid analyte occurs in more than one allelic variation. Compositions and methods for measuring allelic frequency are provided in co-pending U.S. application, filed Mar. 4, 2005, and are incorporated herein by reference.

One or more of the analytes in a sample can serve as an endogenous standard or "reference analyte" for other analyte(s) being assayed. A "reference analyte," as used herein, can refer to any analyte present a sample that serves as a loading control for target analyte(s). A loading control can control for variations in transfer of target analyte at one more steps of the assay, including, e.g., from biological entity to specimen, from specimen to sample used for amplification, or from amplification reaction to electrophoresis gel, etc. The target analyte(s) can be "normalized" to the reference analyte. In some preferred embodiments, the reference analyte comprises an analyte that is not expected to vary (or to vary significantly) among specimen obtained.

In some embodiments, e.g., the reference analyte comprises a nucleic acid that is not expected to vary (or to vary significantly) among sources or biological entities from which specimen are colleted, preferably showing little or no response to certain stimuli. For example, mRNA from a constitutively transcribed gene may provide the reference analyte. In some embodiments, for example, known or potential housekeeping genes may provide the reference analyte, including but not limited to human, mouse and/or rat glyceraldehyde-3-phospate dehydrogenase (GAPD or GAPDH), β-actin, 28S RNA, 18S RNA, and/or other ribonuclear protein genes. Other housekeeping genes that have been used as standards in Northern analyses of gene expression may also be used. See, e.g., Devereux et al., *Nucleic Acids Res.* 12:387 (1984); Barbu et al., *Nucleic Acids Res.* 17:7115 (1989).

In some embodiments, the reference analyte comprises a non-nucleic acid analyte that is not expected to vary (or to vary significantly) among sources or biological entities from which specimen are collected, preferably showing little or no response to certain stimuli. For example, a protein product of a constitutively transcribed and expressed gene may provide the reference analyte, including proteins encoded by known or potential housekeeping genes, such as human, mouse and/or rat glyceraldehyde-3-phospate dehydrogenase (GAPD or GAPDH), β-actin, 28S RNA, 18S RNA, and/or other ribonuclear protein genes, as well as other housekeeping genes referred to above.

Many other genes can provide transcripts or protein products as reference analytes. The choice of reference analyte may depend on the types of specimen being collected, the tissues being assayed, and/or the biological states being studied. For example, where carcinoembryonic antigen is being assayed, α-fetoprotein (AFP) can serve as the reference analyte. As another example, β-actin varies little among different normal bronchial epithelial cell samples (see, e.g., Crawford et al., *Cancer Res.* 60, 1609-1618 (2000)). Target and reference non-nucleic acid analytes may be tagged to facilitate detection and/or amplification, as described below.

As FIG. 1 illustrates, non-nucleic acid analyte 103 can be allowed to couple to a nucleic acid 105. The nucleic acid can act like a tag or identifier, serving to identify the analyte to which it is (or was) coupled. Nucleic acids used as tags may be any polymeric form of nucleotides and/or nucleotide-like molecules of any length, as described above. In preferred embodiments, the nucleic acid tag can be distinguished from other tags used for other non-nucleic acid analytes in a sample, e.g. by length, nucleotide sequences, or any other distinguishing feature as described in more detail below. In preferred embodiments, the nucleic acid tag can serve as a template for synthesis of a complementary nucleic acid, e.g., by base-complementary incorporation of nucleotide units, e.g. to allow for amplification of the tag. For example, a tag can be designed to include a DNA and/or RNA promoter. Amplification of the tag that is (or was) coupled to a sample analyte allows for detection and/or quantification of lower amounts of the analyte.

Nucleic acid tags can be synthesized by any techniques known in the art, provided herein and/or as can be developed. In some embodiments, tags may be synthesized by conventional oligonucleotide chemistry techniques, e.g., where the nucleotide units may be naturally occurring (e.g. adenine, cytosine, guanine, thymine and uracil); and/or nucleotide analogs (e.g., inosine, xanthine, hypoxanthine, 1,2-diaminopurine and the like). In some embodiments, tags may be synthesized enzymatically, e.g., by nucleic acid replication. The template used for nucleic acid replication may be from naturally occurring DNA and RNA or derivatives thereof, or from chemically synthesized oligonucleotides with artificial nucleotide sequence or with a sequence homology to naturally occurring DNA and RNA. Nucleic acid replication may take place in vitro or in vivo, e.g. in *E coli*, yeast, insect cells, or a virus. Any of a number of nucleic acid replication processes can be employed in enzymatic synthesis of nucleic acid tags, e.g. PCR, LCR, in vitro transcription, T7 polymerase transcription, reverse transcription, and the like.

In preferred embodiments, DNA molecules are used as nucleic acid tags, more preferably double-stranded DNA, even more preferably double-stranded DNA comprising at least about 100 base pairs. For example, use of DNA may increase stability in some embodiments. Use of double-stranded DNA may also increase sensitivity of the nucleic acid tags in some embodiments. See, e.g., Sano et al., *Science* 258(5079), 120-122 (1992); Zhou et al., *Nucleic Acids Res.* 21(25), 6038-6039 (1993); Ruzicka et al., *Science* 260(5108), 698-699 (1993). Some embodiments use nucleic acid tags of at least about 40 base pairs, at least about 50 base pairs, at least about 55 base pairs, at least about 60 base pairs, at least about 100 base pairs, or at least about 150 base pairs. Some embodiments use nucleic acid tags of no more than about 200 base pairs, no more than about 250 base pairs, no more than about 300 base pairs, or no more than about 350 base pairs. In some embodiments, longer length fragments may provide increased amounts of amplified products, facilitating detection and/or quantification. Some embodiments, e.g., use nucleic acid tags of at least about 500 base pairs, at least about 1 kb, or at least about 1.1 kb. Some embodiments use nucleic acid tags of no more than about 1.2 kb, no more than about 1.3 kb, or no more than about 1.4 kb. The tags can be designed according to the methods of amplification and/or quantification to be used, and the amount of diversity of the analytes to be assayed.

An analyte can be coupled to its nucleic acid tag by any technique described herein, known in the art, or as can be developed. "Coupling" and its grammatical variations, as used herein, can refer to direct and/or indirect binding, linking, adhering, conjugating, or other attachment of an analyte to a nucleic acid. Coupling may include covalent bonding, non-covalent bonding, ionic bonding, electrostatic interactions, Hydrogen bonding, van der Waals forces, hydrophobic bonding, or a combination thereof. In preferred embodiments, an analyte is coupled to its nucleic acid tag via a ligand, where the ligand comprises any moiety capable of recognizing and preferentially complexing with the given analyte over other analytes in a sample under conditions used. In some embodiments, e.g., the ligand can comprise an antibody.

As FIG. 1 illustrates, analyte 103 can be coupled to its nucleic acid tag 105 via an antibody 106. Any antibody that recognizes and preferentially binds to the analyte can be conjugated to nucleic acid tag and allowed to couple to the analyte. The 3'-, 5'-, or any intervening-positions of the nucleic acid tag can be used for conjugating to the antibody or other ligand. The antibody used can comprise one or more types of immunoglobulins, such as IgA, IgD, IgE, IgG, and/or IgM, or any fragments and/or derivatives thereof. Exemplary antibodies include, e.g., polyclonal antibodies, monoclonal antibodies, single chain antibodies (ScFv), antibody fragments, Fab fragments, Fab' fragments, F(ab')$_2$ fragments, Fv fragments, CDR subunits, and/or diabodies.

Antibodies can be from various species, such as bird (e.g., chicken); mammal (e.g., sheep, goat, monkey, mouse, rabbit, human), reptile (e.g., snake), or any biological entity capable of generating an antibody. Antibodies may be found in a serum, raised in test animals, prepared from a hybridoma culture or ascites fluid, or may be derived from recombinant expression in vitro or in vivo, or may be prepared by any other technique known in the art, provided herein, or as can be developed. For example, antibodies may be constructed artificially, e.g. by chemical and/or enzymatic means. In some embodiments, antibodies comprise chimeric and/or hybrid structures, e.g., humanized and/or primatized antibodies, and/or other non-naturally occurring antibody forms. Other ligands that may be used may also be prepared by any of the techniques provided herein with respect to antibodies.

In some embodiments, the nucleic acid tag is indirectly coupled to an antibody or other ligand that recognizes and preferentially binds the analyte. For example, a nucleic acid tag may be conjugated to a secondary antibody which in turn recognizes an antibody that recognizes the analyte. In some embodiments, a nucleic acid tag may be attached to one member of a binding pair and the other member of the pair may be attached to the antibody or other ligand. For example, a protein A-streptavidin chimera can be used to conjugate biotinylated DNA to antibody. See, e.g., Sano et al., supra, (1992); Sano et al., *Biotechnology*, 9:1378 (1991); and Zhou et al. supra, (1993). In some embodiments, avidin can be used to conjugate biotinylated antibody to biothinylated DNA. See, e.g., Ruzicka et al., supra, (1993).

In some embodiments, the nucleic acid tag is directly conjugated to an antibody or other ligand that recognizes and preferentially binds the analyte. See, e.g., Joerger et al., *Clin. Chem.* 41, 1371-1377 (1995); Wu et al., *Letters in Applied Micro.* 32, 321-325 (2001); Hendrickson et al., *Nucleic Acids Res.* 23(3), 522-529 (1995); McKie et al., *J. Immunol. Methods* 261(1-2), 167-175 (2002); Jablonski et al., *Nucleic Acids Res.* 23(3): 522-529 (1995); Adler et al., *Biochem. Biophys. Res. Commun.* 300, 757-763 (2003). Where direct attachment is used, secondary antibodies may not be needed. For example, in some embodiments, the nucleic acid tag can be chemically cross-linked to an antibody. Such embodiments can provide advantages of reduced incubation times, decreased number of washes, and/or decreased handling time, with consequent reductions in contamination. Further, in some embodiments, one ore more techniques are used to improve or optimize conditions for conjugating antibodies to nucleic acid tags. For example, some embodiments use heterobifunctional cross-linkers coupled to the nucleic acid tags, e.g., 4-butanediol diglycidyl ether, carbodiimide, dithiobis succinimidyl propionate, a diisocyanate, glyoxal, glutaraldehyde, p-phenyl diisothiocyanate, IN-succinimidyl S-acetylthioacetate (SATA), succinimidyl 4-(N-maleimidomethyl)cyclohexane-1-carboxylate) (SMCC), and/or sulfosuccinimidyl 6-(4'-azido-2'nitro-phenylamino)-hexanoate. See, e.g, U.S. Pat. No. 5,324,650. In some embodiments, the composition and/or length of the crosslinker may facilitate amplification of the conjugated tag. Additional methods for attaching nucleic acids to antibodies or other ligands are provided in Hnatowich et al., *Nuclear Medicine Comm.* 17:66-75 (1996).

In some preferred embodiments, cross-linked antibody-DNA conjugates are used to provide stable, specific, and/or sensitive antigen recognition. e.g., enabling detection of less than about 100, less than about 60, less than about 30, less than about 10, or less than about 6 initial molecules of the conjugated DNA template following amplification. In some embodiments, one or more modified bases are incorporated into a nucleic acid tag to facilitate attachment. For example, modified base(s) can be introduced during chemical synthesis, or introduced by a primer that contains a modified base. For example, thiol or amino-modified base on either 5' or 3' end can be used to facilitate coupling of a nucleic acid tag to an antibody or other ligand by using different types of NHS-Esters-Maleimide crosslinkers, such as EMCS, GMBS, NBS, sulfo-SMCC, sulfo-MBS, SMPB, Sulfo-SMPB, Sulfo-GMBS, Sulfo-EMCS (Pierce, Rockford, Ill.). See also Hendrickson et al., supra, (1995) that describes the use of 5' amino-modified oligonucleotides for antibody-oligonucleotide conjugation. As another example, a biotin modified base on either 5' or 3' end of a nucleic acid tag can be used to facilitate attachment to a biotinylated antibody or other ligand.

In some embodiments, following conjugation, conjugates can be separated and/or purified from un-conjugated antibodies and nucleic acid materials. For example, the conjugated antibody can be purified by gel filtration and anion exchange chromatography.

In some embodiments, monoclonal antibodies cross-linked to nucleic acid tags can be used to couple one molecule of analyte to one copy of its nucleic acid tag in a fixed (or substantially fixed) ratio, e.g., of about 1:1 (about equimolar). In other embodiments, different types of couplings may provide different ratios, e.g., where more than one molecule of analyte is coupled to one copy of its nucleic acid tag or where more than one copy of the nucleic acid tag is coupled to a molecule of analyte. See e.g, Schweitzer et al., *Proc. Natl. Acad. Sci. USA* 97:10113-10119 (2000) that describes conjugating multiple oligonucleotides (3 on average) onto each antibody. Preferred embodiments provide a known and fixed (or substantially fixed) molar ratio of nucleic acid tag to analyte. Monoclonal antibodies as used herein can refer to homogenous (or substantially homogenous) populations of antibodies that recognize and preferentially bind a particular antigen, preferably a particular epitope on a particular antigen.

In some embodiments, polyclonal antibodies can be used. For example, in some embodiments, different polyclonal antibodies for a given analyte can be used, where the different polyclonal antibodies are each conjugated to a given nucleic acid tag. The different polyclonal antibodies can recognize and preferentially bind different epitopes of the same analyte, thereby tagging the analyte with the same (or substantially the same) tag. In some embodiments, two or more different monoclonal antibodies for a given analyte can be used, where the two or more monoclonal antibodies are each conjugated to a given nucleic acid tag. The two or more different monoclonal antibodies can recognize and preferentially bind to different epitopes of the same analyte, thereby tagging the analyte with the same (or substantially the same) tag.

In preferred embodiments, conjugating a nucleic acid to an antibody (or other ligand) does not interfere or does not substantially interfere with the ability of the antibody (or other ligand) to recognize and preferentially complex with an analyte. For example, avidity of an antibody for its antigen is not lost, or substantially not lost upon conjugate. In some embodiments, antibody-nucleic acid conjugates can be compared with the corresponding un-conjugated antibodies to assess whether or to what extent antigen recognition and/or binding is compromised. For example, in some embodiments, binding affinities of conjugated and un-conjugated antibodies can be compared using surface plasmon resonance (SPR) analysis. Further details, e.g., are provided in Example I. Similar SPR analyses can be conducted for other ligands used to couple nucleic acid tags to analytes.

In preferred embodiments, suitable conditions are used for allowing coupling to the analyte. For example a chemical and/or biochemical environment can be used to facilitate and/or promote recognition and/or preferential complexing between a conjugated antibody (or other ligand) and a given analyte. For example, pH change, ionic strength, temperature, and/or organic solvent can be used to change the stringency of the environment to promote preferential binding to an analyte. Tolerance to stringent conditions can vary depending on the nature of the analyte/antibody (or other ligand). In some embodiments, additional reagents may be provided to facilitate and/or promote specific recognition and/or binding, e.g., reagents to reduce non-specific binding. For example, conditions in conventional immunoassays for promoting binding between an antibody and its antigen can be used in some embodiments. For example, reagents that block non-specific binding can include detergents, e.g. NP40, Tween 20, Trixton X-100 and the like; proteins, e.g., albumin, animal serum, fat-free milk and the like; nucleic acid fragments, e.g., sperm DNA, yeast tRNA, synthetic oligonucleotides and the like. In some embodiments, buffering reagents may be used, e.g., phosphate buffered saline, Tris-buffers, and the like. In some embodiments, buffers are used that support a pH in the range about 6 to about 9, such as, e.g., about 10 to about 200 mM of HEPES-KOH, PBS, Tris-HCl, and the like; about 1 to about 1,000 mM of salts containing monovalent ions, such as KCl, NaCl, and the like; about 1 to about 20 mM of salts containing divalent cations such as $CaCl_2$, $Mn(OAc)_2$, $MgCl_2$, and the like; about 1 to about 20 mM of chelating agents, such as EDTA, EGTA and the like; optionally as well as proteinase inhibitors, e.g. leupeptin, PMSF, trypsin inhibitors, and the like; at well as other inhibitors to promote stability, e.g., hydrolysis inhibitors; phosphatase inhibitors, and/or calcium.

In still some embodiments, analytes may be coupled to nucleic acid tags via artificial ligands, such as peptoids. See, e.g., Naffin et al., *Chem. Bid.* 10(3):251-259 (2003); Alluri et al., *J. Am. Chem. Soc.* 125(46):13995-134004 (2003); Burkoth et al., *Chem. Bid.* 9(5):647-654 (2002); de Haan et al., *Bioorg. Med. Chem.* 10(6); 1939-1945 (2002). Peptoids as used herein can refer to N-substituted oligoglycines that recognize and preferentially bind to specific analytes, e.g., specific protein analytes. In still some embodiments, peptide and/or ribosome display libraries can be used to identify other ligands for recognizing and preferentially complexing with analytes. See, e.g., Prinz et al., *J. Immunol. Methods* 285, 1-14 (2004); Lesinki et al., *Vaccine* 19, 1717-1726 (2001); Grothaus et al., *Vaccine* 18, 1253-1263 (2000); Coeshott et al., *Vaccine* 22(19), 2396-2405 (2004); Westerink et al., *Int. Rev. Immunol.* 20(2):251-261 (2001). For example, natural and/or modified peptides, e.g., peptides evolved to bind analytes can be obtained. In preferred embodiments, the analyte is coupled to its nucleic acid tag in such a way as to allow recognition of the coupled analyte by a receptor, as discussed in more detail below.

After coupling, various techniques may be used to separate uncoupled nucleic acid from nucleic acid tags coupled to analytes. In some embodiments, for example, antibody-nucleic acid conjugates may be immobilized, and un-coupled analytes can be removed by a washing step. In some embodiments, the analytes may be immobilized, and un-coupled antibody-nucleic acid conjugates may be removed by a washing step. In some embodiments, e.g., analytes comprise cellular components immobilized in a biological structure, including e.g., a cell wall, plasma membrane, nuclear membrane, other subcellular organelle membrane, viral coat, microbial capsule, and/or extracellular matrix. For example, a cell surface component and/or transmembrane protein can be fixed in such structures. The immobilization may occur in fixed or living cells, e.g., in culture or cell suspension, membrane fractions, or sheep red blood cell cultures. In some embodiments, analytes comprise cellular components immobilized in fixed cells or tissue sections, e.g., in in situ and/or imunohistochemical approaches. See, e.g., Cao et al., *Lancet* 356(9234): 1002-1003 (2000). Cellular components can include, e.g., cytosol, cytoskeleton, endoplasmic reticulum, Golgi complexes, nucleus, mitochondria, and/or other cellular organelles.

Washing can comprise application of a stringent solution, e.g. to remove non-specifically bound materials. For example, the wash solution can provide chemical and/or biochemical environments as described above, preferably adjusted to provide more stringent conditions. For example, the wash solution may contain increased concentrations of detergents, salts, chelating agents, inhibitors and/or calcium. In some embodiments, the separating step can comprise other separation procedures, such as centrifugation, flow cytometry and/or precipitation.

In still some embodiments, neither analytes nor antibody-nucleic acid conjugates are immobilized, but are contacted in a fluid form. In such embodiments, un-coupled analytes and/or un-coupled antibody-nucleic acid conjugates can be separated from coupled analyte-antibody-nucleic acid complexes by various techniques as known in the art, including, e.g., by differences in molecular mass, chromatography, centrifugation, electrophoresis and/or filtration. See, e.g., techniques described in U.S. Pat No. 2003/0148335.

As FIG. 1 illustrates, sample analytes 103 and 104 can be mixed with corresponding internal (or exogenous) standards 107, either before or after coupling to corresponding nucleic acid tag 105. The term "exogenous" refers to the fact that the standards are generally not obtained from the specimen, but are exogenously added to the sample analytes. The term "internal" refers to the fact that, upon mixing with sample analytes, these standards are subjected to one or more of the same (or substantially the same) reactions as the sample analytes, e.g., co-amplification. In preferred embodiments, internal standards are provided for target and reference analytes and the internal standard for the target analyte is at a known concentration relative to that for the reference analyte. Internal standards can be provided for either or both nucleic acid analytes or non-nucleic acid analytes.

The internal standard for nucleic acid analyte 104 can comprise a competitive template for the nucleic acid 108. The internal standard for non-nucleic acid analyte 103 can comprise a competitive template 109 for the nucleic acid tag 105 which tags that analyte. In preferred embodiments, the competitive templates of at least two internal standards are at known concentrations relative to one another. "Competitive template" as used herein can refer to a nucleic acid that competes with another nucleic acid during an amplification reaction. That is, when present in a reaction mixture for amplifying a nucleic acid analyte or a nucleic acid tag, the competitive template competes to serve as the template for such amplification. In some embodiments, for example, the competitive template for a given nucleic acid has a structure allowing its amplification to the same or substantially the same extent as the given nucleic acid. The nucleic acid corresponding to a competitive template (CT) may be referred to as a native template (NT). For example, "native template" can refer to a nucleic acid corresponding to sample analyte that can serve as a template for amplification. For example, a nucleic acid analyte, a cDNA corresponding to a nucleic acid analyte, or a nucleic acid tagging a non-nucleic acid analyte can be referred to as "native template."

In preferred embodiments, a competitive template for a given nucleic acid can be amplified using one or more of the same primers as that of the given nucleic acid and/or can amplify with the same or substantially the same efficiency as the given nucleic acid. For example, primers can be designed to amplify a competitive template and its corresponding nucleic acid analyte or nucleic acid tag, as known in the art and/or as provided herein. The term "primer" generally refers to a nucleic acid capable of acting as a point of initiation of synthesis along a complementary strand when conditions are suitable for synthesis of a primer extension product. Some embodiments use a single primer approach, e.g., where a nucleic acid tag contains a primer binding sequence at one end and a complementary sequence at the opposite end. Some embodiments use a pair of primers.

In preferred embodiments, a given primer pair is designed to amplify a competitive template and its corresponding nucleic acid analyte or nucleic acid tag, but not to amplify (or not to substantially amplify) other nucleic acids in the co-amplification mixture. The primer pair can be designed such that under certain stringency conditions, hybridization to the desired templates is achieved but hybridization to other non-specific templates is hindered or prevented. For example, primers can be designed to improve or optimize PCR amplification of a nucleic acid and its competitive template under relatively stringent conditions (e.g., where annealing conditions occur at least about 60 or at least about 65 degrees Centigrade, and no more than about 69, or no more than about 75 degrees Centigrade).

As FIG. 1 illustrates, the competitive template can have a distinguishing feature 110 from the native template, e.g., allowing its amplified product to be distinguished from the amplified product of the nucleic acid analyte or nucleic acid tag. For example, in some embodiments, the competitive template can comprise mutants of the nucleic acid analyte or the nucleic acid used as a tag. For example, competitive template for a reference nucleic acid analyte may comprise a nucleic acid having a sequence similar to either strand of cDNA of a housekeeping gene, but having a distinguishable feature. Mutations can be point mutations, insertions, inversions, deletions, substitutions, additions, different nucleotide sequences, different sequence orders, or the like. For example, in some embodiments, a competitive template comprises at least one nucleotide that is different from its corresponding nucleic acid analyte or nucleic acid tag. In some embodiments, the competitive template comprises at least about two, at least about three, at least about 5, at least about 10, at least about 15, or at least about 20 nucleotides that are different. Longer deletions, insertions, inversions, substitutions and/or other alterations are provided in some embodiments.

In some embodiments, the nucleic acid sequence of the nucleic acid analyte or tag is artificially shortened to provide its corresponding competitive template. Some methods of producing artificially shortened competitive templates are known in the art, e.g., and may be generated according to the method described by Celi et al., *Nucleic Acids Res.* 21:1047 (1993).

In still some embodiments, the competitive template comprises an alteration that causes a loss and/or gain of one or more cleavage sites in the competitive template compared to its corresponding nucleic acid analyte or nucleic acid tag. For example, a base may be substituted in a competitive template sequence to result in the gain and/or loss of a restriction endonuclease recognition site, chemical cleavage site, or other specific cleavage site. Various programs may be used to identify and match one or two or more base mismatch sequences for known recognition sites. For example, the Map program within Genetics Computer Group software package (Devereux et al., supra, (1984)) may be used. In this program, cDNA sequences are obtained for a given nucleic acid, and then the sequence is evaluated for the presence of one or two base pair mismatches for known restriction endonucleases.

In some embodiments, the competitive template comprises an alteration that causes a loss and/or a gain of one or more specific recognition sites in the competitive template compared to its corresponding nucleic acid analyte or nucleic acid tag. For example, a base may be substituted in a competitive template sequence to result in a gain and/or loss of a protein binding site such as a transcription factor binding site. In some embodiments, distinguishing features include differences in ability to form a secondary structure; being single-stranded, double-stranded, or triple-stranded; being in A-, B- or Z-form; encoding biological activities, e.g., promoter activities; and the like. Other structural changes for distinguishing amplified product of a competitive template from amplified product of its corresponding nucleic acid will be apparent to those of skill in the art and are also within the scope of the instant invention.

Competitive templates can be synthesized by any techniques known in the art, as can be developed, and/or as described herein, e.g., with respect to synthesizing nucleic acid tags. Nucleic acid tags (and their corresponding competitive templates) can be designed to be distinguishable from each other by use of any of the distinguishing features described herein with respect to competitive templates, e.g. where the tags are used to identify multiple analytes in a given sample. Distinguishing features for different competitive templates can be the same, or substantially the same, or different.

As the nucleic acid tag used for a given analyte is generally arbitrary, nucleic acid tags can be selected for which suitable competitive templates are known or can be designed. For example, suitable pairs of nucleic acids and their corresponding competitive templates can be found at www.geneexpress-inc.com. In one embodiment, e.g., native template for catalase can be used for tagging a sample analyte, e.g., a target analyte, while the competitive template for catalase can be used in preparing internal standard for the target analyte. As another example, native template for β-actin can be used for tagging a sample analyte, e.g., a reference analyte, while the competitive template for β-actin can be used in preparing internal standard for the reference analyte. In preferred embodiments, nucleic acids and corresponding competitive templates that have been characterized, cloned, quantified, standardized and/or validated can be used. See, e.g., nucleic acid sequences provided in Crawford et al., *Biochem. Biophys. Res. Commun.* 293, 509-516 (2002). Validation preferably involves serial dilution to document lower detection thresholds for a given native/competitive template pair.

In some embodiments, different nucleic acid tag/competitive template pairs have the same or substantially the same melting temperature and/or can allow amplification with about the same efficiency. Melting temperature as used herein can refer to a temperature or range of temperatures at which about 50% of a nucleic acid is hybridized to its complementary strand. For example, in some embodiments, different nucleic acid tag/competitive template pairs have about the same number of nucleotides and/or about the same G:C content. In some embodiments, e.g., about the same annealing, denaturing and/or hybridization conditions can be used. For example, the difference between melting temperatures of different nucleic acid tag/competitive template pairs used can be less than about 30° C., less than about 20° C., less than about 10° C., less than about 5° C., or less than about 1° C. Using the same (or substantially the same) nucleic acid tag/competitive template pairs for different analytes in still some embodiments can further facilitate equal (or approximately equal) amplification efficiencies.

As FIG. 1 illustrates, internal standard for non-nucleic acid analyte 103 can further comprise an antagonist 111 for the analyte, where the antagonist is coupled to the competitive template 109 for the nucleic acid tag 105 of that sample analyte 103. "Antagonist" as used herein can refer to a moiety that competes with the analyte for complexing with a receptor. For example, in some embodiments, the antagonist for an analyte comprises the same (or substantially the same) molecule as the analyte itself. An antagonist may be prepared from a commercially available form of an antigen, e.g., where AFP is used as a reference analyte, commercially available AFP, preferably in a substantially pure and/or characterized form, can be used in preparing the corresponding internal standard. (Fitzgerald Industries Intl Inc (Concord, Mass.)). Substantially pure and/or characterized forms of other antigens are also commercially available, e.g., carcinoembryonic antigen. In some embodiments, a recombinant protein and/or synthetic peptide can serve as an antagonist, where the analyte comprises the corresponding naturally-occurring protein. In general, an antagonist can comprise any moiety that an analyte can be, e.g., as provided above.

An antagonist may be coupled to the competitive template by any technique described herein, known in the art, or as can be developed. For example, any of the approaches for coupling an analyte to its nucleic acid tag may be used to couple an antagonist for the analyte to a competitive template for the tag. In still some embodiments, an antagonist may be coupled to a competitive template by use of a fusion protein, e.g., a fusion protein comprising at least one domain comprising an antagonist for an analyte linked to at least one other domain comprising a nucleic acid-binding protein that recognizes and binds to the competitive template sequence for the nucleic acid tagging that analyte. In some embodiments, an antagonist may be coupled to competitive template in protein-nucleic acid fusion molecules. See, e.g., WO 01/16352; WO 01/14539 and/or WO 99/51773. For example, a protein-nucleic acid chimera can be prepared through in vitro translation or other techniques to provide fusion antagonists, obviating the step of conjugating nucleic acid.

As FIG. 1 illustrates, antagonist 111 can be coupled to competitive template 109 via an antibody 112, either directly or directly, as described above. For example, one or more techniques described above for conjugating antibodies (or other ligands) to nucleic acid tags can also be applied to conjugating antibodies (or other ligands) to competitive templates. In preferred embodiments, direct attachment is used. Direct attachment can help maintain the surrogate relationship between an analyte and its nucleic acid tag as well as between an antagonist and its competitive template.

In some embodiments, antibody 112 is conjugated to competitive template 109 using the same or substantially the same approach for conjugating antibody 106 to its nucleic acid tag 105. In some embodiments, the same (or substantially the same) type of antibody used for coupling analyte 103 to its tag 105 can be used for coupling the corresponding antagonist 111 to competitive template 109. For example, in some embodiments, monoclonal antibodies that recognize an epitope common to both the analyte and its antagonist can be used. An epitope is common to an analyte and its antagonist where a given antibody or other ligand can recognize and preferentially complex with the epitope on both the analyte and its antagonist over other analytes and other antagonists, under conditions used. In preferred embodiments, monoclonal antibodies cross-linked to competitive templates can be used to couple one molecule of antagonist to one copy of competitive template in a fixed (or substantially fixed) ratio, e.g., of about 1:1 (about equimolar). Other ratios may also be used, e.g., as provided above with respect to analytes and nucleic acid tags. In preferred embodiments, the internal standards provide a known and fixed (or substantially fixed) molar ratio of competitive template to antagonist.

As detailed above with respect to sample analytes, in preferred embodiments, conjugating a nucleic acid to an antibody (or other ligand) does not interfere or does not substantially interfere with the ability of the antibody (or other ligand) to recognize and preferentially complex with an antagonist for an analyte. For example, in preferred embodiments, affinity constants of both antibody-NT and antibody-CT conjugates remain above at least about $10^{-6}$ M, at least about $10^{-7}$ M, or at least about $10^{-8}$ M. Nonetheless, without being limited to a particular hypothesis or theory, variation due to reduced recognition and/or binding can be controlled, in some embodiments, by using the same or similarly conjugated antibodies for both coupling nucleic acid to an analyte and for coupling competitive template for the nucleic acid to the antagonist for the analyte. That is, the relationship between antibody-NT and antibody-CT conjugates need not be substantially affected where the potential decrease in antibody binding is the same or approximately the same for the two conjugates or where the difference in binding is constant (or approximately constant).

In preferred embodiments, the internal standards 107 are provided in a standardized mixture. A "standardized mixture" as used herein can refer to a mixture comprising a number of internal standards, e.g., a number of competitive templates and/or a number of competitive templates coupled to antagonists at known concentrations. In preferred embodiments, the standardized mixture comprises internal standards for at least two analytes in a sample, where the internal standards are at known concentrations relative to each other, and the second analyte serves as a "reference analyte" as described above.

For non-nucleic acid analytes, the standardized mixture provides antagonist of one analyte at a known concentration relative to antagonist for another analyte or relative to a competitive template for a nucleic acid analyte. Where antagonists are coupled at known and fixed (or substantially fixed) ratios to competitive templates, the standardized mixture provides competitive template for nucleic acid tagging one analyte at a known concentration relative to competitive template for a nucleic acid tagging another analyte or relative to a competitive template for a nucleic acid analyte. Accordingly, for both nucleic acid and non-nucleic acid analytes, the standardized mixture can provide competitive template for one analyte at a known concentration relative to competitive template for another analyte, which can serve as the "reference analyte." In this way, a given standardized mixture can comprise internal standards for different molecular materials (e.g., proteins, nucleic acids, small molecules, etc). In more preferred embodiments, the competitive templates (along with any coupled antagonists) are at fixed concentrations relative to other, up to and including all other, competitive templates in the mixture. A known amount, e.g., a known volume, of standardized mixture can be combined with the sample containing unknown amounts of analytes for analysis. Preparation and use of standardized mixtures are provided in more detail below.

In still some embodiments, a series of serially-diluted standardized mixtures is used to assay analytes in a mixture. "Serially-diluted standardized mixtures" can refer to two or more standardized mixtures in which one or more of the reagents in the standardized mixtures is serially-diluted. In some embodiments, one or more reagents in the standardized mixtures is serially-diluted relative to a different one or more of the reagents in the mixtures. For example, in preferred embodiments, internal standard for one analyte can be serially diluted relative to an internal standard for a reference analyte. For example, the series of standardized mixtures can provide competitive template (and any coupled antagonist) for one analyte at a series of known concentrations relative to competitive template (and any coupled antagonist) for another analyte. A known amount, e.g., a known volume, of one of the series of standardized mixtures can be combined with the sample containing unknown amounts of analytes for analysis. Preparation and use of serially-diluted standardized mixtures are described in more detail below.

As FIG. 1 illustrates, sample analytes 102 can be mixed with known amounts of their corresponding internal standards 107 and exposed to a receptor 113 that can form complexes with both analyte 103 and antagonist 111 for non-nucleic acid analytes. Non-nucleic acid analyte 103 can be mixed with internal standards 107 and/or exposed to the receptor 113 either before or after coupling to its corresponding nucleic acid tag 105. For example, in some embodiments, analytes are mixed with their corresponding internal standards before being allowed to couple to their nucleic acid tags. In some embodiments, analytes are mixed with their corresponding internal standards and exposed to a receptor for forming complexes before being allowed to couple to their nucleic acid tags. In some embodiments, analytes may be coupled to their nucleic acid tags before mixing or exposure to receptors. One of skill in the art will recognize other orders in which the steps may be performed. For example, in still some embodiments, the mixing and exposing steps can be performed simultaneously. In still some embodiments, internal standards can be mixed with sample analytes in vivo, e.g., as described in U.S. Pat No. 2003/0148335. Mixing and/or exposing as used herein can refer to any technique for providing access of one component or types of component to one or more other components or types of components. In some embodiments, solutions mixed with and/or exposed to one another comprise reagents to facilitate mixing, interaction, uptake, and/or other physical, chemical and/or biochemical phenomenon between the mixed and/or exposed components. In general, mixing can be understood to form a resulting mixture of the components mixed.

The receptor 113 can comprise any moiety capable of recognizing and preferentially complexing with a given analyte over other analytes in the mixture, and with the corresponding antagonist for the analyte over other antagonists in the mixture, under conditions used. For example, the receptor can comprise any of the ligands described herein, including, but not limited to antibodies, including phage-displayed antibodies. In some embodiments, receptors can comprise lectins, lipids, carbohydrates, sugars, steroids, polymers, nucleic acids, whole cells, cell surface proteins, and/or microbes. In some embodiments, receptors can comprise artificial ligands, such as peptoids, described above. Peptoids may provide more stable means for preparing a substrate for immobilizing analytes and internal standards. In some embodiments, natural and/or modified peptides, e.g., peptides evolved to bind analytes can be obtained and can provide chemically stable receptors in some embodiments. In still some embodiments, receptors can comprise antigens (e.g., where an analyte to be assayed comprises an antibody); naturally-occurring and/or synthetic binding pairs; binding motifs, e.g., calodulin binding motif and/or protein A/G binding motif; artificial lock and key pairs, e.g., plastic or silicon imprints of a protein, carbohydrate, lipid, and/or lectin; or nucleic acids evolved to bind to analytes, e.g., aptamers evolved to bind proteins. Receptors may also comprise any combinations of examples of receptors listed herein. Any of the features and/or characteristics described above for selecting antibodies or other ligands, and/or any of the approaches for coupling nucleic acid to analyte or antagonist, can also be used in selecting receptors. For example, in some embodiments, the receptor can comprise an antibody that recognizes and preferentially binds to an analyte and its corresponding antagonist, preferably reducing spurious and/or non-specific binding, e.g., by environmental contaminants.

In preferred embodiments, a monoclonal antibody is used as the receptor. In some embodiments, a two antibody sandwich assay may be used. For example, where an analyte is coupled to its nucleic acid tag via a monoclonal antibody that recognizes a first epitope on the analyte, the receptor may comprise a different monoclonal antibody that recognizes a second (different) epitope. In some such embodiments, antagonist for the analyte may be coupled to competitive template for the nucleic acid tag via a monoclonal antibody that recognizes a first epitope common to both the analyte and its antagonist, and the receptor may comprise a different monoclonal antibody that recognizes a common second (different) epitope on both the analyte and its antagonist. Without being limited to given theory or hypothesis, the use of two monoclonal antibodies targeted at different epitopes of an analyte (and its antagonist) can increase assay specificity exponentially.

In preferred embodiments, an analyte and its corresponding antagonist compete with each other for complexing with the receptor where each can bind with the same or substantially the same binding affinities, binding constants, etc. For example, where a non-nucleic acid analyte is coupled to its nucleic acid tag before mixing and exposure to receptors, the analyte and its corresponding antagonist are each coupled to nucleic acids, e.g, via antibodies, and can present substantially equal-sized complexes for competing for the receptor. In some embodiments, the amount of the receptors to which analytes and antagonists are exposed is less than the combined amounts of analyte and antagonist molecules, e.g., to promote competition for complexing with the receptors. In some embodiments, chemical and/or biochemical environments can be used that facilitate and/or promote recognition and/or preferential complexing, e.g, as provided above.

In preferred embodiments, either the analyte or its corresponding antagonist is substantially equally likely to complex with the receptor. Under such conditions, the ratio of complexes formed with an analyte as compared with its antagonist is preferably substantially equal to the ratio of analyte and its antagonist in the mixture formed by mixing sample analytes with their corresponding internal standards. That is, the relative representation of sample analyte to standard antagonist complexed with receptors can provide a measure of the concentration of analyte in the sample. Without being limited to a particular hypothesis, the use of an internal standard antagonist that competes with a sample analyte for complexing with a common receptor can reduce variation in efficiency in receptor recognition and/or receptor binding. Nucleic acids representing the sample analytes and their competitive templates can be amplified to allow detection and/or quantification of lower amounts of analytes, e.g., as detailed below.

In some embodiments, the receptor is immobilized on a substrate. The substrate may be any surface or support upon which receptor molecules can be immobilized, including one or more of a solid support (e.g., glass such as a glass slide or a coated plate, silica, plastic or derivatized plastic, paramagnetic or non-magnetic metal), a semi-solid support (e.g., a polymeric material, a gel, agarose, or other matrix), and/or a porous support (e.g., a filter, a nylon or nitrocelluloase membrane or other membrane). In some embodiments, synthetic polymers can be used as a substrate, including, e.g., polystyrene, polypropylene, polyglycidylmethacrylate, aminated or carboxylated polystyrenes, polyacrylamides, polyamides, polyvinylchlorides, and the like. In preferred embodiments, the substrate comprises a thermocycler-ready immunoassay plate or other surface suitable for use in PCR amplification.

The surface of the substrate or support may be planar, curved, spherical, rod-like, pointed, waffer or waffer-like, or any suitable two-dimensional or three-dimensional shape on which receptor molecules may be immobilized, including, e.g., films, beads or microbeads, tubes or microtubes, wells or microplate wells, microfibers, capillaries, a tissue culture dish, magnetic particles, pegs, pins, pin heads, strips, chips prepared by photolithography, etc. In some embodiments, the surface is UV-analyzable, e.g., UV-transparent, e.g., to facilitate detection of nucleic acids immobilized thereon, e.g., by virtue of being coupled (directly or indirectly) to complexed antagonists and analytes. In some embodiments, the substrate itself serves as the receptor, e.g., where analytes to be assayed become directly attached to the support surface of a substrate. See, e.g., McKie et al., supra, (2001).

Immobilization may be achieved in any number of ways, known in the art, described herein, and/or as can be developed. For example, immobilization may involve any technique resulting in direct and/or indirect association of an analyte (and its corresponding antagonist) with the substrate, including any means that at least temporarily prevents or hinders its release into a surrounding solution or other medium. The means can be by covalent bonding, non-covalent bonding, ionic bonding, electrostatic interactions, Hydrogen bonding, van der Waals forces, hydrophobic bonding, or a combination thereof. For example, immobilization can be mediated by chemical reaction where the substrate contains an active chemical group that forms a covalent bond with receptors. For example, an aldehyde-modified support surface can react with amino groups in protein receptors; or amino-based support surface can react with oxidization-activated carbohydrate moieties in glycoprotein receptors; a support surface containing hydroxyl groups can react with bifunctional chemical reagents, such as N,N dissuccinimidyl carbonate (DSC), or N-hydroxysuccinimidyl chloroformate, to activate the hydroxyl groups and react with amino-containing receptors. In some embodiments, support surface of the substrate may comprise animated or carboxylated polystyrenes; polyacrlyamides; polyamines; polyvinylchlorides, and the like. In still some embodiments, immobilization may utilize one or more binding-pairs to bind or otherwise attach a receptor to a substrate, including, but not limited to, an antigen-antibody binding pair, hapten/anti-hapten systems, a avidin-biotin binding pair; a streptavidin-biotin binding pair, a folic acid/folate binding pair; photoactivated coupling molecules, and/or double stranded oligonucleotides that selectively bind to proteins, e.g., transcriptional factors. In some embodiments, receptors are immobilized via one or more pairs of complementary nucleic acids, e.g., a DNA molecule. In some embodiments, the sequence of the nucleic acid molecule can facilitate release of the receptor complexes, for example, as described in U.S. Pat No. 2005/0026161.

In some embodiments where receptors comprise antibodies, TopYield™ Strips can be used as a substrate for immobilization (Nalge Nunc International, Rochester, N.Y.). The TopYield™ Strips used can be improved or optimized for antigen-antibody binding, e.g., the binding of protein antigens. In some embodiments, an ELISA protocol can be used to further improve or optimize binding where the target analytes are polysaccharides (see, e.g., Prinz et al., *Immunology* 110(2):242-249 (2003); Prinz et al., supra, (2004); Lesinski et al., supra, (2001); and Grothaus et al., supra, (2000) or proteins (see, e.g., Westerink et al., supra, (2001); Coeshott et al., supra, (2004)). Further details, e.g., are provided in Example I.

In some embodiments, the receptor is not immobilized. For example, in some embodiments, analytes and/or antagonists are immobilized on a substrate, e.g., by any of the techniques provided above, including immobilization in a biological structure, and exposed to soluble receptors for complexing. In still some embodiments, neither analytes, nor antagonists nor receptors are immobilized, but are contacted in a fluid form. In such embodiment, un-complexed materials can be separated from complexes formed by various techniques as known in the art, including, e.g., by differences in molecular mass, chromatography, centrifugation, electrophoresis and/or filtration. See, e.g., techniques described in U.S. Pat No. 2003/0148335.

Those of skill in the art will appreciate other approaches, modifications and/or variations for designing immuno-assays, based on the teachings provided herein, including e.g., immobilizing analyte directly to a substrate and complexing with a single antibody; immobilizing analyte directly to a substrate and complexing with an antibody-nucleic acid tag conjugate via a second antibody; immobilizing receptors via a second antibody; and/or sandwich triple-antibody system. See, e.g., Schiavo et al., *PharmaGenomics* 4(1):36-45 (2004).

In preferred embodiments, multiple non-nucleic acids analytes are assayed in a given sample. More preferred embodiments allow for simultaneous assessment of multiple analytes. Where multiple non-nucleic analytes are assayed, more than one type of receptor may be used. For example, a second non-nucleic acid analyte can be allowed to couple to a second nucleic acid, mixed with a known amount of a corresponding antagonist that is coupled to a competitive template for the second nucleic acid, and exposed to a second receptor that can form complexes with both the second non-nucleic acid analyte and its antagonist.

Figure 2:
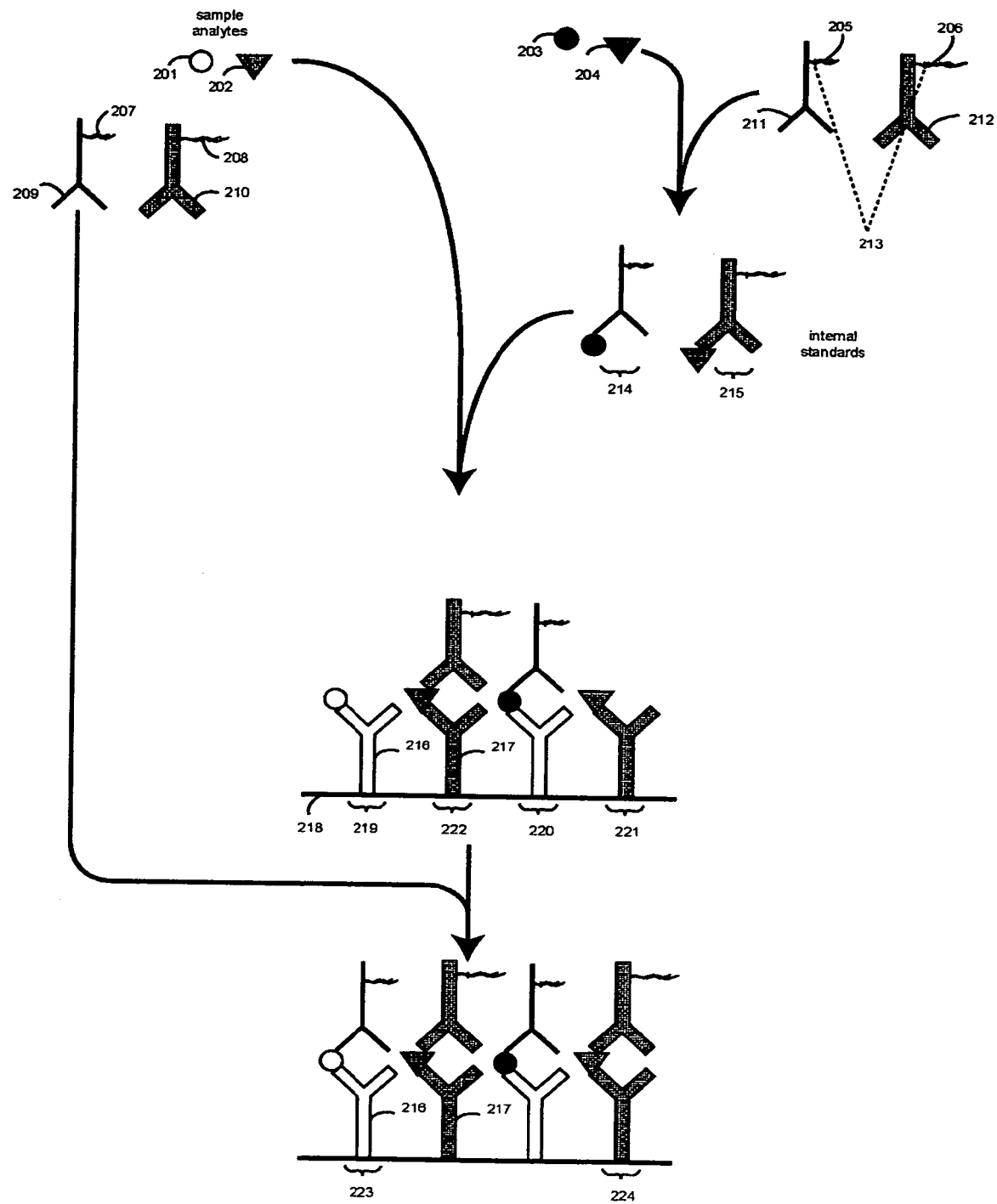
FIG. 2 illustrates an embodiment of the present invention where multiple non-nucleic acid analytes are assayed.

FIG. 2 illustrates an embodiment of the present invention where multiple non-nucleic acid analytes are assayed. The embodiment uses a two-antibody sandwich assay format. Internal standards for non-nucleic acid analytes 201 and 202 can be prepared comprising antagonist 203 and 204 for each of the two analytes coupled to competitive templates 205 and 206 for each of two nucleic acid tags 207 and 208. Coupling may comprise direct and/or indirect attachment, e.g., again as detailed above. In preferred embodiments, monoclonal antibodies 209, 210, 211, and 212 are used both for coupling analytes to nucleic acid tags and for coupling antagonists to competitive templates. As detailed above, the competitive templates can each have a distinguishing feature 213 with respect to the corresponding nucleic acid tags.

As FIG. 2 illustrates, nucleic acid tag 207 can be conjugated to monoclonal antibody 209 that can couple analyte 201. Competitive template 205 (corresponding to nucleic acid tag 207) can be conjugated to monoclonal antibody 211 that can couple antagonist 203 (corresponding to analyte 201). In some embodiments, for example, antibodies 209 and 211 can recognize and preferentially bind an epitope common to both analyte 201 and its antagonist 203. Nucleic acid tag 208 can be conjugated to monoclonal antibody 210 that can couple analyte 202. Competitive template 206 (corresponding to nucleic acid tag 208) can be conjugated to monoclonal antibody 212 that can couple antagonist 204 (corresponding to analyte 202). In some embodiments, for example, antibodies 210 and 212 can recognize and preferentially bind an epitope common to both analyte 202 and its antagonist 204. The antibody-competitive template conjugates can form internal standards 214 and 215. Other approaches for coupling antagonists and competitive templates may also be used, again as detailed above. The internal standards can be mixed together to form a standardized mixture, e.g., where internal standard 214 (and competitive template 205) is at a known concentration relative to internal standard 215 (and competitive template 206), e.g., as explained above.

As FIG. 2 illustrates, sample analytes 201 and 202 can be mixed with known amounts of internal standards 214 and 215 and exposed to receptors 216 and 217 immobilized to a substrate 218. The receptor, substrate and/or immobilization used may be any known in the art, as can be developed, and/or as provided above. Various approaches regarding the mixing and/or exposing steps can also be used, e.g., again as detailed above.

As FIG. 2 illustrates, receptor 216 can form complexes 219 and 220 with sample analyte 201 and internal standard antagonist 203, respectively. Receptor 217 can form complexes 221 and 222 with sample analyte 202 and internal standard antagonist 204, respectively. Receptor 216 can comprise a monoclonal antibody that recognizes a second (different) epitope on analyte 201 or on antagonist 203 compared with antibodies 209 and 211. Receptor 217 can comprise a monoclonal antibody that recognizes a second (different) epitope on analyte 202 or on antagonist 204 compared with antibodies 210 and 212.

In a preferred embodiment, analyte 201 and antagonist 203 complex with receptor 216 with the same or substantially the same binding affinities, binding constants, etc., so that the ratio of complexes 219 and 220 formed will substantially represent the relative amounts of analyte 201 and its internal standard 214 upon mixing. Similarly, in preferred embodiments, analyte 202 and antagonist 204 complex with receptor 217 with the same or substantially the same binding affinities, binding constants, etc., so that the ratio of complexes 221 and 222 formed will substantially represent the relative amounts of analyte 202 and its internal standard 215 upon mixing. In some embodiment, a washing step removes un-complexed sample analytes and internal standards, and/or non-specific materials, e.g. as described in more detail above.

In some embodiments, receptors for two or more different analytes can be localized in different positions on a substrate. "Different positions" can refer to different regions, areas, spots, locations or addresses that are spatially distinguishable, e.g. where different receptors are immobilized at different positions on the substrate. Different positions may also indicate localization in different vessels. "Vessels" as used herein may refer to any object capable of allowing a reaction mixture to exist therein and/or thereon. For example, a vessel may comprise a well, micro-well, tube, nanofluidic and/or microfluidic reservoir and/or channel, capillary, groove, surface, and/or other container and/or depression on a substrate. Different positions may also indicate localization on different microbeads (e.g., on different batches of microbeads) that are themselves spatially and/or spectrally distinguishable. See, e.g., Kettman et al., *Cytometry* 33:234-243 (1998).

Where different receptors are located in different positions, the sample and internal standards can be combined, and preferably mixed, before being applied to the different positions. Without being limited to a given hypothesis or theory, this can fix (or substantially fix) the relative representation of an analyte in the sample to its respective internal standard in the standardized mixture. Also, where receptors for different analytes are localized in different positions, the same or substantially the same nucleic acids can be used to tag two or more different analytes. In such embodiments, the same or substantially the same competitive templates can be coupled to different antagonists for the different analytes. In such embodiments also, the same or substantially the same primer pairs can be used in amplification of the nucleic acid tags, e.g., facilitating equal (or approximately equal) amplification efficiencies, as described above.

In other embodiments, receptors for two or more different analytes can be co-localized, rather than being localized in different positions. For example, receptors for two or more different analytes may be immobilized in one vessel, e.g., in one TopYield™ well. This can allow two non-nucleic acid analytes to be assessed in a given reaction chamber. Steric hindrance issues can be reduced using lower concentrations of receptors. In some embodiments, differences in attachment of different receptors to the substrate can be assessed to indicate suitable concentrations for each receptor for coating. Further details, e.g., are provided in Example 1.

Where receptors for different analytes are co-localized, different nucleic acids can be used to tag different analytes in a sample, and, correspondingly, different competitive templates can be coupled to different antagonists for the different analytes. In preferred embodiments, pre-tagged monoclonal antibodies are used where different types of antibodies are labeled with nucleic acid tags of different lengths. See, e.g., Hendrickson et al., supra, (1995). In some embodiments, nucleic acid tags are identified from each other based on a property other than length. Any distinguishing feature can be used, e.g., as discussed above in the context of distinguishing competitive templates.

As FIG. 2 illustrates, immobilized analytes 201 and 202 can be allowed to couple to nucleic acid tags 207 and 208, respectively, by applying nucleic acid conjugates of antibodies 209 and 210. These can couple to the immobilized analytes 201 and 202 to form complexes 223 and 224, respectively. Any of the chemical and/or biochemical environments described above can be used to facilitate and/or promote recognition and/or preferential binding. In preferred embodiment, none or substantially none of the nucleic acid tags 207 and 208 become coupled to immobilized antagonists 203 and 204. In some embodiments, a washing step removes un-coupled conjugates, e.g., excess conjugates, again as described in more detail above. Nucleic acids 207 and 208, representing sample analytes 201 and 202, and their competitive templates 205 and 206, representing corresponding antagonists 203 and 204, can then be amplified to facilitate detection and/or quantification, e.g., as described below.

Amplification can be achieved by any methods known in the art, as can be developed, and/or disclosed herein for amplifying nucleic acid molecules. When polymerase chain reaction (PCR) amplification is used, conditions can include the presence of ribonucleotide and/or deoxyribonucleotide di-, tri-, tetra-, penta- and/or higher order phosphates; primers for PCR amplification for at least one nucleic acid and its corresponding competitive template; and at least one polymerization-inducing agent, such as reverse transcriptase, RNA polymerase and/or DNA polymerase. Examples of DNA polymerases include, but are not limited to, *E. coli* DNA polymerase, Sequenase 2.0®, T4 DNA polymerase or the Klenow fragment of DNA polymerase 1, T3, SP6 RNA polymerase, AMV, M-MLV, and/or Vent polymerase, as well as ThermoSequenase™ (Amersham) or Taquenase™ (Scien-Tech, St Louis, Mo.). Further examples include thermostable polymerases isolated from *Thermus aquaticus, Thermus thermophilus, Pyrococcus woesei, Pyrococcus furiosus, Thermococcus litoralis*, and *Thermotoga maritima*. The polymerization-inducing agent and nucleotides may be present in a suitable buffer, which may include constituents which are co-factors or which affect conditions such as pH and the like at various suitable temperatures. PCR primers used are preferably single stranded, but double-, triple- and/or higher order stranded nucleotide molecules can be practiced with the present invention. Amplification may be carried out for a number of cycles of PCR, e.g., at least about 10, at least about 20, at least about 30, at least about 35, at least about 40, or at least about 50 cycles in some embodiments.

In some embodiments, e.g., amplified fragment length polymorphism ("AFLP") technology may be used. AFLP can bring about selective amplification of restriction fragments from a total digest of genomic DNA. See, e.g., Janssen et al., *Microbiology* 142(Pt 7):1881-93 (1996); Thomas et al., *Plant J.* 8(5):785-94 (1995); Vos et al., *Nucleic Acids Res.* 23(21): 4407-14 (1995); Bachem et al., *Plant J.* 9(5):745-53 (1996); and Meksem et al., *Mol. Gen. Genet.* 249(1):74-81 (1995).

The ligase detection reaction ("LDR") and/or the ligase chain reaction ("LCR") provide additional methods that may be used in some embodiments of the instant invention. See, e.g., Barany et al., *Gene* 109:1-11 (1991); Barany, *Proc. Natl. Acad. Sci. USA* 88:189-193 (1991); and Barany, *PCR Methods and Applications,* 1:5-16 (1991). In some embodiments, more than one amplification method may be used, e.g., PCR amplification followed by LDR detection or LCR. See, e.g., Grossman et al., *Nucleic Acids Res.* 22:4527-4534 (1994); and Eggerding et al., *Human Mutation* 5:153-165 (1995) (detecting 61 cystic fibrosis alleles); Feero et al., *Neurology* 43:668-673 (1993) (detecting 6 hyperkalemic periodic paralysis alleles); Day et al., *Genomics* 29:152-162 (1995) and Day et al., *Hum. Mol. Genet.* 5(12):2039-48 (1996) (detecting 20 21-hydroxylase deficiency alleles); White et al., *Proc. Natl. Acad. Sci. USA* 83:5111-5115 (1986) (describing that most of mutations causing 21-hydroxylase deficiency result from recombination between an inactive pseudogene (CYP21P) and a normally-active gene (CYP21), as the two genes share about 98% homology); Day et al., supra, (1995) (distinguishing insertion of a single T nucleotide into a $(T)_7$ tract); and Day et al., supra, (1996) (combining PCR/LDR and microsatellite analysis to reveal some unusual cases of PCR allele dropout).

Other amplification techniques known in the art, described herein, and/or that may be developed, can also be used in some embodiments of the instant invention. For example, some embodiments use asymmetric polymerase chain reaction, unidirectional linear polymerase reaction (LPR); T7 polymerase reaction (see, e.g., Zhang et al., *Proc. Natl. Acad. Sci. USA* 98(10): 5497-5502 (2001)), rolling circle amplification, immunoRCA (see, e.g., Schweitzer et al., supra, (2000)), real-time quantitative PCR, Amplifluor™ PCR, cleavage/invader amplification, transcription mediated amplification, forming and sequencing concatemers, and/or strand displacement amplification. Any of the amplification techniques described herein can also be used in any combination with each other and/or with any other amplification techniques.

For non-nucleic acid analytes, nucleic acids tags of receptor complexes can be amplified. For example, a nucleic acid tag representing a sample analyte can be co-amplified with its competitive template representing corresponding antagonists. The ratio of a complexed nucleic acid tag to its complexed competitive template can provide a measure of the amount of analyte in the sample, and this ratio can be substantially maintained during co-amplification, according to some embodiments provided herein. Co-amplification can occur while the nucleic acids are immobilized on a substrate, e.g., without disassociating the tag from the immobilized complex. See, e.g., Schweitzer et al., supra, (2000). Where immobilized nucleic acids are amplified, one or more techniques may be used to improve or optimize amplification efficiency. For example, in some embodiments, TopYield™ Strips (Nalge Nunc International, Rochester, N.Y.) are used. Such support surfaces are compatible with PCR equipment, thereby eliminating the transfer of solutions for conducting complexing and amplification steps.

In other embodiments, the nucleic acids can be disassociated and/or released and then co-amplified. Releasing nucleic acid tags can be achieved by any techniques known in the art, described herein, and/or as can be developed. For example, some embodiments use physical, chemical and/or enzymatic treatments that can dissociate nucleic acid tags from the receptor complexes. For example, where double stranded nucleic acid tags are used, increasing temperature can release the one strand of the tag that may not be covalently bound to the antibody (or other ligand), e.g., by heat denaturation of complementary strands. In some embodiments, double stranded tags can be released from complexes by endonuclease cleavage, e.g., if a restrictive site is designed in the nucleic acid tag. Some embodiments may involve release of the immobilized receptor, e.g. as described in U.S. Pat No. 2005/0026161. A nucleic acid tag can also be released by enzymatic cleavage of the antibody or other ligand to which it is attached, for example, by treatment with trypsin, pepsin, proteinase K; and the like. Chemical reaction, such as hydrolysis in HCl solution, or dissociation of disulfide-bonds, e.g. using beta mercapto-ethanol, DTT, and the like, can also be used. Dissociation reagents can affect subsequent reactions, such as nucleic acid amplification, labeling with detectable moiety and/or detection, etc. In order to help neutralize and/or inactivate the dissociation reagents, heating can be used to inactivate enzymes by protein denaturation, and/or an enzyme inhibitor can be used to inactivate enzymatic activities. For chemical reagents, a neutralization reagent can be added to inactivate the reagent, e.g. alkaline can be used to neutralize HCl.

For nucleic acid analytes, the analyte and its corresponding competitive template can be co-amplified with each other, or also with other nucleic acids.

In some embodiments, more than one nucleic acid (and its corresponding competitive template) are co-amplified, e.g., more than one nucleic acid analyte and/or nucleic acid tag (and the corresponding competitive templates). In some embodiments, the number of co-amplified nucleic acids is at least two where the second nucleic acid represents to a reference analyte. In some embodiments, the number of co-amplified nucleic acids is at least about 50, at least 100, at least about 200, at least about 300, at least about 500, at least about 800, at least about 1,000, at least about 5,000, at least about 10,000, at least about 50,000, or at least about 100,000 nucleic acids, preferably each with its corresponding competitive template. In preferred embodiments, a plurality of nucleic acids representing a plurality of analytes in a sample can be measured simultaneously.

In some embodiments, one or more precautions are taken to reduce or eliminate cross-contamination of amplification reactions. For example, in some embodiments, equipment used in PCR amplifications is washed regularly, e.g., with NaOH solution. For example, an automatic liquid handler used in some embodiments can be washed once a week with NaOH solution. In some embodiments, filtered pipette tips are used. In some embodiments, PCR reactions are set up in a laminar flow hood. Further, some embodiments use controls with no nucleic acid to monitor contamination. The use of primer pairs with low detection thresholds can also help detect contamination in some embodiments. In some embodiments, working surfaces, tubes, pipetters, tips, etc, can be irradiated with UV light, e.g., to destroy contaminating DNA. In some embodiments, tags, competitive templates, and primers are designed so that the amplified products are distinguishable, preferably substantially distinguishable from anticipated contaminant DNA.

Relative amounts of amplified products can be compared. As used herein "amplified product" can refer to any nucleic acid synthesized at least partly by base-complementary incorporation using another nucleic acid as template by any amplification technique, e.g. as detailed above. An amplified product may also be referred to an amplicon and/or amplimer herein. In some embodiments, the amount of amplified product of a nucleic acid representing a sample analyte is compared to the amount of amplified product of its competitive template. A nucleic acid representing a sample analyte can refer to, e.g. a nucleic acid tag for a non-nucleic acid analyte, or a cDNA molecule corresponding to a nucleic acid analyte and/or a nucleic acid analyte itself. A nucleic acid representing a sample analyte to be assayed can be referred to herein as a "target nucleic acid," and the sample analyte referred to as a target analyte. In some embodiments, comparison involves obtaining a relation, e.g., a first relation reflecting the amplified amounts of the target nucleic acid compared with the amplified amounts of its competitive template. In preferred embodiments, this relation is provided as a ratio, e.g., a first ratio of the amount of amplified product of the target nucleic acid to the amount of amplified product of its competitive template, e.g., where the target nucleic acid and its competitive template are co-amplified. Such relations provide a comparison of the amount of sample analyte to the amount of its internal standard, (e.g., comprising competitive template or competitive template coupled to antagonist). Because a known amount of internal standard is used, the amount of sample analyte can be determined.

In some embodiments, the amount of amplified product of a target nucleic acid is further compared to a reference nucleic acid. "Reference nucleic acid" as used herein can refer to a nucleic acid representing a reference analyte. For example, the reference nucleic acid can comprise a nucleic acid analyte, a cDNA molecule corresponding to a nucleic acid analyte, or a nucleic acid tag for a non-nucleic acid analyte, where the nucleic acid or non-nucleic acid analyte serves as a reference, e.g. as described above. In preferred embodiments, the reference nucleic acid is itself compared to its competitive template. For example, in some embodiments, the amount of amplified product of a reference nucleic acid is compared to the amount of amplified product of its competitive template. In some embodiments, e.g., this comparison involves obtaining a relation, e.g., a second relation reflecting the amplified amount of reference nucleic acid compared with the amplified amount of its competitive template. In preferred embodiments, this relation is provided as a ratio, e.g., a second ratio of the amount of amplified product of reference nucleic acid to the amount of amplified product of its competitive template, e.g., where the reference nucleic acid and its competitive template are co-amplified.

In preferred embodiments, comparison of the target nucleic acid to the reference nucleic acid involves comparing the first and second relations described above. This comparison can serve to "normalize" measurements of the analyte being assayed. For example a relation reflecting how the first relation compares with the second relation can be obtained. In some embodiments, this relation compares the first ratio to the second ratio, e.g., as a ratio of the first and second ratios.

The adjectives "first," "second," "third" and so forth, as used herein, do not necessarily indicate any order of preference, importance, chronology, or degree of a quality, concentration, and/or amount. Rather the terms are used to differentiate nouns qualified by the adjectives, e.g., a first and a second ratio can mean two different ratios; a second epitope can mean a different epitope from that referred to as the first epitope.

In more preferred embodiments, the relation obtained by comparing the first and second relations remains substantially constant beyond the exponential phase of amplification of one or more of the nucleic acids amplified. Substantially constant can refer to variations of +/−about 1%, about 5%, about 10%, about 15%, or about 20% of an absolute constant number.

In preferred embodiments, amplification and/or normalization of nucleic acid tags, in accordance with some embodiments taught herein, allow detection and/or quantification of small amounts of non-nucleic acid analytes. This provides a lower detection threshold that those typically obtained using an enzyme substrate (e.g ELISA) or a radionuclide approach, where signal cannot be amplified to the same extend as a nucleic acid tag. For example, some embodiments of the instant invention provide a detection threshold of at least about 3, at least about 4, at least about 5, at least about 6, or at least about 7 orders of magnitude lower than conventional ELISA (see, e.g., Komatsu et al., *Clin. Chem.* 47, 1297-1301 (2001); Adler et al., supra, (2003); Joerger et al., supra, (1995); Sugawara et al., *J. Immunol.* 165(1):411-418 (2000); Ren et al., *Ann. NY Acad. Sci.* 945, 116-118 (2001); Niemeyer et al., *Nucleic Acids Res.* 27(23): 4553-4561(1999)). For example, in some embodiments, the sample may comprise less than about 1,000 molecules, less than about 500 molecules, or less than about 300 molecules of an analyte to be assayed. In preferred embodiments, these amounts can be detected, quantified and/or enumerated. In preferred embodiments, e.g., less than about 100 molecules, less than about 60 molecules, e.g., less than about 30 molecules, less than about 10 molecules, less than about 6 molecules, or about 1 molecule of analyte can be enumerated in a sample. For example, in some embodiments, a single (or individual) molecule of analyte can be measured. For non-nucleic acid analytes, e.g., antigens, the number of molecules of the analyte found in a sample or per cell can be referred to as the antigen copy number. For nucleic acid analytes, the number of molecules of the analyte can also be referred to as the copy number of the nucleic acid found in a sample, or per cell.

In some embodiments, another assayed analyte can serve as a second reference analyte. That is, another one of the nucleic acids amplified can serve as a second reference nucleic acid, e.g., whether the nucleic acid is a nucleic acid analyte, a cDNA molecule corresponding to a nucleic acid analyte, or a nucleic acid tagging a non-nucleic acid analyte. In such embodiments, measuring the amount of target analyte can comprise obtaining a third relation that compares amplified product of this second reference nucleic acid to amplified product of its competitive template; and comparing the first and third relations, e.g., first and third ratios. Also, in some embodiments, data calculated using a first reference analyte can be re-calculated relative to that of another reference analyte.

In some embodiments, using two or more reference analytes can provide an understanding of inter-specimen and/or inter-sample variation among the references. In some embodiments, for example, β-actin and GAPD can be used as first and second reference analytes, where one or both comprise mRNA transcripts and/or one or both comprise a β-actin and/or GAPD protein products. There is a significant correlation between the ratio of β-actin/GAPD expression and cell size (Willey et al., *Am. J. Respir. Cell Mol. Biol.* 19, 6-17 (1998)), which may make use of these 2 reference analytes preferred in some embodiments. In some embodiments, any amplified nucleic acid or combination of nucleic acids, including all amplified nucleic acids, representing a sample analyte, can be used as a reference nucleic acid. The number of sample analytes that must be quantitated for normalization to any of the analytes to result in adequate normalization may vary depending on the samples and/or specimen being studied.

In some embodiments, comparing the first and second or first and third relations can provide a "ratio of ratios" corresponding to a numerical value. In some embodiments, numerical values for various assayed analytes, e.g., for various non-nucleic acid analytes as well as for various nucleic acid analytes, are provided as a database, as described in more detail below. For example, such a database can be used in clinical diagnostic testing.

In some embodiments, obtaining the comparisons, e.g., the first, second and/or third ratios, involves measuring the amounts of amplified product of each of the target nucleic acid(s), the competitive template(s) for the target nucleic acid, the reference nucleic acid(s) and the competitive template(s) for the reference nucleic acid. Any method capable of quantifying nucleic acids having a distinguishable feature (e.g., having different sizes and/or sequences) can be used. Quantifying methods may involve separating and/or isolating the amplified product, for example, by use of electrophoresis, hybridizations such as arrays, mass spectrometry, chromatography, HPLC and/or other methods known in the art for separating different nucleic acid molecules.

The electrophoresis used may be one or more of gel electrophoresis (e.g., agarose and/or polyacrylamide gel electrophoresis), microfluidic electrophoresis, capillary electrophoresis (e.g., using a capillary electrophoresis device like PE 310 or a microfluidic CE device like Agilent 2100 or Calipertech AMS 90 high-throughput system), and/or other types of electrophoresis devices known in the art. See, e.g., Gilliland et al., *Proc Natl. Acad. Sci. USA* 87, 2725-2729 (1990); Apostolakos et al., *Analytical Biochem.* 213, 277-284 (1993). Further, capillary electrophoresis (CE), in particular, microfluidic CE technology, can allow measurement of nucleic acid in very small volumes. See, e.g., T. S. Kanigan et al., in Advances in Nucleic Acid and Protein Analyses, Manipulation, and Sequencing, P. A. Limbach, J. C. Owicki, R. Raghavachari, W. Tan, Eds. Proc. SPIE 3926: 172, (2000). Other electrophoresis devices that may be used include, for example, Agilent or AB1 310. In some embodiments, separation of amplified product on agarose gel, a PerkinElmer 310 CE (ABI Prism 310 Genetic Analyzer), and a 2100 Bioanalyzer microfluidic CE (Agilent, Santa Clara, Calif., USA) were shown to provide statistically similar and reproducible results. Crawford et al., *Quantitative end-point RT-PCR expression measurement using the Agilent* 2100 *Bioanalyzer and standardized RT-PCR.* Agilent Application Note 5988-3674EN, September 2001, 1-8.

Where amplified products are to be separated by electrophoresis, the size of the nucleic acid tags, competitive templates and/or reference nucleic acid(s) can be selected to differ from each other and/or to differ from that of other nucleic acid analytes being assayed. For example, in some embodiments, amplified product generated from different nucleic acid tags coupled to different sample analytes are of sufficiently different sizes to be separated by electrophoresis. Further, in some embodiments, amplified product generated from the competitive template for a nucleic acid tag and the nucleic acid tag are of sufficiently different sizes to be separated by electrophoresis. Designing primers that amplify different sized products can support automation and high throughput separation and quantification methods, including, e.g., capillary gel and microchannel capillary electrophoresis (CE), MALDI-TOF, and HPLC.

In some embodiments, a size difference is achieved by using a competitive template for a given nucleic acid that is longer or shorter that the given nucleic acid. In some embodiments, this size differential can be achieved by restriction endonuclease digestion of the amplified product where the competitive template differs from its corresponding nucleic acid by the addition or lack of a restriction endonuclease site. For example, in a specific embodiment, GAPD competitive templates were prepared that separate from native GAPD on the basis of EcoRI or BamHI digestion. Separation on the basis of other restriction endonuclease digestion may also be used. Further, in some embodiments, the same recognition site can be used for both the reference nucleic acid(s) and one or more target nucleic acids, e.g., one or more nucleic acid tags.

In addition, in some embodiments, the length of the amplified product after restriction endonuclease digestion is a factor to be considered. For example, in certain embodiments, greater nucleic acid size differences are preferred for adequate separation on agarose gels, e.g., preferably about 40, about 50, about 80, about 100 or about 120 base pair differences.

Separated products may be quantified by any methods known in the art and/or described herein, including, for example, use of radiolabled probes, autoradiography, and preferably by spectrophotometry and/or densitometry, e.g., densitometry of ethidium bromide stained gels. Other methods that may be used to quantify amplified product include chromatography, e.g., high-performance liquid chromatography (HPLC); gas chromatography; and/or mass spectrometry, e.g., matrix-assisted laser desorption ionization-time-of-flight mass spectrometry (MALDI-TOF-MS) (An economic forecast for the gene expression market http://www.research-andmarkets.com/reports/5545).

In some embodiments, amplified products are measured using hybridizations, e.g., solid-phase hybridizations. Some embodiments, for example, comprise use of an array, including microbeads and/or microarrays. Arrays can include, for example, oligonucleotide arrays, including cDNA, DNA, and/or RNA oligonucleotide arrays. Such arrays may comprise a macroarray, a microarray (e.g., a microfluidic array), and/or a nanoarray. In some embodiments, the amplified product and/or the oligonucleotide hybridizing thereto may be labeled, e.g., with a detectable moiety. For example, one or more of the nucleotides in the amplification reaction may be labeled with a detectable moiety, e.g, introduced during a polymerization reaction. Detectable moieties that can be used include fluorescent moieties (e.g., fluorescein and its derivatives, e.g., fluorescein isothiocyanate, Rhodamin, Texas Red, tetramethylrhodamine, eosins and erythrosins, coumarin and its derivatives, e.g. 7-amino-4-methylcocumarin, aminocoumarin, bodipy dyes, such as Bodipy FL, cascade blue, Oregon green, cyanine dyes, e.g. Cy3 and Cy5, macrocyclic chelates of lanthanide ions, e.g. quantum day, fluorescent energy transfer dyes, such as thiazole orange-ethidium heterodimer, TOTAB, and the like), radioactive moieties (e.g., $^{32}P$, $^{33}P$, $^{35}S$, $^{125}I$, $^{14}C$, $^{3}H$, etc); chromophore moieties (e.g., ruthenium derivatives which intercalate into nucleic acids), electron-based moieties, biotinylated moieties, quantum dots, affinity labeled probes (biotin, avidin and/or streptavidin) and/or chemi- and/or photo-luminescent systems (e.g, PCR-ELISA). Niemeyer, Tech Note 5(35). Detectable moieties can also be detected through coupling with an enzyme, antibody, or other binding ligand, such as hydrolases, lyases, oxidoreductases, transferases, isomerases, ligases, peroxidase, glucose oxidase, phosphoatase, esterase and glycosidase. Specific examples include, for example, alkaline phosphatase, horse-radish peroxidase, lipases, beta-galactosidase, porcine liver esterase and the like.

In some embodiments, arrays for use in the practice of the present invention comprise oligonucleotides immobilized on a substrate where a first set of the immobilized oligonucleotides can bind to a sequence of the amplified product of a nucleic acid that is not common to the amplified product of the competitive template for the nucleic acid and where a second set of the immobilized oligonucleotides can bind to a sequence of the amplified product of the competitive template of the nucleic acid that is not common to the amplified product of the nucleic acid, for example, sequences that span the juncture between the 5' end of the competitive template and the truncated, mis-aligned 3' end of the competitive template (e.g., that can be prepared according to the method of Celi et al., supra, (1993)). Amplified product of the nucleic acid and of the competitive template for the nucleic acid can be allowed to bind to the array and, after, e.g., washing to remove unbound material, a ratio obtained from the two sets. The two sets of probes may be distinguishably labeled, e.g., using two fluors, such as Cy3 and Cy5, where a Cy3/Cy5 ratio can be obtained. In still some embodiments, methods of the instant invention can be practiced without the use of arrays.

Several types of nucleic acid array based detection methods can be employed, for example, such as flat array, suspension beads array, optical fiber bundler array, e-Sensor, and others (Schena, M., DNA Microarrays, Oxford University press, 2001). An array made from various methods and materials can be used, e.g., as described in Ramsay, *Nature Biotechnol.* 16:40-44, (1998); Okamoto, et al., *Nature Biotechnol.* 18:438-441, (2000); or as provided by commercial vendors, such as Affymetrix (Santa Clara, Calif.), Motorola (Phoenix, Ark.), Mergen (San Leandro), Rosetta pharmaceuticals (Seattle, Wash.), Qiagen (Alameda, Calif.), Corning (Corning, N.Y.), NEN PerkinElmer Life Sciences (Boston, Mass.), Hyseq (Sunnyvale, Calif.), Luminex (Austin, Tex.), and Illumina (San Diego, Calif.).

For isotope labeled amplified product, radioactivity can be determined by autoradiography or by a phosphorImager. The signal intensity reflects the amount of product. For fluorophore-labeled amplified product, fluorescence intensity can be detected by a fluorescence detector, such as an array scanner available from Affymetrix (Sunnyvale, Calif.) or from Axon Instruments Inc. (Union City, Calif.). Where amplified product is labeled with a moiety for detection, such as biotin or digoxin (DIG), or a moiety that can couple with an enzymatic reaction such as horse radish peroxidase (HRP) and alkaline phosphatase (AP), for example, the enzyme activity can be determined by measuring a chemiluminescent, colormetric, and/or fluorescence signal that generates from a substrate reaction catalyzed by the enzymes.

In some embodiments, amplified products are detected and/or quantified by nucleotide sequence analysis, e.g., by various techniques known in the art.

Methods taught herein can also be applied to other immunoassays known in the art, including, e.g., Western blots, 2D gel electrophoresis, antibody arrays or immunoarrays, immuno-precipitation following radioactive isotope labeling, immunohistochemistry, HPLC, GC/MS, MS/MS, MALDI-TOF mass spectrometry (see, e.g., Villanueva et al., *Anal. Chem.* 76(6), 1560-1570 (2004)), and/or SELDI-TOF (see, e.g., Petricoin et al., *Curr. Opin. Biotechnol.* 15(1), 24-30 (2004)). Methods taught herein can also be practiced with additional variations, modifications or adaptations, e.g., as provided below.

In some embodiments, one or more steps of the methods provided herein may be computer-implemented. For example, after sufficient gel electrophoresis, gels can be digitally imaged automatically, and the image analyzed automatically to assess amounts of amplified product, e.g., by automatically determining area under the curves. For example, software can determine area under the curves for the NT and CT of a given nucleic acid and calculate the ratio of NT/CT. In some embodiments, calculation steps are incorporated into a spreadsheet. For example, in some embodiments, a user can enter raw values (e.g., for peak heights or area under the curve) for the different amplified products into a spreadsheet, and the numerical value for an analyte can be automatically calculated. In some embodiments, software can be used to automatically enter values for amplified products into a spreadsheet to automatically calculate a numerical value, e.g., a numerical value corresponding to analyte abundance.

In some embodiments, one or more steps may be automated, e.g., 96- and/or 348 well plates can be used for automated assays, comprising, e.g., robotic workstations and/or plate readers.

Another aspect of the present invention is directed to a computer program for implementing certain embodiments of methods of the instant invention. In certain embodiments, the computer program includes a computer readable medium and instructions, stored on the computer readable medium. In preferred embodiments, the instructions include one or more steps recited above, including receiving data generated from one or more methods described herein. The computer program can further include instructions for dispensing amplified product into arrays for measurement, as well as instructions for fluorescently labeling amplified product and/or nucleic acid to which they hybridize. Amplified product may be labeled, e.g., by labeling one or more nucleotides in the amplification reaction with a detectable moiety, e.g. a fluorescent moiety. The computer program can further include instructions for measuring amounts of nucleic acid, e.g., by comparing fluorescent intensities of the arrays for the amplified product of a given nucleic acid and its competitive template.

Another aspect of the present invention is directed to an apparatus for carrying out certain embodiments of the methods of the instant invention. For example, the apparatus may comprise suitable means for carrying out one or more steps recited above. Means can include any suitable devices capable of achieving (or approximately achieving) the desired result for a particular step being carried out.

B. Two-Step Adaptation

In some embodiments, methods of the instant invention further comprise two rounds of amplification. For example, methods for assaying an analyte can comprise co-amplifying target nucleic acids, with their corresponding competitive templates, as described above, to produce first amplified products thereof. In a two-step adaptation, first amplified products can be diluted and then further co-amplified, e.g., to produce second amplified products thereof. Amplifying and then further amplifying a nucleic acid and its competitive template may be considered as two rounds of amplification, and a process employing two rounds of amplification may be referred to as a "two-step" process or "two-step" adaptation.

Diluting amplified product may be achieved by any techniques known in the art and/or described herein. For example, diluting may involve removal of an aliquot of a mixture comprising first amplified product, and transfer to a vessel containing additional buffer. In some embodiments, diluting produces at least about a 1,000,000-fold dilution, at least about a 500,000-fold dilution, at least about a 100,000-fold dilution, at least about a 50,000-fold dilution, at least about a 10,000-fold dilution, at least about a 5,000-fold dilution, at least about a 1,000-fold dilution, at least about a 500-fold dilution, or at least about a 100-fold dilution.

Diluted amplified products (obtained in round one) are further amplified in round two. In some embodiments, diluted amplified product of a target nucleic acid and its corresponding competitive template may be further co-amplified in a second round of amplification. For example, diluted amplified product of a nucleic acid tag and its corresponding competitive template may be further co-amplified in a second round of amplification. In some embodiments, diluted amplified product of a reference nucleic acid and its corresponding competitive template may be further co-amplified in a second round of amplification. In preferred embodiments, round two uses at least one primer pair used in round one. Further, some embodiments do not use nested primer pairs for the further round(s) of amplification.

In some embodiments, amplified products are subjected to more than two rounds of amplification. Where the "two-step" approach is extended for more than two rounds of amplification, second amplified product of a nucleic acid and of a competitive template for the nucleic acid can be diluted and still further amplified, e.g., to produce third amplified product thereof. For example, second amplified product of a nucleic acid tag and its corresponding competitive template may be again diluted and further amplified and/or second amplified product of a reference nucleic acid and its corresponding competitive template may be again diluted and further amplified. The steps of diluting and further amplifying may be repeated at least about once, at least about twice, at least about 3 times, at least about 5 times, at least about 10 times, at least about 20 times, at least about 50 times, at least about 100 times or more.

Various nucleic acids and corresponding competitive templates may be amplified in a given vessel during round one, round two and/or further round(s). For example, in some embodiments, more than one nucleic acid (each with its corresponding competitive template) are co-amplified in a given vessel. In some embodiment, repeat amplifications are carried out with fewer different nucleic acids (each with its corresponding competitive template) in a given vessel. For example, in some preferred embodiments, amplified products are further amplified with primers for a nucleic acid representing one analyte. For example, co-amplifying diluted first amplified product of a nucleic acid and of the competitive template for the nucleic acid can be achieved by using a primer pair for co-amplifying the particular nucleic acid and its corresponding competitive template dried onto the vessel used in round two. For example, primers for nucleic acids corresponding to individual analytes can be aliquotted into individual reaction vessels and dried down, e.g., on 384-well plates. Multiple plates loaded with primers (e.g., about 10, about 100, about 500 plates) can be prepared in advance. For example, in some embodiments, primers prepared this way are stable at 4° C. for months.

In a two-step adaptation, amplified product obtained after the first or second (or higher) round may be used in the comparisons described above. For example, in some embodiments, a first relation is obtained comparing second amplified product of a target nucleic acid to second amplified product of its competitive template; a second relation is obtained comparing first amplified product of reference nucleic acid to first amplified product of its competitive template; and the first and second relations are compared. In more preferred embodiments, the relation obtained by comparing the first and second relations remains substantially constant beyond the exponential phase of amplification of one or more of the nucleic acids amplified. Substantially constant can refer to variations of +/−about 1%, about 5%, about 10%, about 15%, or about 20% of an absolute constant number.

As mentioned above, in some embodiments, a two-step adaptation may comprise two step amplification of the nucleic acid serving as a reference nucleic acid. In some such embodiments, a fourth relation may be obtained comparing second amplified product of the reference nucleic acid to second amplified product of its competitive template. In some embodiments, the first and fourth relations are compared. In still some embodiments, where the nucleic acid serving as a reference nucleic acid is amplified in two rounds, first amplified product of a target nucleic acid and first amplified product of its competitive template can be used to obtain the first relation.

The use of two rounds can lower the threshold amount of nucleic acid that can be measured, thereby lowering the threshold amount of an analyte that can be detected and/or quantitated in a sample. The lower threshold of detection can be defined as the minimum amount of analyte that can be reliably detected above background. The detection limit can be defined as the lowest concentration or quantity of analyte that can be detected with reasonable certainty. Without being limited to a particular hypothesis and/or theory, there may be a minimum amount of nucleic acid that can be used to achieve a statistically significant measurement. The minimal amount of nucleic acid used in an amplification reaction can correspond to, e.g., a minimal amount of nucleic acid tag or a minimal amount of nucleic acid analyte. For analyte present in cells, the lower threshold of detection may be considered in terms the minimal number of cells.

Figure 3:
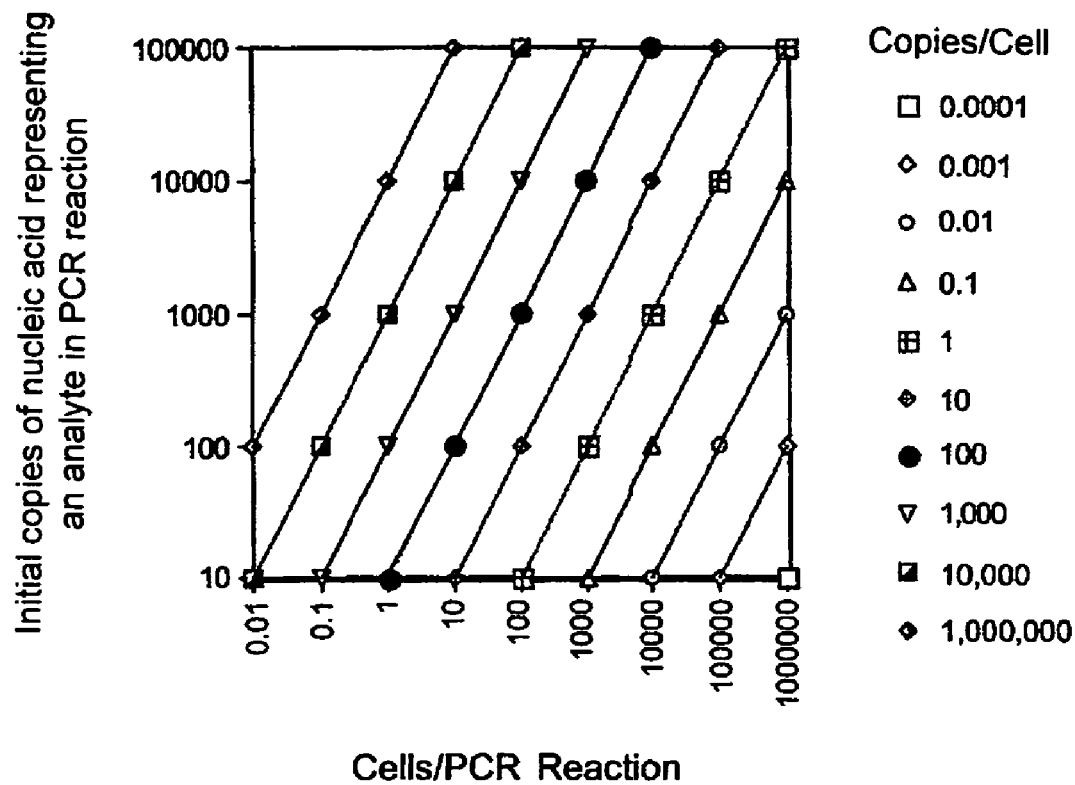
FIG. 3 illustrates how the amount of nucleic acid representing an analyte in a PCR reaction has a direct relationship to the number of copies of analyte/cell that can be measured for a given number of cells.

FIG. 3 schematically illustrates how the amount of nucleic acid representing an analyte in a PCR reaction has a direct relationship to the number of copies of analyte/cell that can be measured for a given number of cells. The minimal number of cells then depends on the number of copies/cell. For nucleic acid analytes comprising RNA, e.g., the minimal number of cells also depends on the efficiency of RNA extraction and/or reverse transcription. For example, consider the number of cells to provide RNA sufficient to result in at least about 10 molecules of cDNA for a particular gene. It generally is assumed that RNA extraction is close to about 100% whereas reverse transcription is about 10% efficient. Thus, if a homogeneous population of cells is studied and each cell contains about 10 copies of mRNA for a gene, 1 copy per cell will remain after reverse transcription. Due to stoichiometric considerations, cDNA samples included in a PCR reaction that contain less than about 10 molecules of a transcript is questionable, in some types of PCR. In such embodiments, cDNA representing about 10 cells is preferably present in the PCR reaction, as illustrated in FIG. 3. If a heterogeneous cell population is studied in which 1 cell out of 10 expresses a particular transcript, cDNA representing about 1,000 cells is preferably present in the PCR reaction. For non-nucleic acid analytes, the minimal number of cells can depend on the efficiency of extraction and/or of tagging analyte with its nucleic acid tag, and analogous statistics may apply.

In certain embodiments, the use of two rounds can overcome some of the limitations illustrated in FIG. 3. Consider a typical about 10 µl cDNA sample representing about 1,000 cells and comprising about $6 \times 10^5$ molecules of β-actin nucleic acid. Genes expressed at the mean level (100-fold lower than β-actin), are represented by about 6,000 molecules in the sample. A number of genes that may be important functionally are expressed about 10,000-fold lower than β-actin, and for such genes there would be about 60 molecules represented in the sample. In a 100-fold smaller sample of about 100 nanoliters, genes expressed about 10,000-fold lower than β-actin would be represented by about 0.6 copies or fewer. In certain embodiments of the instant invention using the two-step adaptation, about 10 nanoliters of an about 10 µl round one amplified product may be used in a round two reaction volume of about 100 nanoliters. Because more than about 1,000,000-fold amplification is routinely achieved in the round one reaction, about 10 nanoliters of the about 10 µl round one reaction will contain ample amplified product of nucleic acid and competitive template to be measured with statistical confidence after round two. The same reasoning can apply to a non-nucleic acid analyte, represented in a PCR reaction by a corresponding number of nucleic acid tags.

Accordingly, in some preferred embodiments, the use of two rounds can increase the number of measurements obtainable from a small sample of analytes. For example, in some embodiments, at least about 10,000, at least about 50,000, at least at about 80,000, at least about 100,000, at least about 150,000 measurements can be obtained from the same amount of starting material typically used to obtain one measurement using the processes provided in Willey and Willey et al. (U.S. Pat. Nos. 5,639,606, 5,643,765, and 5876978). In some embodiments, at least about 200,000, at least about 500,000, at least at about 800,000, at least about 1,000,000, or at least about 1,500,000 measurements can be obtained from the same amount of starting material typically used to obtain one measurement using the processes provided in Willey and Willey et al. (U.S. Pat. Nos. 5,639,606, 5,643,765, and 5876978), preferably without loss of sensitivity to detect rare transcripts or other low abundance analytes.

Further, in some embodiments, use of two rounds can increase the number of analytes that can be measured in a given sample. For example, in some embodiments, sufficient amplified product can be generated to measure several different analytes in about 100 to about 1,000 cell samples. To compare, using the processes provided in Willey and Willey et al. (U.S. Pat. Nos. 5,639,606, 5,643,765, and 5,876,978), cDNA representing about 100 to about 1,000 cells is typically used to measure one nucleic acid in one PCR reaction. Referring again to FIG. 3, using this amount allows detection of analytes that occur at about 0.1 to about 1 copy per cell (or about 1 to about 10 copies per 10 cells) with statistical significance. For nucleic acid analyte represented by cDNA, the same amount of cDNA can be used in a first round of amplification in certain embodiments of the instant invention. Since this cDNA is co-amplified with its competitive template, and since the relationship of endogenous cDNA to its competitive template remains constant or substantially constant, amplified product from round one can be diluted and further amplified in a second round with primers specific to a given nucleic acid without significantly changing the relative amounts of amplified products. The same applies to non-nucleic acid analyte, represented in a PCR reaction by a corresponding number of nucleic acid tags. Some embodiments, for example, allow replicate measurement of many different analytes from small amounts of specimen material.

The practice of some embodiments of the present invention permits low abundance analytes to be measured with statistical significance. For example, in some embodiments, the number of copies of a nucleic acid corresponding to a gene transcript can be determined, e.g., the number of copies/cell, where the gene is expressed in low copy number. In some embodiments, the number of copies of nucleic acid representing a non-nucleic acid analyte can be determined, e.g., the antigen copy number, where analyte abundance is low.

In some embodiments, methods of the instant invention are capable of detecting and/or quantifying less than about 10 copies/cell of at least about 100 different analytes in a small biological specimen, from the amount of material typically used to obtain one measurement. In some embodiments, enumerating less than about 10,000 molecules, less than about 1,000 molecules, or less than about 100 molecules can allow measurement of less than about 10 copies/cell of at least about 100 different analytes in a small biological specimen, e.g., from the amount of material typically used to obtain one measurement, e.g., to measure that few copies of an analyte. In still some embodiments, more measurements can be obtained from a given specimen and/or sample, e.g., of the size typically used to measure that few copies of one analyte. For example, practice of some embodiments of the invention disclosed herein can detect and/or quantify less than about 100, less than about 50, less than about 20, less than about 10, less than about 8, or less than about 5 copies/cell of at least about 20, at least about 50, at least about 80, at least about 100, at least about 120, at least about 150, or at least about 200 different analytes in a sample.

In some embodiments, the specimen collected may comprise less than about 100,000 cells, less than about 10,000 cells, less than about 5,000 cells, less than about 1,000 cells, less than about 500 cells, less than about 100 cells, less than about 50 cells, or less than about 10 cells. In some embodiments, methods of the present invention are capable of assessing the amount of an analyte present in a sample comprising less than about 100,000 cells. For example, a sample from a biopsy may comprise less than about 100,000 cells. In some embodiments, the method is capable of assessing the amount of an analyte in less than about 10,000 cells, less than about 5,000 cells, less than about 1,000 cells, less than about 500 cells, less than about 100 cells, less than about 50 cells, or less than about 10 cells. Small biological specimen can also refer to amounts typically collected in biopsies, e.g, endoscopic biopsies (using brush and/or forceps), needle aspirate biopsies (including fine needle aspirate biopsies), as well as amounts provided in sorted cell populations (e.g., flow-sorted cell populations) and/or micro-dissected materials (e.g., laser captured micro-dissected tissues). For example, biopsies of suspected cancerous lesions in the lung, breast, prostate, thyroid, and pancreas, commonly are done by fine needle aspirate (FNA) biopsy, bone marrow is also obtained by biopsy, and tissues of the brain, developing embryo, and animal models may be obtained by laser captured micro-dissected samples.

C. Substantially Constant Relationship

Some embodiments of the present invention described above provide a relation for assaying analytes where the relation remains constant or substantially constant beyond the exponential phase of amplification. Substantially constant can refer to variations of +/−about 1%, about 5%, about 10%, about 15%, or about 20% of an absolute constant number.

In nucleic acid amplifications, e.g., PCR, the amount of amplified product can cease to increase exponentially after an indefinite number of cycles. For example, at some point and for uncertain reasons, the amplification reaction can become limited and the amount of amplified product can increase at an unknown and/or non-exponential rate. For example, PCR amplification rate can be low in early cycles when the concentration of the templates is low. After an unpredictable number of cycles, the reaction can enter a log-linear amplification phase. In late cycles, the rate of amplification can slow as the concentration of PCR products becomes higher, e.g., high enough to compete with primers for binding to templates. The yield of amplified product in PCR reactions, for example, has been reported to vary by as much as 6-fold between identical samples run simultaneously. Gilliland et al., supra, (1990). PCR techniques are generally described in U.S. Pat. Nos. 4,683,195; 4,683,202; and 4,965,188. Other investigators have analyzed samples amplified for a number of cycles known to provide exponential amplification (Horikoshi et al., *Cancer Res.* 52:108-116 (1992); Noonan et al., *Proc. Natl. Acad. Sci. USA* 87:7160-7164 (1990); Murphy et al., *Biochemistry* 29:10351-10356 (1990); Carre et al., *J. Clin. Invest.* 88:1802-1810 (1991); Chelly et al., *Eur. J. Biochem* 187:691-698 (1990); Abbs et al., *J. Med. Genet.* 29:191-196 (1992); Feldman et al., *Circulation* 83:1866-1872 (1991). Some embodiments of the instant invention allow quantification of PCR amplification at any phase in the PCR process, including the plateau phase, e.g., using products obtained from beyond the exponential phase.

Some embodiments of the present invention relate to obtaining a constant (or substantially constant) relation beyond the exponential phase of nucleic acid amplification, thereby allowing the initial amount of a nucleic acid to be determined by extrapolation from end point amounts of amplified product. In some embodiments, the exponential phase for amplifying the nucleic acid need not be defined for each set of experimental conditions, saving time and materials. For example, some embodiments do not involve real-time measurements. Some embodiments do not involve generation of a standard curve, and/or generation of multiple standard curves, e.g., where the standard curve is used to determine an exponential range of amplification for a given nucleic acid to be measured and/or where the standard curves compare measured amounts of one nucleic acid to another.

D. Sensitivity

Some embodiments of the present invention described above provide a relation for assaying analytes where the relation provides a desired sensitivity. Sensitivity can be defined as the ability of a procedure to produce a change in signal for a defined changed in the quantity of analyte, i.e., the slope of a calibration curve. Some embodiments of the instant invention provide a slope greater than about 0.1, greater than about 0.2, greater than about 0.5, or greater than about 0.8. Some preferred embodiments of the instant invention provide a slope of about 1/1. Some embodiments provide at least about 80%, at least about 90%, at least about 95% or about 100% sensitivity.

For example, some embodiments of the instant invention provide a relation capable of detecting less than about a two-fold difference, less than about a one-fold difference, less than about an 80% difference, less than about a 50% difference, less than about a 30% difference, less than about a 20% difference, less than about a 10% difference, less than about a 5% difference, or less than about a 1% difference. Such sensitivities can correspond to identifying small changes in the presence of an analyte.

In some embodiments one or more of these differences can be detected in about 1,000 molecules or less of an analyte in a sample, e.g., in about 800, in about 600, or in about 400 molecules. In some embodiments, one or more of these differences can be detected in about 100 molecules or less (e.g., in about 60 molecules), in about 10 molecules or less (e.g., in about 6 molecules), or in about 1 molecule or less of an analyte in a sample. In some embodiments, one or more of these differences can be detected in less than about 10,000,000, less than about 5,000,000, less than about 1,000,000, less than about 500,000, less than about 100,000, less than about 50,000, less than about 10,000, less than about 8,000, less than about 6,000, less than about 5,000, or less than about 4,000 molecules of an analyte in a sample.

Some embodiments, as described above, assay analytes, including non-nucleic acid analytes, over a range of concentrations, e.g., assaying analyte abundance over one or more orders of magnitude, e.g., at least about one, at least about 2, at least about 3, at least about 4, at least about 5, at least about 6, or at least about 7 orders of magnitude. In some such embodiments, the assay detects less than about a two-fold difference over the range. In some embodiments, the assay detects less than about a one-fold difference, less than about an 80% difference, less than about a 50% difference, less than about a 30% difference, less than about a 20% difference, less than about a 10% difference, less than about a 5% difference, or less than about a 1% difference over the range. Sensitivities described herein can be achieved by some of the embodiments of the instant invention.

E. Reproducibility

In preferred embodiments, methods and/or compositions for assaying an analyte are reproducible. Some embodiments, for example, provide a coefficient of variation of less than about 25% between samples. In some embodiments, the coefficient of variation is less than about 50%, less than about 30%, less than about 25%, less than about 20%, less than about 15%, less than about 10%, less than about 5%, or less than about 1% between 2 of more samples of an analyte. Such coefficients of variation can apply to over one or more orders of magnitude, e.g., at least about one, at least about 2, at least about 3, at least about 4, at least about 5, at least about 6, or at least about 7 orders of magnitude.

Such coefficients of variation can be obtained in some embodiments where the 2 samples are assayed at different times, e.g., on different days; in the same or different experiments in the same laboratory; and/or in different experiments in different laboratories; and/or where the samples are obtained from different sources, e.g., different subjects and/or different species. Preferred embodiments of the present invention provide both intra- and inter-laboratory reproducibility (Vondracek et al., *Int. J. Cancer* 99, 776-782 (2002)) that is sufficient to detect less than two-fold differences in analyte abundance. For example, in some embodiments, inter-laboratory correlation of variance was 0.48, e.g., from gene expression measurements using a A549 cDNA sample taken in different laboratories at different times, spanning nearly one year. In some embodiments, e.g., embodiments using micro-channel capillary electrophoreseis, the correlation of variance was reduced to 0.26. Additional details of a study to evaluate reproducibility are provided in Example III below.

In some embodiments, methods and/or compositions for assaying analytes are robust. Robust as used herein, and its grammatical variations, can refer to the applicability of a method and/or composition to various types of samples, presenting various environments and/or conditions, e.g., in terms of pH, ionic strength, osmolarity, complexity. For example, in preferred embodiments, methods and/or compositions provided herein can be used with complex samples, as well as with purer solutions. Complex sample or mixture as used herein can refer to a sample or mixture comprising multiple macromolecules, e.g., protein-rich samples such as blood samples that contain multiple types of proteins. Robustness can also be used interchangeably herein with ruggedness.

In some embodiments, reproducibility between samples allows for the use of fewer dilution tubes. In some embodiments, a single tube may be used, simplifying procedures and permitting the evaluation of many different samples at one time.

In some embodiments, including competitive template internal standards in a common standardized mixture used in different measurements can control for one or more sources of variation. Sources of variation include, e.g., variation from loading, intra-nucleic acid amplification efficiency, inter-nucleic acid amplification efficiency, inter-specimen amplification efficiency, inter-sample amplification efficiency, and/or intra-sample amplification efficiency. For example, some embodiments using an Agilent 2100 Bioanalyzer provide reproducibility intra-lab CV of less thanabout 0.25 routinely, with a sensitivity comparable to slab gel electrophoresis.

Table I tabulates a number of sources of variation and control methods.

| Source of Variation | Embodiments of methods described herein Real-time |
|---|---|
| Loading: Due to variation in pipetting, quantification, reverse transcription. Consequence: unreliable comparison of abundance of same analyte in two different samples | Multiplex Amplify with Reference Analyte (e.g. β-actin) Multiplex Amplify with Reference Gene (e.g. β-actin) |
| Intra-nucleic acid Amplification Efficiency | |

| Source of Variation | Embodiments of methods described herein Real-time |
|---|---|
| Cycle-to-Cycle Variation: early slow, log-linear, and late slow plateau phases Consequence: unreliable comparison of abundance of same analyte in different samples | Internal standard CT for each analyte in a Standardized Mixture of Internal Standards (SMIS) Real-time measurement |
| Inter-nucleic acid Amplification Efficiency: in efficiency of primers Consequence: unreliable comparison of abundance of different analytes in the same or different samples | Internal standard CT for each analyte in a SMIS External standard curve for each gene measured |
| Inter-specimen Amplification Efficiency: variable presence of an inhibitor of PCR Consequence: unreliable comparison of abundance of same or different analyte in same or different samples | Internal standard CT for each analyte in a SMIS Standard curve of reference sample compared to test sample |
| Inter-sample Amplification Efficiency: in quality and/or concentration of PCR reagents (e.g. primers); in presence of an inhibitor of PCR Consequence: unreliable comparison of abundance of same or different analytes in same or different samples | Internal standard CT for each analyte in a SMIS None |
| Intra-sample Amplification Efficiency: in thermocycler efficiency Consequence: e.g., unreliable comparison of abundance of same or different analyte in same or different samples | Internal standard CT for each analyte None |

Variation in loading may result from variation in pipetting, aliquoting, quantification, and/or reverse transcription of mRNA analytes. For example, errors may occur when aliquotting RNA material into vessels for performing reverse transcription. Although reverse transcription efficiency can vary from one sample to another, the representation of one nucleic acid to another in a sample need not vary among different reverse transcriptions.

For example, the efficiency of reverse transcription can vary from about 5 to about 90% (Simmonds et al, 1990). Variation in reverse transcription efficiency, however, may affect different transcripts in the same or substantially the same manner (Willey et al., supra, (1998); Loitsch et al., *Clin. Chem.* 45, 619-624 (1999)). In one experiment, for example, gene expression was measured in 5 different reverse transcriptions of a given sample of RNA from the SW900 non-small cell carcinoma cell line. The mean level of expression obtained was 3,600 molecules/$10^{-6}$ β-actin molecules with a CV of 0.26, no greater than if replicate measurements had been made on cDNA resulting from a single reverse transcription. However, if reverse transcription and amplification reactions are carried out in different vessels, errors may occur when pipetting cDNA from the reverse transcription reaction into individual PCR reaction vessels. That is, without being limited to a particular theory and/or hypothesis, the effect of variation in reverse transcription can be the same as if different levels of cDNA were loaded in a PCR reaction. Controlling for cDNA loading can then control variation in reverse transcription efficiency.

Variation in intra-nucleic acid amplification efficiency may result from, e.g., cycle-to-cycle variation, e.g., where different amplification cycles show various early slow, log-linear and/or late slow plateau phases, as described above. Where gene expression is being measured, intra-nucleic acid amplification efficiency can refer to intra-gene amplification efficiency, i.e., for example, variation in repeat amplifications of cDNA corresponding to a given gene. Where non-nucleic acid analytes are being measured, intra-nucleic acid amplification efficiency can refer to intra-tag amplification efficiency, i.e., for example, variation in repeat amplifications of a nucleic acid tag representing a given analyte.

Variation in inter-nucleic acid amplification efficiency can refer to inter-gene amplification efficiency, e.g., where the efficiency at which a given gene is amplified differs from that at which a different gene is amplified, or it can refer to inter-tag amplification efficiency, e.g., where the efficiency at which a given nucleic acid tag is amplified differs from that at which a different nucleic acid tag is amplified. Such differences may be caused by, e.g., differences in the primers used for amplifying the different nucleic acids measured in the same and/or different samples. For example, the efficiency of a pair of primers, e.g., as defined by lower detection threshold (LDT), may not be predictable, and may vary more than about 100,000-fold (from less than about 10 molecules to about $10^6$ molecules) in some embodiments.

Also, a bad lot (e.g., where degradation of primers and/or competitive templates has occurred) or inappropriate concentration of primers would cause variation in PCR amplification of one nucleic acid relative to another. In some embodiments, the concentration of competitive template is small (e.g., femptomolar range) so that any change in the number of molecules present in the reaction may introduce a large source of error. Presence of an inhibitor could alter PCR amplification efficiency of one nucleic acid, e.g., one gene or one nucleic acid tag, compared to another.

Variation in inter-specimen amplification efficiency may be caused by, e.g., variable presence of an inhibitor (e.g., an inhibitor of PCR) in different specimen. PCR reactions inhibitors, include, e.g., heme. Akane et al., *J. Forensic Sci.* 39, 362 372 (1994); Zhu et al., *DNA Cell Biol.* 21, 333 346 (2002). Further, amplification efficiency for different genes (or different tags) may be affected to different degrees in different samples and/or specimen. Meijerink et al., *J. Mol. Diagn.* 3, 55-61 (2001); Giulietti et al., *Methods* 25, 386-401 (2001). Such differences may result in variation in measuring the same or different nucleic acids (e.g., the same or different genes or the same or different nucleic acid tags) in the same or different specimen and/or samples. For example, a given PCR inhibitor may have little effect on amplification of a lowly expressed gene, e.g., GSTM3. The same PCR inhibitor may have a larger effect, e.g., a significantly larger effect, on amplification of a more-highly expressed gene, e.g., ERBB2, including, e.g., preventing amplification or reducing amplification to non-detectable levels.

Variation in inter-sample amplification can refer to inter-reaction variation or well-to-well variation in repeat measurements of the same or different nucleic acids (e.g., the same or different genes or the same or different nucleic acid tags) in the same or different samples and/or specimen. Variation in inter-sample amplification efficiency can result from, for example, variable presence of an inhibitor (e.g., an inhibitor of PCR) in different reaction vessels, variation in temperature cycling between different region of a themocycler block, variable quality of one or more PCR reagents or variable concentrations of one or more PCR reagent (e.g., primers).

One or more of these sources of variation can reduce PCR amplification efficiency in a well to the point where no PCR product can be observed in that well. Some embodiments of the instant invention allow this type of error to be recognized, for example, embodiments using a standardized mixture comprising about $10^{-17}$ M competitive template for the nucleic acid sought to be amplified. In a 10 µL PCR reaction volume, about $10^{-17}$ M represents about 60 molecules. With about 60 molecules of internal standard present in the PCR reaction and components of the PCR reaction functioning properly, if a nucleic acid is not present in a sample, the amplified product for the competitive template will be observed, but the amplified product for the nucleic acid will not. This may indicate that there was less than about six molecules (about 10-fold less than the number of competitive template molecules) of nucleic acid in the reaction mixture. On the other hand, if neither amplified product of neither the nucleic acid nor its competitive template is detectable, it can be determined that the PCR reaction efficiency was suboptimal.

Variation in intra-sample amplification can refer to intra-reaction variation, e.g., variable amplification efficiency in a given reaction using a given sample. Variation in intra-sample amplification efficiency may result from, e.g., variation in thermocycler efficiency at various positions within a thermocycler, and can introduce variation when measuring amounts of the same or different nucleic acids (e.g., expression of the same or different genes or presence of the same or different nucleic acid tags) in the same or different samples and/or specimen.

Some embodiments for measuring nucleic acids control for variation caused by one or more of sources of variation selected from sample loading, intra-nucleic acid amplification efficiency, inter-nucleic acid amplification efficiency, inter-specimen amplification efficiency, inter-sample amplification efficiency, and intra-sample amplification efficiency. For example, in some embodiments, use of a standardized mixture and/or a series of serially-diluted standardized mixtures can provide control.

Some preferred embodiments control for one or more sources of variation without the use of real-time measurements obtained using kinetic analysis (e.g., real-time PRC measurements). For example, obtaining a "ratio of ratios" in some embodiments does not involve taking real-time measurements. Some preferred embodiments control for one or more of sources of variation without generating one or more standard curve(s). For example, obtaining a "ratio of ratios" in some embodiments does not involve generating a standard curve. In more preferred embodiments, one or more sources of error are controlled for using methods that do not involve real-time measurements nor generation of a standard curve. In even more preferred embodiments, two or more, three or more, four or more, five or more or six sources of variation are controlled for without real-time measurements nor generation of a standard curve.

Figure 4:
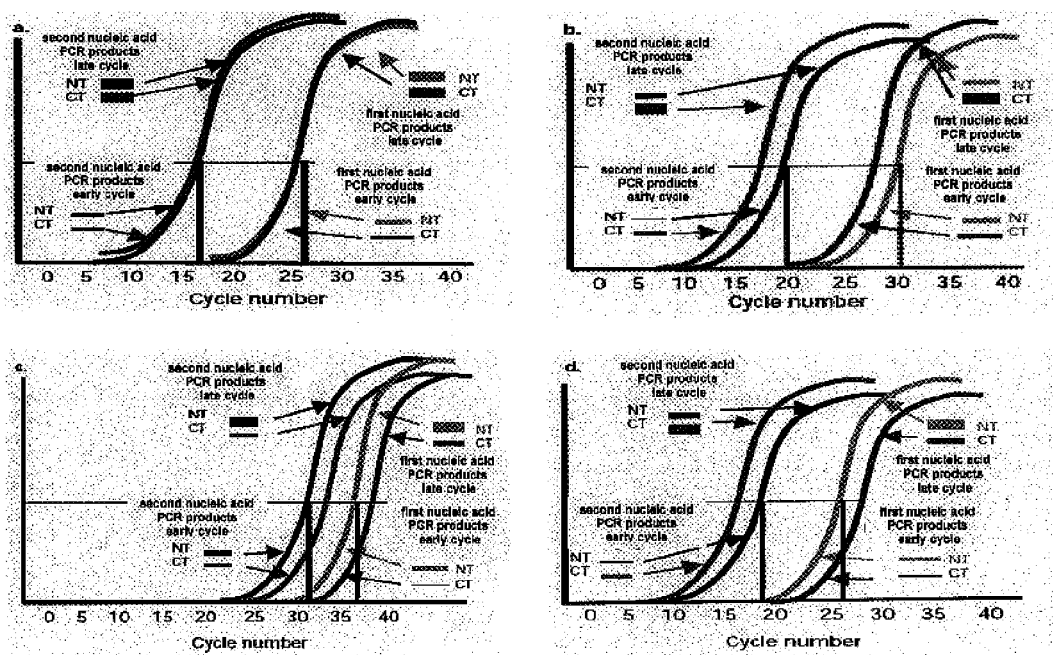
FIG. 4a illustrates an experiment using a first sample of a first specimen.
FIG. 4b further illustrates controls for loading from one sample to another.
FIG. 4c illustrates controls for loading and variation in amplification efficiency.
FIG. 4d further illustrates controls for loading a sample of a second specimen, where the first nucleic acid is present in a higher amount.

FIG. 4 illustrates the control of one or more of these sources of error in some embodiments compared to real-time RT-PCR in two different specimen in four different experiments. In FIG. 4, the nucleic acids being measured are referred to as native template (NT), the competitive template for each is referred to as CT, and the second nucleic acid serves as the reference nucleic acid. The nucleic acids being measured correspond to sample analyte, comprising either a nucleic acid analyte, a corresponding cDNA molecule, or a nucleic acid tag for a non-nucleic acid analyte.

FIG. 4 illustrates amplified product of native template and competitive template for a first and a second nucleic acid that are PCR-amplified simultaneously for an indicated number of cycles. The amplified products at endpoint are electrophoretically separated, e.g., in the presence of fluorescent intercalating dye, and quantified densitometrically. For example, dyes of the ethidium (e.g., ethidium bromide), furocomarins, phenothiasines, phenazines, and quinoline type can be used. In the illustrated embodiment, the shorter CT PCR product migrates faster than the NT PCR product, and is represented by a CT band below the NT band. As one of skill in the art will understand, if there is more NT product than CT product, the NT band will emit more fluorescent light; if there is more CT product than NT product, the CT band will emit more fluorescent light. In real-time, the fluorescent PCR product is measured at each of the 35 to 40 cycles. FIG. 4 illustrates how the reactions would look if measured at each cycle in real time and the CT for the real-time curve is represented by the perpendicular black line.

FIG. 4a illustrates that the ratio of NT/CT present at the beginning of PCR remains (substantially) constant throughout PCR to endpoint. As described above, it is not necessary to monitor the amplification reaction in real-time to ensure that the reaction is in log-linear phase in some embodiments of the instant invention.

FIG. 4a illustrates an experiment using a first sample of a first specimen. In the first sample, there are about equivalent number of molecules of the second nucleic acid NT and CT present at the beginning of the PCR reaction (e.g., described in more detail below, where a balanced sample dilution is used). Thus, following electrophoresis of the amplified product of the second nucleic acid, the NT and CT bands are about equivalent, and during real-time measurement, the fluorescent intensity for the NT will be about the same as for the CT. The NT/CT ratio is the same at an early cycle as it is at a late cycle (endpoint), even though the band intensity for both NT and CT is low at early cycle compared to late cycle. Similarly, the first nucleic acid NT band and CT band are about equivalent, and the real-time value for the NT is about the same as for the CT. The $\Delta C_T$ between the second and the first nucleic acid in real-time measurements is about 10.

FIG. 4b further illustrates controls for loading from one sample to another. In FIG. 4b, the first specimen is re-analyzed using a lower starting amount of nucleic acid, e.g., less cDNA loaded or less nucleic acid tag loaded, due to a variation in pipetting, e.g., in aliquoting a second sample of the first specimen into a different vessel. The NT/CT ratio for the second nucleic acid is lower. However, because the relative concentration of competitive templates is fixed and the relative representation of each nucleic acid is fixed, the NT/CT ratio for the first nucleic acid goes down commensurately. Accordingly, the "ratio of ratios" (odds ratio) of the first nucleic acid NT/CT divided by second nucleic acid NT/CT remains the same as in FIG. 4a. In this case, the $\Delta C_T$ in real-time analysis is also unchanged.

FIG. 4c illustrates controls for loading and variation in amplification efficiency. In FIG. 4c, the first specimen is again re-analyzed, but with both (1) a larger amount of cDNA or nucleic acid tag loaded due to variation in pipetting (leading to variation in starting amount of native template) and (2) lowered amplification efficiency of the second nucleic acid, as might be caused by inhibitor in the well that affects amplification of this nucleic acid more than the other, or inappropriate concentrations of primers for the second nucleic acid.

FIG. 4c illustrates that with real-time measurements, this reduces the $\Delta C_T$ from 10 to 6, and the value for the first nucleic acid is inappropriately high. In real-time measurements, the selective inhibition is associated with a decreased $\Delta_{CT}$ and erroneous measurement.

In contrast, using certain embodiments described herein, because the amplification efficiency of the NTs for each of the two nucleic acids is affected the same way as its corresponding CT, the NT/CT ratio is unchanged in FIGS. 4a and 4c for either first or second nucleic acid. Also, with the larger amount of nucleic acid loaded, the first nucleic acid NT/CT ratio and the second nucleic acid NT/CT ratio increase commensurately. Accordingly, the "ratio of ratios" (odds ratio) of first nucleic acid NT/CT divided by the second nucleic acid NT/CT stays the same between FIGS. 4a and 4c.

FIG. 4d further illustrates controls for loading a sample of a second specimen, where the first nucleic acid is present in a higher amount. Although, the first nucleic acid is more abundant compared to the second nucleic acid, real-time measurements give a $\Delta C_T$ of about 7. In contrast, using certain embodiments of described herein, the ratio of ratios indicates the higher abundance. As less nucleic acid is loaded into the PCR reaction, there are fewer copies of the second nucleic acid NT than CT copies present at the beginning of the PCR reaction compared with FIG. 4a. Throughout real-time measurement, the fluorescence value of the NT is less than that of the CT and at the end of PCR, the second nucleic acid NT band is still less than the CT band. However, even though less nucleic acid was loaded into the PCR reaction compared to the first sample, the first nucleic acid NT band is more dense than the first nucleic acid CT band due to its higher abundance, and the first nucleic acid NT fluorescence value during real-time measurement is higher throughout PCR. Accordingly, the "ratio of ratios" (odds ratio) of first nucleic acid NT/CT divided by the second nucleic acid NT/CT provides a higher value in FIG. 4d than in FIG. 4a.

Thus real-time RT-PCR may control for loading by measuring the first and second nucleic acids in the same PCR reaction (FIGS. 4a, 4b, 4d). The CT (for each nucleic acid represented by a black line intersecting with the X axis) for the first and second nucleic acids both could vary from one experiment to another, but the $\Delta C_T$ does not vary. However, real-time does not control for variation in the presence of inhibitors, or the quality of PCR reagents.

E. Accuracy

In some embodiments, methods and/or compositions of the instant invention can control for one or more of such sources of variation. In some embodiments, methods and/or compositions of the instant invention can reduce false negatives and/or false positives for a given analyte. In preferred embodiments, false negatives and/or false positives may be reduced to a statistically insignificant number. In even more preferred embodiments, methods provided herein can eliminate false negatives and/or false positives. In some embodiments quality control is facilitated by the simultaneous presence of an internal standard for each analyte being assayed and the simultaneous presence of an internal standard for a reference analyte for each reaction (that can control for loading). For example, there may be no false negatives and a statistically insignificant number of false positives in some preferred embodiments.

II. Compositions for Assaying Analytes and Preparation Thereof

Another aspect of the instant invention relates to compositions for assaying nucleic acid and/or non-nucleic acid analytes in a sample, and methods for preparing such compositions.

A. Standardized Mixtures

Some embodiments of the instant invention provide standardized mixtures of reagents for use in assaying analytes, e.g., as discussed above.

Figure 5:
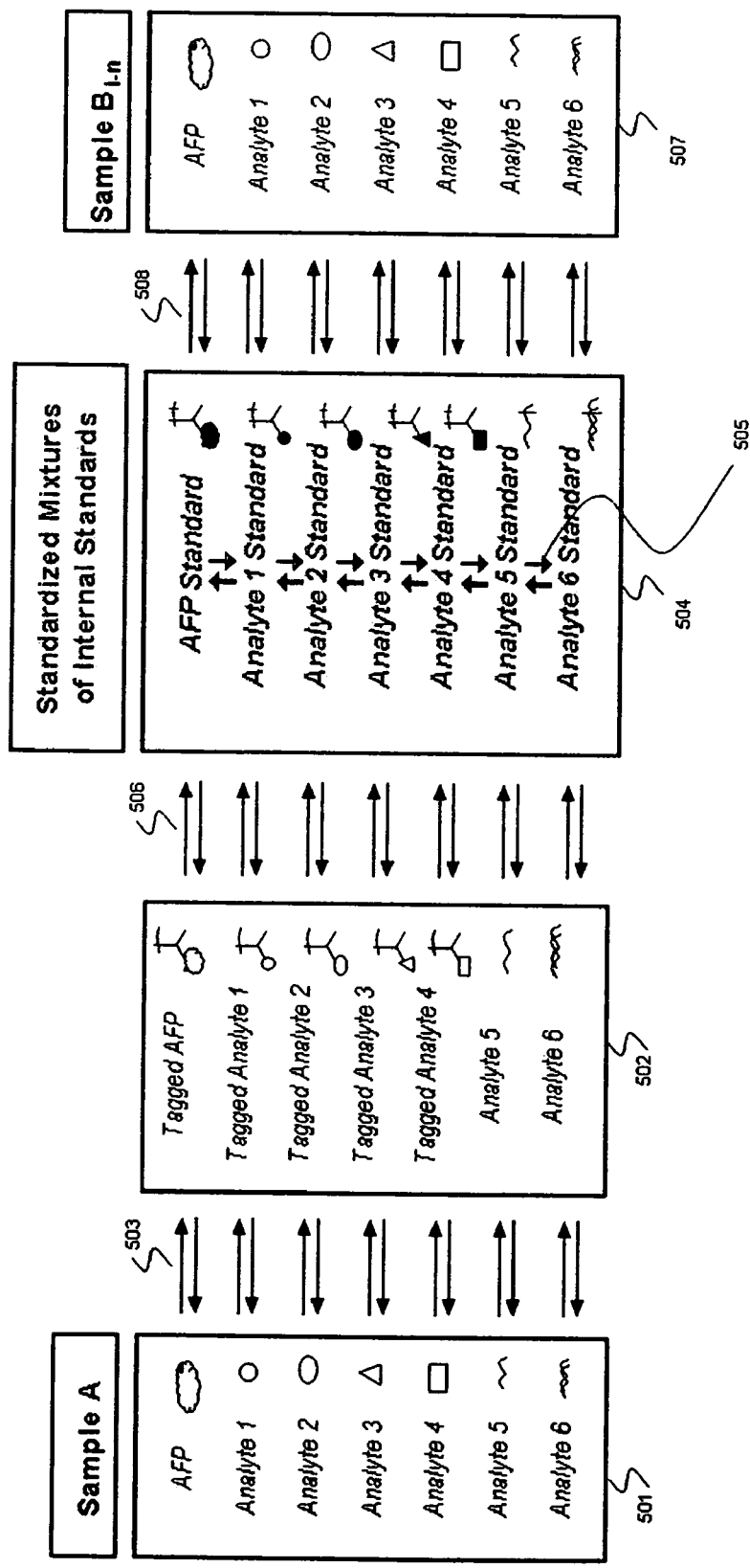
FIG. 5 illustrates a standardized mixture used in some embodiments of the present invention and its relationship to analytes to be assayed.

FIG. 5 illustrates a standardized mixture used in some embodiments of the present invention and its relationship to analytes to be assayed. Feature 501 illustrates a sample, Sample A, which comprises a number of analytes to be assayed, including analytes 1-6, as well as an analyte to serve as a reference, comprising α-fetoprotein (AFP) in this illustration. Analytes 1, 2, 3, 4 and AFP comprise non-nucleic acid analytes; analytes 5 and 6 comprise nucleic acid analytes.

Feature 502 illustrates tagged analytes, where non-nucleic acid analytes 1, 2, 3, 4, and AFP are coupled to nucleic acid tags, e.g., as detailed above. Nucleic acid analytes 5 and 6 need not be coupled to nucleic acid tags. Feature 503 (horizontal arrows) illustrates the relationship between sample analytes and their nucleic acid tags. In the illustrated embodiment, monoclonal antibodies cross-linked to nucleic acid tags are used to couple one molecule of analyte to one copy of its nucleic acid tag in a fixed (or substantially fixed) equimolar ratio, as detailed above. Accordingly, each nucleic acid tag can represent its corresponding non-nucleic acid analyte in an amplification reaction. Any other techniques provided above, known in the art and/or as can be developed for coupling nucleic acids can also be used.

Feature 504 illustrates a standardized mixture of internal standards for assaying both nucleic acid and non-nucleic acid analytes. The standardized mixture comprises competitive template for the nucleic acid tag for the reference analyte AFP (AFP standard), competitive template for nucleic acid tags for non-nucleic acid analytes 1, 2, 3, and 4 (analytes 1-4 standards), and competitive template for nucleic acid analytes 5 and 6 (analytes 5-6 standards). In the illustrated embodiment, competitive template internal standards for non-nucleic acid analytes, AFP and analytes 14, further comprise antagonists for AFP and analytes 14, respectively. As detailed above, monoclonal antibodies cross-linked to competitive templates can be used to couple one molecule of antagonist to one copy of competitive template in a fixed (or substantially fixed) equimolar ratio. Accordingly, each competitive template can represent its corresponding antagonist in an amplification reaction. Any other techniques provided above, known in the art and/or as can be developed for coupling nucleic acids can also be used Feature 505 (vertical two-way arrows) illustrates a relationship among internal standards within a standardized mixture. Internal standard for each of the analytes to be assayed can be at a fixed concentration relative to other internal standards within a standardized mixture. Accordingly, in some embodiments, when sample analytes are combined with a standardized mixture, the concentration of each internal standard is fixed relative to the analytes, and/or relative to nucleic acid tags representing corresponding analytes.

Standardized mixtures can comprise internal standards for only non-nucleic acid analytes or for only nucleic acid analytes, and, as detailed above, either non-nucleic acid or nucleic acid analytes can serve as a reference analyte. In some embodiments, the standardized mixture comprises an internal standard for an analyte to be assayed and one internal standard for a reference analyte. In some embodiments, the standardized mixture comprises additional internal standards for assaying additional analytes, e.g., additional antagonists for the additional analytes coupled to additional competitive templates. For example, in some embodiments, standardized mixture comprises at least about 2, at least about 50, at least about 100, at least about 200, at least about 500, at least about 1,000, at least about 5,000, at least about 10,000, at least about 50,000, or at least about 100,000 other internal standards. For example, competitive templates for several genes to be measured can be included in a given standardized mixture, and/or competitive templates coupled to antagonists for several non-nucleic acid analytes to be assayed can be included in a given standardized mixture, as illustrated in feature 504.

Feature 506 (horizontal two-way arrows) illustrates a relationship between an internal standard and its corresponding analyte in a sample, whereby each sample analyte can be measured relative to its respective internal standard in the standardized mixture. Because the competitive template for each nucleic acid analyte, and/or each nucleic acid tag representing a non-nucleic acid analyte, can be present at a fixed concentration relative to other competitive templates, the standardized mixture can allow a target analyte to be assessed relative other analytes being measured with the standardized mixture 504. For example, Sample A 501 can be combined with standardized mixture 504 (before or after tagging as described above), to form a master mixture used for further co-amplifications. For example, the master mixture can be used in co-amplifying nucleic acid tag corresponding to analyte 1 and its competitive template corresponding to analyte 1 standard, as well as co-amplifying cDNA corresponding to a nucleic acid analyte (analyte 5) and its competitive template (analyte 5 standard).

In a two-step adaptation using standardized mixture 504, a target nucleic acid and its respective competitive template can be co-amplified to produce first amplified product thereof. The amplified products can be diluted and further co-amplified one or more times, as described in more detail above. In some embodiments, first amplified product of the reference nucleic acid can be diluted and further amplified one or more times, also as described above.

Feature 507 illustrates a number of other samples, Samples $B_{1-n}$, which also comprise AFP and analytes 1-6. In some embodiments, analyte abundance measured in reference to AFP can be re-calculated relative to that of another reference analyte, if so desired. For example, if another analyte, e.g. any other of analytes 1 to 6, appears to vary less than AFP across the samples $B_{1-n}$ 507, the data may be re-calculated ("normalized") to that reference analyte without altering relative measurements within a sample. Re-calculation may be accomplished using a spreadsheet, in some embodiments, When data are re-calculated, the relative measured amounts among analytes can remain the same or substantially the same. In some cases, re-calculating relative to a new reference can alter the numerical value for analyte abundance without altering the numerical values for different analytes relative to each other. Without being limited to a particular hypothesis and/or theory, this may be explained in that measured amounts of analytes can be said to be linked through use of a common standardized mixture of internal standards 504. Thus, the ratio between two analytes within a sample would be the same or substantially the same using AFP, β-actin, or a combination of analytes as the reference analyte.

Feature 508 (horizontal two way arrows) illustrates that each of these analytes in additional samples $B_{1-n}$ 507 can be measured relative to its respective internal standard in the standardized mixture 504. As with Sample A 501, each of these analytes can be measured relative to other analytes assayed with the standardized mixture 504. Further, it is possible to compare data from analysis of Sample A 501 to data from analysis of samples $B_{1-n}$ 507. For example, because the number of molecules for each internal standard is known within the standardized mixture, it is possible to calculate all data in the form of molecules/reference analyte molecules.

In some embodiments, the standardized mixture 504 comprises sufficient amounts of internal standards for assessing one or more of the analytes in a large number of samples $B_{1-n}$ 507, e.g., in more than about $10^4$ samples, in more than about $10^5$ samples, in more than about $10^6$ samples, in more than about $10^7$ samples, in more than about $10^8$ samples; in more than about $10^9$ samples, in more than about $10^{10}$ samples, in more than about $10^{11}$ samples, in more than about $10^{12}$ samples, in more than about $10^{13}$ samples, in more than about $10^{14}$ samples, or in more than about $10^{15}$ samples. In some preferred embodiments, use of a common standardized mixture for multiple samples can reduce time to obtain results. For example, re-preparing reagents for PCR amplifications can be time consuming and can also lead to sources of error.

As discussed previously, a nucleic acid and its competitive template may be co-amplified (and/or further co-amplified) in the same or different vessels as one or more other nucleic acid(s) and corresponding competitive template(s). See, e.g., Apostolakos et al., supra, (1993); Willey et al., supra, (1998). In some preferred embodiments, use of a standardized mixture 504 allows different nucleic acids amplified in separate vessels to be directly compared. In some embodiments, for example, a nucleic acid representing one analyte and its competitive template are co-amplified in one vessel, while another nucleic acid representing another analyte and its competitive template are co-amplified in a different vessel. In either case, as feature 505 illustrates, an analyte can be measured relative to its respective internal standard within the standardized mixture and the other analyte can serve as a reference analyte. That is, in preferred embodiments, the use of a standardized mixture allows the concentration of internal standard for an analyte relative to others to remain fixed across different measurements, including measurements from different vessels.

As feature 508 illustrates, use of a common standardized mixture allows direct comparisons to be made among Samples $B_{1-n}$ 507. The different samples may be amplified at different times, e.g., on different days; in the same or different experiments in the same laboratory; and/or in different experiments in different laboratories. Crawford et al., supra, (2001); Crawford et al., supra, (2002); Crawford et al., supra, (2000); DeMuth et al., *Am. J. Respir. Cell. Mol. Biol.* 19, 18-24 (1998); Mollerup et al., *Cancer Res.*, 59, 3317-3320 (1999); Rots et al., *Leukemia* 14, 2166-2175 (2000); Rots et al., *Blood* 94, 3121-3128 (1999); Allen et al., *Am. J. Respir. Cell. Mol. Biol.* 21, 693-700 (1999); Loitsch et al., supra, (1999); Vondracek et al., supra, (2002). In preferred embodiments, measurements are made using the same standardized mixture and dilution of internal standards.

Further, in some embodiments, measurements obtained using various quantifying approaches are directly comparable where a common standardized mixture is used. For example, statistically similar results were obtained using a common standardized mixture and quantifying amplified product by various types of electrophoresis, or by either a Caliper AMS 90 SE30 electrophoretic separation or by hybridizing them to microarrays in accordance with some embodiments of the instant invention. In another example, reproducible gene expression measurements were obtained when amplified product was quantitated using MALDI-TOF MS instead of using electrophoresis. Ding et al., *Proc. Natl. Acad. Sci. USA* 100, 3059-3064 (2003).

The use of the standardized mixtures may also be applied to other methods for measuring nucleic acids, e.g., in real-time RT-PCR. For example, in some embodiments, obtaining a ratio of amplified product of a nucleic acid to amplified product of its competitive template can comprise a use of real-time RT-PCR analyses. As another example, a standardized mixture may be used in accordance with some embodiments of the instant invention in combination with competitive template techniques described, e.g., in Siebert et al., *Nature* 359: 557-558 (1992); Siebert et al., *Biotechniques* 14:244-249 (1993), and Clontech Brochure, 1993, Reverse Transcriptase-PCR (RT-PCR). For example, fluorescent probes for using a standardized mixture with real-time RT-PCR may be developed.

B. Preparation of Standardized Mixtures

Some embodiments of the invention provide methods for preparing a standardized mixture of reagents. In preferred embodiments, reagents are selected to provide compositions for assaying analytes with improved specificity, sensitivity, reproducibility, accuracy, stability, robustness, lower detection thresholds, and/or reduced coefficients of variations. As used herein, "reagent" can refer to a component used in preparing a mixture, including solvent and/or solute. For example, reagents include water, e.g., in the case of aqueous mixtures. In preferred embodiments, reagents include internal standards for analytes to be assayed. As provided above, an internal standard for a nucleic acid analyte can comprise a competitive template. An internal standard for a non-nucleic acid analyte can comprise a competitive template for a nucleic acid tag coupled to the analyte, where the competitive template is itself coupled to an antagonist for the analyte. Known quantities of internal standards for multiple analytes can be mixed together to provide a standardized mixture. Accordingly, in preferred embodiments, the standardized mixture provides known amounts of competitive templates for nucleic acids representing each analyte to be assayed.

In some embodiments, the standardized mixture prepared comprises sufficient reagents, e.g., sufficient amounts of competitive templates, for assaying one analyte. In preferred embodiments, the standardized mixture comprises sufficient reagents for assaying more than one analyte, e.g., at least about 50, at least about 96, at least about 100, at least about 200, at least about 300, at least about 500, at least about 800, at least about 1,000, at least about 5,000, at least about 10,000, at least about 50,000, or at least about 100,000 different analytes. In some embodiments, the standardized mixture comprises sufficient reagents for assaying less than about 100,000, less than about 500,000, less than about 1,000,000, less than about 5,000,000, less than about 10,000,000, less than about 50,000,000, or less than about 100,000,000 different analytes. In some embodiments, different analytes correspond to different molecular materials, including nucleic acid and non-nucleic acid analytes, e.g., proteins, nucleic acids, small molecules, etc, as provided above.

In some embodiments, internal standard competitive templates can be prepared for a number of analytes to be assayed. The competitive templates can then be cloned to generate enough to assay analyte in more than about $10^4$ samples, in more than about $10^5$ samples, in more than about $10^6$ samples, in more than about $10^7$ samples, in more than about $10^8$ samples; in more than about $10^9$ samples, in more than about $10^{10}$ samples, in more than about $10^{11}$ samples, in more than about $10^{12}$ samples, in more than about $10^{13}$ samples, in more than about $10^{14}$ samples, or in more than about $10^{15}$ samples.

For example, consider a standardized mixture comprising sufficient reagents to assay about $10^7$ molecules of an analyte in about $10^9$ samples, thereby requiring about $10^{16}$ molecules of internal standards. Where a protein is used as an antagonist and the molecular weight of the protein is about 100 kD, the weight of this much protein reagent would be about $10^{16}$ molecules/[$2\times10^{23}$ molecules/M]$\times10^5$ g/M=about $5\times10^{-3}$ g=about 5 mg. Where an antibody is used to couple competitive template to the antagonist, and the molecular weight of a typical antibody is about 150 kd, the weight of the antibody reagents would be about 7.5 mg. Where a 300 bp DNA molecule is used as the competitive template, and the molecular weight of the DNA is 300 bases×about 300 Daltons/base, the weight of the competitive template reagent would be about $9\times10^4$ g/M×$5\times10^{-8}$ M=about $4.5\times10^{-3}$ g=about 4.5 mg. The weight of the antagonist-antibody-competitive template internal standard in this embodiment would be about 4.5 mg+about 7.5 mg+about 5 mg=about 17 mg. If the standardized mixture was prepared for assaying about 100 such analytes, a solution comprising about 100×17 mg=about 1.7 g of internal standards would be prepared. In preferred embodiments, about 1.7 g would be made up into a standardized mixture of about 100 ml volume or greater. If about 100 mL contains sufficient reagents for assaying about $10^9$ samples, $10^{-7}$ mL of the concentrated (stock) standardized mixture can be used for assaying a given sample. In some embodiments, about $10^{-2}$ mL provides a working volume. Accordingly, the about 1.7 mg/100 mL stock solution could be diluted about 1 generating a volume of $10^7$ mL or $10^4$ L. Because protein analytes may occur at lower levels, e.g., where proteins are expressed at lower levels, the amount of material needed may be approximately about 10-fold less in some embodiments, e.g., about 170 mg.

In some embodiments, the standardized mixture prepared comprises sufficient reagents, e.g., sufficient amounts of competitive template, for assaying a number of analytes in a number of samples, e.g., more than about $10^6$ samples. In preferred embodiments, the standardized mixture allows direct comparison between the amount assayed in a first sample and in at least about one other sample, at least about 2 other samples, at least about 3 other samples, or at least about 4 other samples. More preferred embodiments allow direct comparison of assayed amounts in at least about 6 samples, at least about 10 samples, at least about 50 samples, at least about 100 samples, at least about 500 samples, at least about 1,000 samples, at least about 5,000 samples, at least about 10,000 samples, at least about 50,000 samples, at least about 100,000 samples, at least about 500,000 samples, at least about 1,000,000 samples, at least about 5,000,000 samples, or at least about 10,000,000 samples. In some specific embodiments, the standardized mixture allows direct comparison of amounts assayed in up to an unlimited number of samples.

In some embodiments, the reagents include at least one forward primer and/or a reverse primer capable of priming amplification of a competitive template in the mixture. In some embodiments, a forward primer and/or a reverse primer are designed to have substantially the same annealing temperature as another forward primer and/or reverse primer in the standardized mixture. Designing primers with the same or substantially the same annealing temperature can allow amplification reactions to achieve approximately the same amplification efficiency under identical or substantially identical conditions. In such embodiments, if there is variation in amplification efficiency, amplification efficiency of a nucleic acid and its competitive template can be affected identically (or substantially identically), so that the ratio of amplified product of the nucleic acid and its corresponding competitive template may not vary or may not vary substantially. In some specific embodiments, a forward and reverse primer have the same or substantially the same annealing temperature as each of the other forward and reverse primers in a given standardized mixture. For example, the annealing temperature may be about 40° C., about 40° C., about 44°, about 50° C., about 55° C., about 57° C., about 58° C., about 59° C., about 60° C., about 65° C., about 70° C., about 75° C., or about 85° C.

The internal standards can be carefully quantified and then mixed together to form a standardized mixture. In some embodiments, the competitive template and a corresponding forward primer and/or reverse primer can be selected to allow for detection of about $10^{-10}$, about $10^{-11}$, about $10^{-2}$, about $10^{-13}$, about $10^{-14}$, about $10^{-15}$, about $10^{-16}$, about $10^{-17}$, about $10^{-18}$ M or less of the nucleic acid to be measured, e.g., where the nucleic acid comprises a nucleic acid analyte, cDNA molecule corresponding to a nucleic acid analyte and/or a nucleic acid tag for to a non-nucleic acid analyte. For example, the forward and/or reverse primer can allow for the detection of about 600 molecules, about 60 molecules or about 6 molecules or less of analyte in some embodiments.

As discussed above, competitive template for a nucleic acid tag coupled to an analyte can be coupled to an antagonist for the analyte, and in some embodiments coupling comprises use of an antibody. In some preferred embodiments, a high specificity antibody is used. A high specificity antibody can refer to an antibody that shows little or no non-specific binding, i.e., the antibody recognizes and preferentially binds to a given analyte with little or no binding to any other analyte in a sample or mixture under conditions used. For example, in preferred embodiments binding to a given analyte occurs with at least about a $10^6$-fold greater affinity, preferably at least about a $10^7$-fold greater affinity, more preferably at least about a $10^8$-fold greater affinity, and most preferably at least about a $10^9$-fold greater affinity than binding to other analytes in a sample or mixture.

In some preferred embodiments, a high affinity antibody is used. A high affinity antibody can refer to an antibody that shows a high binding affinity or a high binding constant for a given analyte. Such an antibody can also be referred to as being highly sensitive for its target analyte. In some embodiments, affinity of an antibody for an analyte can be tested to allow for selection of a high affinity antibody. Various techniques known in the art can be used, including, e.g., surface plasmon resonance (SRP), to test affinity of an antibody for an analyte (or its antagonist). Further details, e.g., are provided in Example I.

In some preferred embodiments, antibodies used are of a high purity.

In some preferred embodiments, a monoclonal antibody is used, e.g., a monoclonal antibody that recognizes a given epitope on a sample analyte. Monoclonal antibodies can provide a consistent supply of identical (or substantially identical) antibodies of high affinity, high specificity and/or high purity. In some embodiments, for example, monoclonal antibodies show less lot to lot variability compared with polyclonal antibodies. Commercially available high affinity monoclonal antibodies can be used in some embodiments. For example, high affinity monoclonal antibodies for carcinoembryonic antigen (CEA) and/or to α-fetoprotein (AFP) are commercially available and can be used in some embodiments. Fitzgerald Industries Intl Inc (Concord, Mass.).

Selection of antibodies, competitive templates and/or primers as detailed above can provide standardized mixtures capable of detecting and/or quantifying small amounts of analytes. For example, in some embodiments, a standardized mixture of the instant invention can detect and/or quantify less than about 1,000, less than about 800, less than about 600, or less than about 400 molecules. In some embodiments, less than about 100 molecules, less than about 60 molecules, less than about 10 molecules, less than about 6 molecules, or less than about 1 molecule of an analyte can be detected and/or quantified in a sample. In some embodiments, a standardized mixture of the instant invention can detect and/or quantify less than about 10,000,000, less than about 5,000,000, less than about 1,000,000, less than about 500,000, less than about 100,000, less than about 50,000, less than about 10,000, less than about 8,000, less than about 6,000, less than about 5,000, or less than about 4,000 molecules of an analyte in a sample.

In some embodiments, the reagents for assaying analytes are stable. For example, the primers and/or competitive templates of a standardized mixture may comprise stable nucleic acid molecules, such as DNA. In some embodiments, competitive templates are coupled to antagonists for non-nucleic acid analytes to form stable conjugates. For example, DNA molecules can be used as competitive templates, more preferably double-stranded DNA, even more preferably double-stranded DNA comprising at least about 100 base pairs. For example, DNA may increase stability in some embodiments, as discussed above. Also as discussed above, DNA molecules can be directly cross-linked to antibodies for specific analytes.

In some embodiments, the antibody used (polyclonal or monoclonal) is itself stable. For example, the antibody used can have a shelf life of at least about 6 months, at least about 1 year, at least about 5 years, at least about 10 years, at least about 30 years, at least about 50 years, or at least about 100 years. Stability may be tested at regular intervals, e.g., at about 1 month, about 2 month, about 3 month, about 6 month or about 1 year intervals, e.g., using SPR analysis. As discussed above, in some embodiments, analytes may be coupled to nucleic acid tags via artificial reagents, such as peptoids, e.g., where the artificial reagents are more stable than antibodies. See, e.g., Naffin et al., supra, (2003); Alluri et al., supra, (2003); Burkoth et al., supra, (2002); de Haan et al., supra, (2002).

Reagents of a standardized mixture may be stable for at least about 20 years, at least about 50 years, at least about 100 years, at least about 500 years, or at least about 1,000 years. In preferred embodiments, a standardized mixture of the present invention can provide sufficient reagents for assays expected to be made for the next at least about 20 years, at least about 50 years, at least about 100 years, at least about 500 years, or at least about 1,000 years. For example, a standardized mixture, once prepared, can be aliquoted, lyophilized and frozen for long-term stability. In a specific embodiment, standardized mixture comprising internal standards for CEA and AFP provide reproducible results over at least about 1 month, at least about 3 months, at least about 6 months, or at least about 1 year, with one or more of the sensitivities, one or more of the specifications, one or more of the robustness, one of more of the accuracies, one or more of the detection limits, one or more of the coefficients of variation and/or one of more of the stabilities discussed herein.

In some embodiments, long term storage of reagents and/or samples comprising DNA can be achieved at −20 degrees C. In some embodiments, reagents and/or samples comprising RNA are stable for years frozen as an EtOH precipitate and/or in RnASE free water. In some embodiments, competitive templates are stably frozen for more than six years. In some embodiments, cDNA samples are stable for more than two years frozen at −20 degrees C.

A standardized mixture according to some embodiments of the present invention can be prepared to perform one or more of the methods described herein. For example, as described above, using a standardized mixture, an analyte can be assessed relative to one or more other analytes (e.g., that can serve as controls for loading into a reaction). Also as detailed above, an analyte can be assessed relative to its corresponding internal standard provided in the standardized mixture.

In some embodiments, the standardized mixture can allow for detection and/or quantification with one or more of the sensitivities, one or more of the specificities, one or more of the robustness, one or more of the accuracies, one or more of the detection limits, and/or with one or more of the coefficients of variation taught herein. Additional features of the prepared standardized mixture will be apparent to one of skill in the art, based on the disclosures herein.

C. Serially-Diluted Standardized Mixtures

Some embodiments of the instant invention provide a series of serially-diluted standardized mixtures for use in assaying analytes, as discussed above. "Serially-diluted standardized mixtures" can refer to two or more standardized mixtures in which one or more of the reagents in the standardized mixtures is serially-diluted. In some embodiments, one or more reagents in the standardized mixtures is serially-diluted relative to a different one or more of the reagents in the mixtures.

For example, as described above, a competitive template for a nucleic acid representing a sample analyte can be serially diluted relative to a competitive template for a reference nucleic acid (e.g., either a reference nucleic acid analyte, a cDNA molecule corresponding thereto, or a nucleic acid tagging a reference non-nucleic acid analyte). Where competitive templates are coupled at known and fixed (or substantially fixed) ratios to antagonists, the series of standardized mixtures can provide antagonist for one analyte at a series of known concentrations relative to antagonist for another analyte.

Figure 6:
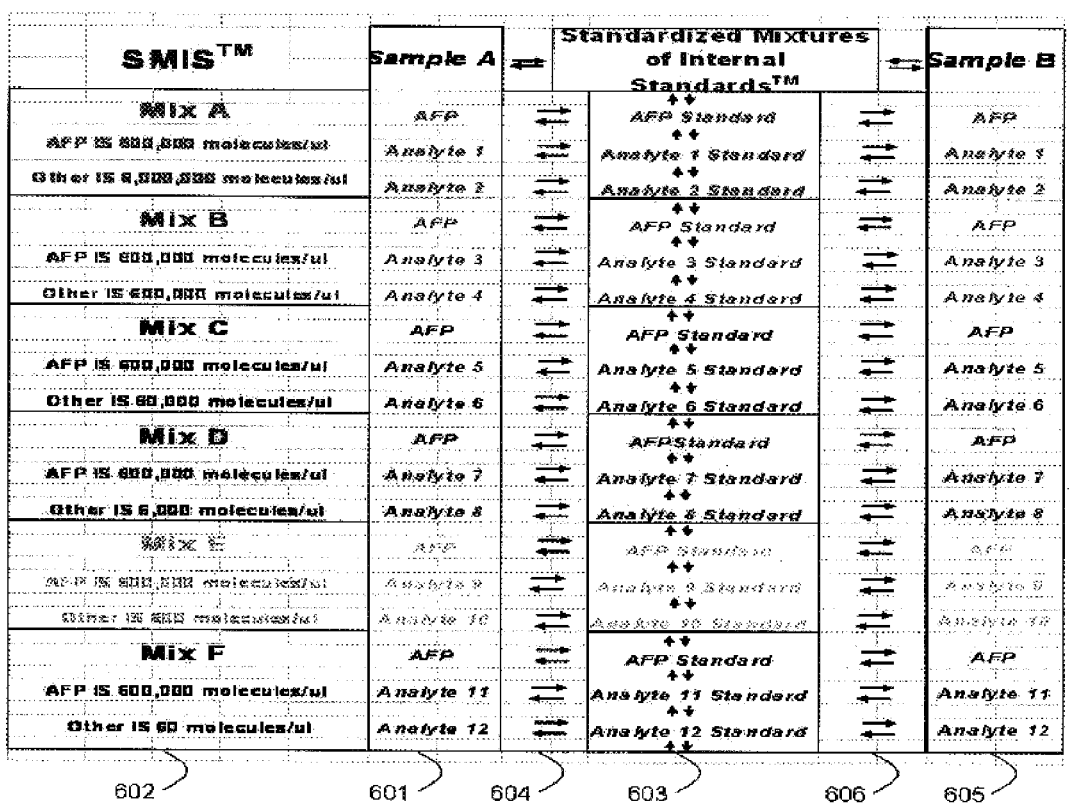
FIG. 6 illustrates a series of standardized mixtures used in some embodiments of the present invention and its relationship to analytes to be assayed.

FIG. 6 illustrates a series of standardized mixtures used in some embodiments of the present invention and its relationship to analytes to be assayed. In the figure, "IS" refers to internal standard and "SMIS" refers to a standardized mixture of internal standards, prepared in accordance with some embodiments of the instant invention. One of the series of standardized mixtures is referred to as a "Mix."

Feature 601 illustrates a sample, Sample A, which comprises a number of analytes to be assayed, including analytes 1-12, as well as an analyte that serves as a reference, comprising AFP in this illustration. As before, analytes may be nucleic acid or non-nucleic acid analytes.

Feature 602 illustrates a series of six standardized mixtures, Mixes A-F, comprising about 10-fold dilutions of internal standards for different analytes relative to internal standard for the reference analyte, AFP. In some embodiments, competitive template for the reference can be present at two (or more) different concentrations in two (or more) of the serially-diluted standardized mixtures. For example, where the first reference analyte varies in comparison to a second reference analyte, use of more than one concentration can be helpful in determining inter-sample and/or inter-specimen variation. In some embodiments, the series can comprise serial dilutions comprising internal standards for more or less than the 12 analytes of FIG. 6. For example, a series can be prepared for a 96-analyte standardized mixture or a standardized mixture comprising various numbers of internal standards, as detailed above.

Feature 603 illustrates the relationship between internal standard for the reference analyte (AFP standard) compared to internal standards for analytes to be assayed (analytes 1 to 12 standards) in the different serially-diluted mixtures. Use of the series can allow measurement of analyte abundance for analytes occurring over a range of concentrations, e.g., a range of more than six orders of magnitude and/or any of the ranges provided herein.

Feature 604 (horizontal two way arrows) illustrates how these different analytes in the Sample 601 are in balance with (i.e., calibrated to) different concentrations of their corresponding internal standards in the different mixes. "Balancing" or being in balance with, as used herein, can refer to calibrating amounts of sample analyte with the amount of its corresponding internal standard. For example, analytes 9 and 10 in Sample A 601, present in low abundance, are in balance with Mix E comprising 600 molecules/ul of internal standard each of for analyte 9 and analyte 10. Analytes 9 and 10 are preferably assayed using Mix E. Analytes 6 and 7 are present at higher levels in Sample A 601 and are in balance with Mix C and Mix D, respectively. Analyte 6 is preferably assayed using Mix C and analyte 7 is preferably assayed using Mix D.

In some embodiments, a specimen can be diluted until any one (or more) sample analytes is approximately balanced with, i.e., approximately calibrated to, the amount of its internal standard in a standardize mixture. Approximate calibration can occur when the analyte is within about a 10-fold range, about a 9-fold range, about an 8-fold range, about a 7-fold range, about a 6-fold range, about a 5-fold range, about a 4-fold range, about a 3-fold range, about a 2-fold range, or about a 1-fold range or less, of the concentration of the internal standard for that particular analyte in the standardized mixture. In preferred embodiments, the ratio of amplified product of a nucleic acid to its competitive template is about 1:10 to about 10:1 (e.g., for measurement to be within linear dynamic range).

In some embodiments, a sample of tagged analytes can be diluted so that the amount of amplified product of a reference nucleic acid (e.g., a nucleic acid tagging a non-nucleic acid reference analyte) is within about 10-fold of the amount of co-amplified product of its competitive template. For example, a specimen and/or sample can be diluted to provide a series of serially-diluted samples and one of the series selected, for combining with a standardized mixture, depending on the concentration of a reference analyte in the dilution. A dilution can be selected that provides about equivalent reference analyte molecules as there are internal standard molecules for the reference analyte in a given Mix. In some embodiments, a software program can be used to determine a desired sample dilution. In preferred embodiments, all standardized mixtures in a given series contain a given number of molecules of a particular reference analyte internal standard, allowing any of the standardized mixtures to be used in this balancing.

In some embodiments, use of a series of standardized mixtures allows detection and/or quantification of analytes over a range of concentrations. For example, in some embodiments, the amounts of two analytes to be assayed, e.g., mRNA levels and/or protein levels expressed from two or more different genes, vary over a range of less than about one order of magnitude, more than about one order of magnitude, or more than about 2 orders of magnitude. In some embodiments, the amounts of two different analytes to be assayed, e.g., mRNA levels and/or protein levels expressed from two or more different genes, vary over a range of about 3 or more orders of magnitude, about 4 or more orders of magnitude, about 5 or more orders of magnitude, about 6 or more orders of magnitude, or about 7 or more orders of magnitude, e.g., spanning an about 7-log range of gene expression. In some embodiments, the amounts of two different analytes to be assayed vary over a range of about 8 or more, about 9 or more, or about 10 or more orders of magnitude, e.g., spanning an about 10-log range of analyte abundance. Such ranges may be important in detecting biological and/or chemical warfare agents, for example.

As provided above, analyte abundance can be discussed in terms of copies/cell for analytes expressed and/or occurring in cells. In some embodiments, the amounts of two different analytes to be assayed vary over ranges including about $10^{-3}$, about $10^{-2}$, about 0.1, about 1, about 10, about $10^2$, about $10^3$, about $10^4$, about $10^5$, or about $10^6$ copies/cell.

Feature 605 illustrates a different sample, Sample B, also comprising analytes 1-12 and AFP.

Feature 606 (horizontal two way arrows) illustrates the different analytes in Sample B 605 are also in balance with different concentrations of their corresponding internal standards in the different mixes. A given analyte in a different sample can be in balance with the same Mix, allowing past experience with assaying a given analyte to inform the selection of an appropriate Mix. In some embodiments, e.g., the Mix selected initially may be based on past experience and/or prediction of the amount of analyte expected. For example, Mix A, Mix B, Mix C, Mix D, Mix E, or Mix F may be used initially for combining with a sample. In some embodiments, an appropriate standardized mixture can be selected based on data in some embodiments of databases described herein.

In preferred embodiments, the Mix selected is one containing a concentration of internal standard likely to be approximately calibrated with (e.g., within about a 10-fold range) of the amount of analyte or analytes in the sample being assayed. In some embodiments, a Mix for combining with the sample is chosen to provide an amount of amplified product of a nucleic acid representing a sample analyte within about 10-fold of the amount of co-amplified product of its competitive template, e.g., where the nucleic acid comprises a nucleic acid analyte, a cDNA molecule corresponding thereto, or a nucleic acid tag for a non-nucleic acid analyte. In some embodiments, a software program can be used to make the selection. For example, computer implementation may comprise instructing a robotic handler to select one of the serially-diluted standardized mixtures for combining.

Where the amounts of co-amplified product of a nucleic acid and of its competitive template differ greatly, e.g., falling outside an about 10-fold range, the co-amplification may be repeated using a different Mix of the series of serially-diluted mixtures. In some embodiments, software determines area under curve for the amplified products and calculates an NT/CT ratio. In some embodiments, software can also compare this ratio with the NT/CT ratio for the nucleic acid serving as a reference, and/or determine whether to use another Mix.

In preferred embodiments, the next Mix selected from the series is based on the ratio obtained when amplified product of a nucleic acid is compared to co-amplified product of its competitive template. That is, a different Mix providing a greater or lesser concentration of the internal standard can be selected, as appropriate. For example, where the ratio is less than about 1/10, a more dilute mixture from the series will be used subsequently; where the ratio is more than about 10/1, a more concentrated mixture from the series will be used. The more dilute mixture and/or the more concentrated mixture selected may be the next more dilute and/or the next more concentrated mixture in the series or a different serially-diluted mixture in the series, e.g., depending on the magnitude of the ratio obtained. In some embodiments, software can be used to automatically determine which Mix should be selected next and/or to automatically communicate the correct Mix to be used to a robot, e.g., instructing a robotic handler to combine a sample with the new Mix.

In preferred embodiments, the amount and/or dilution of sample analytes can be kept constant while a different standardized mixture is used. For example, if Mix D were used and the amount of amplified product of a nucleic acid was more than about 10-fold greater than that of its competitive template, the experiment can be repeated with the same starting amount of sample analyte, but using Mix C, which has about a 10-fold higher concentration of the internal standard, or Mix A or Mix B. Where the amount of amplified product of a nucleic acid is less than about 10-fold lower than that of the competitive template, the experiment can be repeated with the same starting amount of sample, but using Mix E or Mix F. When an appropriate mix is used, sample analyte represented by the amplified nucleic acid can be assayed, in accordance with some embodiments of the invention provided herein.

D. Preparation of Serially-Diluted Standardized Mixtures

Some embodiments of the instant invention provide methods for preparing a series of serially-diluted standardized mixtures of reagents. In some embodiments, one or more of the series of standardized mixtures comprises sufficient reagents, e.g., sufficient amounts of internal standards, for assaying a number of analytes in a number of samples, e.g., more than about $10^6$ samples. In preferred embodiments, the series of standardized mixtures allows direct comparison between the amount assayed in a first sample and in at least about one other sample, at least about 2 other samples, at least about 3 other samples, or at least about 4 other samples. More preferred embodiments allow direct comparison of assayed amounts in at least about 6 samples, at least about 10 samples, at least about 50 samples, at least about 100 samples, at least about 500 samples, at least about 1,000 samples, at least about 5,000 samples, at least about 10,000 samples, at least about 50,000 samples, at least about 100,000 samples, at least about 500,000 samples, at least about 1,000,000 samples, at least about 5,000,000 samples, or at least about 10,000,000 samples. In some specific embodiments, the standardized mixture allows direct comparison of amounts assayed in up to an unlimited number of samples.

The series of serially-diluted standardized mixtures may be obtained by serially diluting a standardized mixture, e.g., a standardized mixture described above. For example, in some embodiments, one or more of the series may contain sufficient reagents for assaying various numbers of analytes and/or for assaying various numbers of samples, e.g., as detailed above. Similarly, in some embodiments, one or more of the series of serially-diluted standardized mixtures can comprise any of the reagents of some embodiments of the standardized mixtures described above. In some embodiments, any of the reagents used may be stable, e.g., providing one or more of the stabilities described herein.

In preferred embodiments, a standardized mixture is diluted so that the internal standard for a first analyte is at a series of concentrations relative to the internal standard for a second analyte. In some embodiments, a standardized mixture is serially diluted about 10-fold, providing about 10-fold serial dilutions of the internal standard for the first analyte relative to the internal standard for the second analyte. In some embodiments, other fold dilutions can be used, e.g., about 2-fold, about 4-fold, about 5-fold or about 15-fold dilutions. In some embodiments, at least two of the series of concentrations span about one order of magnitude, about 2 orders of magnitude, about 3 orders of magnitude, about 4 orders of magnitude, about 5 orders of magnitude, about 6 orders of magnitude, about 7 orders of magnitude, or more. In some embodiments, the series of concentrations includes at least two, at least 3, at least 4, at least 5, or six concentrations selected from about $10^{-10}$ M, about $10^{11}$ M, about $10^{-12}$ M, about $10^{-13}$ M, about $10^{-4}$ M, about $10^{-15}$ M, and about $10^{-16}$ M.

In some embodiments, one or more of the series of standardized mixtures can allow for detection and/or quantification with one or more of the sensitivities, one or more of the specificities, one or more of the robustness, one or more of the accuracies, one or more of the detection limits, and/or with one or more of the coefficients of variation taught herein, over various ranges of orders of magnitude, e.g., any of the orders of magnitude discussed herein.

E. Kits

Some embodiments of the instant invention provide kits comprising one or more of the compositions provided herein. For example, kits may comprise one or more standardized mixtures, series of standardized mixtures, internal standards (e.g., competitive templates and/or antagonist-antibody-competitive template complexes), primers, buffers, nucleic acid tags, antibody-nucleic acid tag conjugates, peptoids, receptors, and/or substrates for immobilization. In some embodiments, kits can comprise containers, instructions for carrying out one or more of the assays provided herein, and/or software capable of carrying out one or steps of methods provided herein and/or for analyzing data generated. In some embodiments, kits comprise notification of one or more FDA approved use(s) and/or instructions relating to such use(s).

In some embodiments, a kit can permit detection and/or quantification of low abundance analytes, e.g., with one or more of the sensitivities, one or more of the specificities, one or more of the robustness, one or more of the accuracies, one or more of the detection limits, and/or with one or more of the coefficients of variation taught herein. In some embodiments, kits provide one or more stable reagents, e.g., providing one or more of the stabilities described herein. In some embodiments, kits provide quality-controlled assays.

In some embodiments, the kits are compartmentalized. In some embodiments, for example different types of reagents are contained in separate containers. Containers can include glass or plastic containers, pouches, bags, vials, tubes, arrays, and the like. In some embodiments, containers allow transfer of reagents from one compartment to another compartment, preferably where the samples and reagents are not cross-contaminated and, more preferably where the reagents of different containers can be added in a quantitative fashion. Such containers can include a container to accept a sample, a container which contains standardized mixture(s), a container which contains primers, containers which contain buffers and/or wash reagents, and containers which contain the reagents used to detect the nucleic acid tag, amplified product, and the like. In preferred embodiments, kits of the present invention allow for detection and/or quantification of sample analytes with one or more of the sensitivities, one or more of the specificities, one or more of the robustness, one or more of the accuracies, one or more of the detection limits, and/or one or more of the coefficients of variation taught herein. In some embodiments, kits can be used in diagnostic applications, preferably in quality-controlled diagnostic applications, as described in more detail below.

III. Databases

Another aspect of the instant invention is directed to databases. For example, some embodiments provide a database of numerical values corresponding to analyte abundance in a number of samples. Some embodiments provide a database of numerical indices obtained from numerical values.

A. Database of Numerical Values

In some embodiments, a database is provided comprising numerical values corresponding to amounts of an analyte in a number of samples. Numerical values can correspond to amounts of analyte or analytes assayed in accordance with any of the various embodiments provided herein. In preferred embodiments, the numerical values are directly comparable between samples. For example, in some embodiments, the numerical values are directly comparable between at least about 5 samples, at least about 10 samples, at least about 50 samples, at least about 100 samples, at least about 500 samples, at least about 1,000 samples, at least about 5,000 samples, at least about 10,000 samples, at least about 50,000 samples, at least about 100,000 samples, at least about 500,000 samples, at least about 1,000,000 samples, at least about 5,000,000 samples, or at least about 10,000,000 samples. In some embodiments, direct comparison involves comparing the numerical values to one another without using a bioinformatics resource. In some embodiments, a bioinformatics resource, e.g., a simple bioinformatics resource, can be used.

In preferred embodiments, each value in the database has been made relative to an internal standard within a standardized mixture of internal standards. In preferred embodiments, numerical values correspond to numbers of molecules of a given analyte in a sample. In some embodiments, numerical values can be provided in units of (molecules of a first analyte)/(molecules of a second analyte), e.g., where the second analyte serves as a reference. Numerical values in some embodiments, for example, may correspond to less than about 1,000, less than about 800, less than about 600, or less than about 400 molecules of an analyte in a sample. In some embodiments, numerical values may correspond to less than about 100, less than about 60, less than about 10, less than about 6 molecules, or about 1 molecule of an analyte in a sample. In some embodiments, numerical values may correspond to less than about 10,000,000, less than about 5,000,000, less than about 1,000,000, less than about 500,000, less than about 100,000, less than about 50,000, less than about 10,000, less than about 8,000, less than about 6,000, less than about 5,000, or less than about 4,000 molecules of an analyte in a sample.

The database of some embodiments of the instant invention can comprise numerical values varying over a range. For example, in some embodiments, numerical values can vary over a range of less than about one order of magnitude, more than about one order of magnitude, or more than about 2 orders of magnitude. In some embodiments, numerical values corresponding to different analytes, e.g., mRNA levels and/or proteins levels expressed from two or more different genes, can vary over a range of about 3 or more orders of magnitude, about 4 or more orders of magnitude, about 5 or more orders of magnitude, about 6 or more orders of magnitude, or about 7 or more orders of magnitude, e.g., spanning the about 7-log range of gene expression. In some embodiments, numerical values corresponding to different analytes can vary over a range of about 8 or more, about 9 or more, or about 10 or more orders of magnitude, e.g., spanning an about 10-log range of analyte abundance. As provided above, analyte abundance can be discussed in terms of copies/cell for analytes expressed and/or occurring in cells. In some embodiments, numerical values correspond to about $10^{-3}$, about $10^{-2}$, about 0.1, about 1, about 10, about $10^2$, about $10^3$, about $10^4$, about $10^5$, or about $10^6$ copies/cell. Such ranges may be important in detecting biological and/or chemical warfare agents, for example.

In some embodiments, numerical values of the database correspond to less than about a two-fold difference in analyte abundance between 2 of the samples. In some embodiments, the numerical values correspond less than about a one-fold difference, less than about an 80% difference, less than about a 50% difference, less than about a 30% difference, less than about a 20% difference, less than about a 10% difference, less than about a 5% difference, or less than about a 1% difference.

Without being limited to a given hypothesis and/or theory, since the data in some embodiments is standardized against a common mixture of internal standards, direct comparisons are possible. For example, as discussed above, in some embodiments, the numerical values are directly comparable between a number of samples, e.g., samples obtained from different subjects and/or from different species. In some embodiments the numerical values are directly comparable between a number of samples measured and/or enumerated in different laboratories and/or at different times. In preferred embodiments, such comparisons are possible without the use of one or more calibrator samples (e.g., a non-renewable calibrator sample) and/or without the generation of one or more standard curves.

Two values can be descried as being "directly comparable" where, e.g., the numerical values of each describe the amounts relative to a common standard. As a readily understandable analogy, 10° C. is directly comparable to 50° C. as both values are provided relative to the boiling point of water (100° C.). Using some embodiments provided herein, the number of analyte molecules in a given sample is measured relative to its corresponding internal standard in a standardized mixture, rather than by comparing it to another sample. Use of a common standardized mixture can provide the common standard and can facilitate direct comparisons. In preferred embodiments, direct comparisons can be made between different numbers of samples as provided herein, with one or more of the sensitivities, one or more of the specificities, one or more of the robustness, one or more of the accuracies, one or more of the detection limits, and/or one or more of the coefficient of variation taught herein, for different numbers of analytes, as taught herein, including between non-nucleic acid and nucleic acid analytes, e.g., assayed over various periods of time as provided herein.

In contrast, using techniques such as real-time RT-PCR and/or microarray analysis (other than in combination with some embodiments of the instant invention), nucleic acids being measured scale differently. For example, differences in hybridization melting temperatures between nucleic acids with bound polynucleotides (microarrays) or fluorescent probes (real-time RT-PCR) cause measurements to scale differently. Consequently, relative amounts of different nucleic acids in a specimen and/or between specimen may not be directly comparable, e.g., it may not be possible to compare difference in expression among many genes in a sample. Further, real-time PT-PCR and/or microarray analysis measurements may not provide direct information as to the number of molecules present in a sample.

Assayed amounts may also be corrected for one or more sources of variation, e.g., in accordance with various embodiments of the teachings provided herein. In some embodiments, the values in the database show a coefficient of variation of less than about 50%, less than about 30%, less than about 25%, less than about 20%, less than about 15%, less than about 10%, less than about 5%, or less than about 1% between 2 of more samples. In some preferred embodiments, numerical values do not comprise a statistically significant number of false positives. In some preferred embodiments, numerical values do not comprise a statistically significant number of false negatives. In more preferred embodiments, numerical values do not comprise false negatives.

In some embodiments, the database further comprises numerical values corresponding to amounts of a number of other analyte(s) in the samples, where the amounts are directly comparable. The number of other analytes for which data is included in the database can be at least about 5, at least about 10, at least about 50, at least about 100, at least about 500, at least about 1,000, at least about 5,000, at least about 10,000, at least about 50,000, at least about 100,000, at least about 500,000, at least about 1,000,000, at least about 5,000,000, or at least about 10,000,000 other analytes. Such analytes can include nucleic acid and non-nucleic acid analytes, e.g., as discussed herein.

In some embodiments, the database of the instant invention can serve as a common databank, where analyte abundance for different analytes, including different types of molecular materials, are reported as numerical values that allow for direct inter-experiment comparison. In preferred embodiments, the database establishes a continuously expanding virtual multiplex experiment (i.e., data from an ever-expanding number of analytes, samples and/or specimens) can be entered into a given database and compared directly to other data within the database. This can lead to synergistic increases in knowledge, e.g., knowledge regarding the relationship between analyte abundance patterns and phenotype.

More preferred embodiments of the instant invention can be used to provide a common language for gene expression at the transcript and protein levels. Some embodiments, for example, provide a common language for gene expression across species. For example, homologous proteins in various species can be labeled with common nucleic acid tags and the tags can be amplified with common primers. This can allow for direct comparison of homologous proteins in a wide variety of species, e.g., corresponding to two or more of human, rat, mouse, pig, horse, sheep, rabbit, monkey, plant, fruit fly, bird, fish, yeast, fungal, bacterial and/or viral genes.

In some embodiments, the database is web-based. In some embodiments, the database invention finds use in experimental research, clinical diagnoses and/or drug development. For example, in some embodiments, the database can be used to advance studies on pathways of transcriptional control, and/or serve as a basis for mechanistic investigation. For example, bivariate analysis of individual gene expression numerical values for transcription factor genes and genes controlled by these transcription factors can improve understanding of gene expression regulation. In some embodiments, this can increase insight into control of gene expression, e.g., in normal and malignant cells.

In some embodiments, the numerical values of a database described herein can be used in clinical diagnostic testing. In some embodiments, the database can be used in pharmacodynamic studies of pharmaceuticals. Such applications are described in more detail below.

B. Database of Numerical Indices

Some embodiments of the instant invention provide a database comprising numerical indices. The numerical indices can be obtained by mathematical computation of 2 or more numerical values, where the numerical values correspond to amounts of 2 or more analytes in a number of samples.

In preferred embodiments, the numerical indices are directly comparable between the samples. For example, in some embodiments, the numerical indices are directly comparable between at least about 5 samples, at least about 10 samples, at least about 50 samples, at least about 100 samples, at least about 500 samples, at least about 1,000 samples, at least about 5,000 samples, at least about 10,000 samples, at least about 50,000 samples, at least about 100,000 samples, at least about 500,000 samples, at least about 1,000,000 samples, at least about 5,000,000 samples, or at least about 10,000,000 samples. In some embodiments, direct comparison involves comparing the numerical indices to one another without a bioinformatics resource. In some embodiments, a bioinformatics resource, e.g., a simple bioinformatics resource, can be used. In some specific embodiments, each measurement in the database has been made relative to an internal standard within a standardized mixture of internal standards.

As discussed above, analyte abundance can be reported as numerical values. The numerical values can be combined into numerical indices by mathematical computation to provide a numerical index, e.g., allowing mathematical interaction among the numerical values. For example, in some embodiments, a numerical index is calculated by dividing a numerator by a denominator, the numerator corresponding to the amount of one of 2 analytes and the denominator corresponding to the amount the other of the 2 analytes. In some embodiments, a numerical index is calculated by a series of one or more mathematical functions. For example, a numerical index may be calculated by a formula (analyte 1+analyte 2)/(analyte 3−analyte 4). A numerical index can be described as balanced e.g., where it is computed by a formula having equal numbers of numerical values in the numerator as in the denominator. Methods for obtaining numerical indices that indicate a biological state, e.g., that can act as biomarkers by correlating with a phenotype of interest, are detailed below.

In some embodiments, the numerical indices are directly comparable between a number of samples, e.g., samples obtained from different subjects and/or from different species. In some embodiments the numerical indices are directly comparable between a number of samples measured and/or enumerated in different laboratories and/or at different times.

In some embodiments, the database of the instant invention can serve as a common databank, where assayed amounts of different analytes, including different types of molecular materials, are mathematically combined to provide numerical indices that allow for direct inter-experiment comparison. In preferred embodiments, the database establishes a continuously expanding virtual multiplex experiment (i.e., data from an ever-expanding number of analytes, samples and/or specimens) can be used to calculate numerical indices that are entered into a given database and compared directly to other data within the database.

As discussed above, in some embodiments, any assayed analyte or combination of analytes, including all assayed analytes, can be used as the reference analyte and data calculated using a first reference analyte can be re-calculated relative to that of another reference analyte. In the case of numerical indices, the difference in value obtained after converting from one reference analyte to another can depend on how many numerical values are in the numerator and how many are in the denominator. For example, in some embodiments, each numerical value in a numerical index may be normalized to the new reference analyte in calculating the index. In some embodiments, for example, where there are equal numbers of numerical values in the numerator and denominator, conversion to a new reference analyte may have no effect on the relative numerical index between samples and/or specimen.

In the case of balanced numerical indices, the effect of a reference analyte that varies in abundance from one sample and/or specimen to another can be neutralized. This can also occur in doing bivariate analysis. In other embodiments, for example, where there are non-equal numbers of numerical values in the numerator and denominator, the relative numerical index between samples and/or specimen may change in accordance with a difference in relative numerical values for the reference analytes between the samples and/or specimen.

In some embodiments, the database is web-based. In some embodiments, the database invention finds use in experimental research, clinical diagnoses and/or drug development. For example, in some embodiments, the database can be used to advance studies on pathways of transcriptional control, and/or serve as a basis for mechanistic investigation. For example, in some embodiments, at least one numerical index indicates a biological state. Numerical indices may correlate better with a given biological state, e.g., a given phenotype, than a numerical value corresponding to an individual analyte (e.g., to an individual expressed protein). For example, in some embodiments, the numerical indices of a database described herein can be used in clinical diagnostic testing. In some embodiments, the database can be used in pharmacodynamic studies of pharmaceuticals. Such applications are described in more detail below.

IV. Applications

Another aspect of the instant invention relates to methods of using numerical values and/or numerical indices in research, diagnostic, defense and/or other applications.

A. Identification of Biomarkers

In some embodiments, methods for obtaining numerical indices are provided. In preferred embodiments, the numerical index obtained indicates a biological state. A "biological state" as used herein can refer to a phenotypic state, for e.g., a clinically relevant phenotype or other metabolic condition of interest. Biological states can include, e.g., a disease phenotype, a predisposition to a disease state or a non-disease state; a therapeutic drug response or predisposition to such a response, an adverse drug response (e.g. drug toxicity) or a predisposition to such a response, a resistance to a drug, or a predisposition to showing such a resistance, etc. In some embodiments, the drug may be and anti-tumor drug. Biological states can also include a response to a microbe and/or a response to a treatment for a microbe, as well as the biological state of the microbe itself, e.g., a state of viability of the microbe. In preferred embodiments, the numerical index obtained can act as a biomarker, e.g., by correlating with a biological state of interest. In preferred embodiments, use of embodiments of the instant invention described herein can provide personalized medicine.

In some embodiments, a method for obtaining a numerical index that indicates a biological state comprises providing 2 samples corresponding to each of a first biological state and a second biological state; measuring and/or enumerating an amount of each of 2 analytes in each of the 2 samples; providing the amounts as numerical values that are directly comparable between a number of samples; mathematically computing the numerical values corresponding to each of the first and second biological states; and determining a mathematical computation that discriminates the two biological states.

First and second biological states as used herein correspond to two biological states to be compared, such as two phenotypic states to be distinguished. Examples include, e.g., non-disease (normal) tissue vs. disease tissue; a culture showing a therapeutic drug response vs. a culture showing less of the therapeutic drug response; a subject showing an adverse drug response vs. a subject showing a less adverse response; a treated group of subjects vs. a non-treated group of subjects, etc. Examples also include, e.g., a response of a host harboring a microbe vs. a host not harboring the microbe, or harboring lesser amounts of the microbe; a favorable response of a host to a treatment for a microbe vs. a less favorable response of a host to the treatment for the microbe; and/or a viable state of a microbe vs. a less viable or non-viable state of the microbe.

A numerical index that discriminates a particular biological state, e.g., a disease or metabolic condition, can be used as a biomarker for the given condition and/or conditions related thereto. For example, in some embodiments, the biological state indicated can be at least one of an angiogenesis-related condition, an antioxidant-related condition, an apotosis-related condition, a cardiovascular-related condition, a cell cycle-related condition, a cell structure-related condition, a cytokine-related condition, a defense response-related condition, a development-related condition, a diabetes-related condition, a differentiation-related condition, a DNA replication and/or repair-related condition, an endothelial cell-related condition, a hormone receptor-related condition, a folate receptor-related condition, an inflammation-related condition, an intermediary metabolism-related condition, a membrane transport-related condition, a neurotransmission-related condition, a cancer-related condition, an oxidative metabolism-related condition, a protein maturation-related condition, a signal transduction-related condition, a stress response-related condition, a tissue structure-related condition, a transcription factor-related condition, a transport-related condition, and a xenobiotic metabolism-related condition.

For example, in specific embodiments, numerical indices that indicate lung cancer (Crawford et al., supra, (2002); Crawford et al., supra, (2060); DeMuth et al., supra, (1998)) pulmonary sarcoidosis (Rots et al., supra, (1999)), cystic fibrosis (Allen et al., supra, (1999)) and chemo-resistance in childhood leukemias (Mollerup et al., supra, (1999)) have been identified. In other specific embodiments, antioxidant and xenobiotic metabolism enzyme genes have been evaluated in human buccal epithelial cells; micro-vascular endothelial cell gene expression has been associated with scleroderma progression; membrane transport genes expression has been studied in rat congestive heart failure models; immune resistance has been studied in primary human tissues; transcription control of hormone receptor expression has been studied; and gene expression patterns have been associated with carboplatin and/or taxol resistance in ovarian carcinoma and with gemcitabine resistance in multiple human tumors. Other specific examples include, e.g., identification of numerical indices for predicting responsiveness of colon cancer to 5-FU and for indicating one or more different stages of bladder carcinoma. Embodiments of inventions described herein can accelerate discovery of associations between gene expression patterns and biological states of interest, leading to better methods for preventing, diagnosing and treating various conditions.

Assessing amounts of analytes may be performed by any methods known in the art and/or described herein. Preferably, the method used can detect and/or quantify less than about 10,000, less than about 8,000, less than about 6,000, less than about 4,000, less than about 1,000, less than about 800, less than about 600, less than about 400, less than about 100, less than about 60, less than about 30, less than about 10, less than about 6, less than about 3 molecules, or about 1 molecule of a given analyte in a given sample. In some embodiments, the measurements correspond to gene expression measurements, e.g., levels of mRNA transcripts and/or expressed proteins can be measured. In preferred embodiments, one or more methods and/or compositions provided herein permit detection and/or quantification of low copy numbers of proteins and/or mRNA transcripts, e.g., with one or more of the sensitivities, one or more of the specificities, one or more of the robustness, one or more of the accuracies, one or more of the detection limits, and/or with one or more of the coefficients of variation taught herein. Without being limited to a particular hypothesis and/or theory, standardized quantification of small amounts of various molecular materials (e.g., proteins, nucleic acids, small molecules) can increase the predictive abilities of biomarkers obtained. Such biomarkers find use in early and/or more accurate diagnoses, e.g., as discussed in more detail below.

In some embodiments, one or more of the analytes assayed are associated with one of the biological states to a greater degree than the other(s). For example, in some preferred embodiments, one or more of the analytes to be evaluated is associated with a first biological state and not with a second biological state. An analyte may be said to be "associated with" a particular biological state where the analyte is either positively or negatively associated with the biological state. For example, an analyte may be said to be "positively associated" with a first biological state where the analyte occurs in higher amounts in a first biological state compared to a second biological state. As an illustration, proteins highly expressed in cancer cells compared to non-cancer cells can be said to be positively associated with cancer. On the other hand, e.g., a small molecule metabolite present in lower amounts in a first biological state compared to a second biological state can be said to be negatively associated with the first biological state.

The analyte to be detected and/or quantified may correspond to a gene associated with a particular phenotype, e.g., corresponding to the transcribed, expressed, and/or regulatory regions of the gene (e.g., a regulatory region of a transcription factor, e.g., a transcription factor for co-regulation). In preferred embodiments, expression levels, in particular, mRNA and/or protein levels of 2 or more genes, can be used to indicate a biological state. For example, microarray analysis has identified gene sets that are associated with disease states and/or drug responses (Wigle et al., *Cancer Res.* 62, 3005-3008 (2002); Garber et al., *Proc. Natl. Acad. Sci. USA* 98, 13784-13789 (2001); Bhattacharjee et al., *Proc. Natl. Acad. Sci. USA* 98, 13790-13795 (2001); Hedenfalk et al., *New Engl. J. Med.* 344, 539-548 (2001); Sorlie et al., *Proc. Natl. Acad. Sci. USA* 98, 10869-10874 (2001); Perou et al., *Proc. Natl. Acad. Sci. USA* 96, 9212-9217 (1999)). Providing the measured and/or enumerated amounts as numerical values is preferably accomplished by one or more embodiments of the methods described herein, where the numerical values are directly comparable for a number of samples used, within one or more of the co-efficients of variation provided herein, and/or with one or more of the sensitivities, one or more of the specificities, one or more of the robustness, one or more of the accuracies, and/or one or more of the detection limits taught herein, for different analytes, including between non-nucleic acid analytes and nucleic acid analytes.

In some embodiments, expressed amounts of more than 2 genes are assessed and used to provide a numerical index indicative of a biological state. For example, in some cases, expression patterns of about 50 to about 100 genes are used to characterize a given phenotypic state, e.g., a clinically relevant phenotype. See, e.g., Heldenfalk, I. et al., supra, (2000).

In some embodiments of the instant invention, expressed amounts of at least about 5 genes, at least about 10 genes, at least about 20 genes, at least about 50 genes, or at least about 70 genes may be assessed and used to provide a numerical index indicative of a biological state. In some embodiments of the instant invention, expressed amounts of less than about 90 genes, less than about 100 genes, less than about 120 genes, less than about 150 genes, or less than about 200 genes may be assessed and used to provide a numerical index indicative of a biological state. Specific examples of several of these embodiments include, e.g., identification of gene expression patterns associated with lung cancer (Crawford et al., supra, (2000); DeMuth et al., supra, (1998); pulmonary sarcoidosis (Allen et al., supra, 1999); cystic fibrosis (Allen et al., supra, 1999); and chemoresistance in childhood leukemias (Rots et al., supra, (1999); Rots et al., supra, (2000)). In some embodiments, amounts of 2 or more analytes, including at least one non-nucleic acid analyte are used in computing a numerical index, e.g., a numerical index indicative of a biological state.

Mathematically computing numerical values can refer to using any equation, operation, formula and/or rule for combining and/or interacting numerical values, e.g., a sum, difference, product, quotient, log power and/or other mathematical computation. As described above, in some embodiments, a numerical index is calculated by dividing a numerator by a denominator, where the numerator corresponds to an amount of one analyte and the denominator corresponds to an amount the another analyte. In preferred embodiments, the numerator corresponds to an analyte positively associated with a given biological state and the denominator corresponds to an analyte negatively associated with the biological state. In preferred embodiments, at least one of the analytes comprises a non-nucleic acid analyte. In some embodiments, more than one analyte positively associated with the biological state being evaluated and more than one analyte negatively associated with the biological state being evaluated can be used. For example, in some embodiments, a numerical index can be derived comprising numerical values for the positively associated analytes in the numerator and numerical values for an equivalent number of the negatively associated analytes in the denominator. As mentioned above, in such balanced numerical indices, numerical values corresponding to a reference nucleic acid cancel out. An example of a balanced numerical index includes a numerical index for predicting anti-folate resistance among childhood leukemias. Rots et al., supra, (2000). In some embodiments, balanced numerical values can neutralize effects of variation in abundance of the reference analyte(s). In some embodiments, a numerical index is calculated by a series of one or more mathematical functions.

Determining which mathematic computation to use to provide a numerical index indicative of a biological state may be achieved by any methods known in the arts, e.g., in the mathematical, statistical, and/or computational arts. In some embodiments, determining the mathematical computation involves a use of software. For example, in some embodiments, a machine learning software can be used.

In some embodiments, more than one sample corresponding to each biological state can be provided. For example, at least about 5 samples, at least about 10 samples, at least about 50 samples, at least about 100 samples, at least about 500 samples, at least about 1,000 samples, at least about 5,000 samples, at least about 10,000 samples, at least about 50,000 samples, at least about 100,000 samples, at least about 500,000 samples, at least about 1,000,000 samples, at least about 5,000,000 samples, or at least about 10,000,000 samples (corresponding to one or more of the biological states of interest) may be provided.

In some embodiments, more than 2 biological states can be compared, e.g., distinguished. For example, in some embodiments, samples may be provided from a range of biological states, e.g., corresponding to different stages of disease progression, e.g., different stages of cancer. Cells in different stages of cancer, for example, include a non-cancerous cell vs. a non-metastasizing cancerous cell vs. a metastasizing cell from a given patient at various times over the disease course. Cancer cells of various types of cancer may be used, including, for example, a bladder cancer, a bone cancer, a brain tumor, a breast cancer, a colon cancer, an endocrine system cancer, a gastrointestinal cancer, a gynecological cancer, a head and neck cancer, a leukemia, a lung cancer, a lymphoma, a metastases, a myeloma, neoplastic tissue, a pediatric cancer, a penile cancer, a prostate cancer, a sarcoma, a skin cancer, a testicular cancer, a thyroid cancer, and a urinary tract cancer. In preferred embodiments, biomarkers can be developed to predict which chemotherapeutic agent can work best for a given type of cancer, e.g., in a particular patient or particular group of patients. A non-cancerous cell may include a cell of hematoma and/or scar tissue, as well as morphologically normal parenchyma from non-cancer patients, e.g., non-cancer patients related or not related to a cancer patient. Non-cancerous cells may also include morphologically normal parenchyma from cancer patients, e.g., from a site close to the site of the cancer in the same tissue and/or same organ; from a site further away from the site of the cancer, e.g., in a different tissue and/or different organ in the same organ-system, or from a site still further away e.g., in a different organ and/or a different organ-system.

Numerical indices obtained can be provided as a database, e.g., as detailed above. Numerical indices, numerical values, and/or databases thereof can find use in diagnoses, e.g. in the development and application of clinical tests, as described below.

B. Diagnostic Applications

In some embodiments of the instant invention, a method of identifying a biological state is provided. In some embodiments, the method comprises detecting and/or quantifying an amount of one or more analytes in a sample and providing the amounts as numerical values, whereby the numerical value indicates the biological state. Some embodiments further comprise using numerical values corresponding to each of 2 or more of the analytes to provide a numerical index, whereby the numerical index indicates the biological state.

A numerical value that indicates a biological state can be determined as described above in accordance with one or more various embodiments of the instant invention. A numerical index that indicates a biological state can be determined as described above in accordance with one or more various embodiments of the instant invention. The sample may be obtained from a specimen, e.g., a specimen collected from a subject to be treated. The subject may be in a clinical setting, including, e.g., a hospital, office of a health care provider, clinic, and/or other health care and/or research facility. Analytes of interests in the sample can then be assayed using one or more of the methods and/or compositions provided herein.

In some embodiments, numerical values and/or numerical indices obtained from a sample can be compared to a database, e.g., a database described herein. Comparison can facilitate clinical diagnosis, e.g., by correlating a numerical value and/or numerical index with a biological state, such as a disease phenotype, expected prognosis, likelihood of favorably responding to a given treatment, etc. For example, by comparing the expression pattern of genes from a tumor to those in a database, a chemotherapeutic agent can be selected to which the tumor would most likely respond.

In preferred embodiments, one or more methods and/or compositions provided herein permit detection and/or quantification of low abundance analytes, with one or more of the sensitivities, one or more of the specificities, one or more of the robustness, one or more of the accuracies, one or more of the detection limits, and/or with one or more of the coefficients of variation taught herein. Preferably, the method used can detect and/or quantify less than about 10,000, less than about 8,000, less than about 6,000, less than about 4,000, less than about 1,000, less than about 800, less than about 600, less than about 400, less than about 100, less than about 60, less than about 30, less than about 10, less than about 6, less than about 3 molecules, or about 1 molecule of a given analyte in a given sample.

In some embodiments, one or more methods and/or compositions provided herein permit earlier detection of a biological state, e.g., a disease phenotype, facilitating earlier diagnosis. For example, early detection of cancer can be accomplished through early detection of associated serum proteins, e.g., transcription and/or expression products of one or more oncogenes. Other examples include early detection of carcinoembryonic antigen (CEA) and tumor necrosis factor. See, e.g., Ren et al., supra, (2001) and Komatsu et al., supra, (2001). Early detection of other proteins associated with other disease phenotypes similarly can facilitate earlier diagnosis.

For example, in some embodiments, diagnosis, prognosis, choice of treatment and/or risk for a disease phenotype, etc., may be assessed by measuring serum concentration of, e.g., PSA, HBsAg, TNF-α, carcinoma-associated Ag, insulin, cholesterol, Fe gamma RIIIa, homodimeric osteo-protegerrin, CA125 and/or other species associated with a particular disease. For example, low detection threshold of some embodiments of the instant invention may permit detection and/or quantitation of PSA levels after a prostatectomy or a radical prostatectomy. In still some embodiments, diagnosis, prognosis, choice of treatment, and/or risk for a disease phenotype, etc., may be assessed by measuring serum concentration of, e.g., coxsackie virus B, Salmonella, Helicobacter pylori and/or Clostridium botulinum neurotoxin Type A. For example, detection of low amounts of a toxin can indicate toxic exposure at an early stage.

Standardized quantification of small amounts of various molecular materials (e.g., proteins, nucleic acids, small molecules) can increase predictive ability for diagnosis. Without being limited to a particular theory and/or hypothesis, more than one type of molecular material may be associated with a given biological state, and thus methods for detecting and/or quantifying different materials can provide predictive advantages.

For example, pathogenic infection by a microbe may be indicated by the presence of the microbe in conjunction with certain expressed levels of microbial genes, e.g., indicating the microbe's viability. Some embodiments can provide methods, compositions and/or kits for assaying for the microbe itself along with one or more nucleic acids corresponding to such microbial genes. Where the microbe itself is assayed as an analyte, any structure of the microbe may be detected and/or quantified, including, e.g, any antigenic structure of the microbe. Antigenic structures can include, e.g, the protein coat of a virus, cell wall of a bacterium, spores of a fungus, and the like, as well as, in some embodiments, toxin produced by the microbe, e.g. Clostridium botulinum neurotoxin. Wu et al., supra, (2001). Genes indicating the microbe's viability include any gene transcribed and/or expressed in the performance of biological activities of the microbe. In preferred embodiments, a microbial gene indicating viability preferably indicates decreased viability in response to an administered treatment, e.g., a drug administered against the microbe.

In some embodiments, pathogenic infection by a microbe may be indicated by the presence of the microbe in conjunction with certain expressed levels of host genes, e.g., indicating the host's response to the microbe. Some embodiments can provide methods, compositions and/or kits for assaying the microbe itself along with one or more nucleic acids corresponding to such host genes. "Host" as used herein can refer to any biological entity harboring a microbe, including, e.g., a patient or subject in a clinical trial; an in vitro culture of mammalian cells, or a laboratory animal used in drug development. A host response to the microbe may include, e.g., antibodies, cytokines, and/or other products expressed or expressed at higher levels as part of the host's immune response. Assaying mRNA and/or protein levels of antibodies, cytokines or other analytes produced in response to the microbe, e.g., can help confirm diagnosis and/or indicate subsequent treatment(s) desirable.

In some embodiments, host response to treatment of a microbe may be evaluated, e.g., where host response is indicated by certain expressed levels of host genes. For example, some embodiments provide methods, compositions and/or kits for assaying a microbe itself along with one or more nucleic acids corresponding to such host genes. For example, a host response to treatment may be a therapeutic drug response or predisposition to such a response, an adverse drug response (e.g. drug toxicity) or a predisposition to such a response, a resistance to a drug, or a predisposition to showing such a resistance, e.g., as described above. Such information can aid the decision as to whether to continue, discontinue, and/or modify treatment, as well as which other treatment(s) to administer.

In some embodiments, levels of administered drugs and/or metabolites thereof can be evaluated. For example, small molecules corresponding to break down products of a drug can be assayed, e.g., to evaluate bioavailability, pharmacokinetics, distributions, and/or other pharmacodynamic parameters of the drug. Such information can also aid the decision as to whether to continue, discontinue, and/or modify treatment, as well as which other treatment(s) to administer.

In cases where several analytes are to be assayed in a sample and/or specimen, preferred embodiments can be practiced using small amounts of starting material, e.g., using the amounts of material obtained from a diagnostic biopsy sample or any other samples described herein. Use of smaller amounts of samples can in turn facilitate lower reagent consumption, and/or reduce costs.

In preferred embodiments, more than one analyte can be evaluated at the same time, and in more preferred embodiments, where a given number of analytes are to be evaluated, data for that given number of analytes can be obtained simultaneously. In even more preferred embodiments, different analytes comprise different molecular materials, including, e.g., at least one non-nucleic acid analyte, and the different analytes are assayed simultaneously. For example, methods, compositions and/or kits described herein can provide for simultaneous measurement in a given sample of one or more microbes, one or more genes indicating viability of the microbe(s), one or more gene indicating host response to the microbe(s), one or more genes indicating host response to a treatment of the microbe(s), and/or one or more drugs and/or metabolites thereof.

In some embodiments, methods, compositions and/or kits of the instant invention can provide clinical diagnostic tests amenable to quality-control. For example, measurement of an analyte relative to its respective internal standard within a standardized mixture can provide quality-controlled results, e.g., within one or more of the sensitivities, one or more of the specificities, one or more of the robustness, one or more of the accuracies, one or more of the detection limits, and/or one or more of the coefficients of variation taught herein.

C. Drug Development

Methods, compositions and/or kits of the instant invention can be used in drug development. For example, in some embodiments, a candidate drug and/or its metabolites can be detected and/or quantified with one or more of the sensitivities, one or more of the specificities, one or more of the robustness, one or more of the accuracies, one or more of the detection limits, and/or with one or more of the coefficients of variation taught herein, e.g., to evaluate bioavailability, pharmacokinetics, distributions, and/or other pharmacodynamic parameters of the drug. Some embodiments of the instant invention permit more detailed understanding of drug distribution in bodily fluids and/or tissues, e.g., any of the biological fluids and/or tissues detailed above.

Standardized quantification of small amounts of various molecular materials (e.g., proteins, nucleic acids, small molecules) can provide pharmacodynamic information as well as information on the response produced by the drug e.g., responses of drug targets. Such data can provide information, e.g., on how much of a candidate drug reaches various tissues as well as the effects of the candidate drug on those tissues. For example, response to the drug can be indicated by increased or decreased expression of mRNA transcripts and/or of protein products of one or more genes, e.g., genes that are targets of the drug. Some embodiments of the instant invention provide methods, compositions and/or kits for assaying a drug (and/or a metabolite thereof) in conjunction with one or more nucleic acids corresponding to such target genes. Such embodiments, e.g., can facilitate measurement of drug levels along with changes in expression of genes that are targets of the drug. Such information can aid in drug development, e.g., to determine whether to therapeutic or adverse effects are produced, e.g., by different dosages of the drug, e.g., in various tissues. In preferred embodiments, the drug (and/or metabolite thereof) and gene products (transcripts and/or proteins) can be assayed at the same time, e.g., measured from a given sample simultaneously.

D. Detection of Biological and/or Chemical Warfare Agents

In some embodiments of the instant invention, methods compositions and/or kits are provided, for detecting an agent of biological and/or chemical warfare. An agent of biological and/or chemical warfare can include any biological and/or chemical entity that can be used as a weapon, e.g., to cause terror, chaos, disease, discomfort and/or death. Such agents can include, e.g., but are not limited to agents for anthrax, small pox, tularemia, plague, HIV, ebola, foot and mouth disease, as well as ricin, cyanide, vesicants (or blister agents) such as mustard gas and Lewisite, choking agents, such as chlorine and phosgene, nerve agents, such as sarin and VX, hallucinogens, such as BZ, and/or derivatives thereof and/or any combinations thereof.

In some embodiments, one or more methods, compositions and/or kits provided herein permit detection and/or quantification of low amounts of one or more biological and/or chemical warfare agents with one or more of the sensitivities, one or more of the specificities, one or more of the robustness, one or more of the accuracies, one or more of the detection limits, and/or one or more of the coefficients of variation taught herein, e.g., using reagents providing one or more of the stabilities described herein. Preferably, the assay provided can detect and/or quantify less than about 10,000, less than about 8,000, less than about 6,000, less than about 4,000, less than about 1,000, less than about 800, less than about 600, less than about 400, less than about 100, less than about 60, less than about 30, less than about 10, less than about 6, less than about 3 molecules, or about 1 molecule of a given biological and/or chemical warfare agent in a given sample. In more preferred embodiments, assays can be performed using small amounts of starting material, e.g., small amounts of specimen and/or samples suspected of contamination, including, e.g. soil samples, crop materials, aerosols, water supplies, food or ingredients for consumption, microbial habitats, and/or other materials of environmental, industrial, medical, military, nutritional, and/or veterinary significance, e.g., as described above.

Standardized quantification of small amounts of various molecular materials (e.g., proteins, nucleic acids, small molecules) can permit different types of biological and/or chemical warfare agents to be assayed in a given sample. In preferred embodiments, more than one biological and/or chemical warfare agent can be assayed for at the same time; and in more preferred embodiments, the different agents comprise different molecular materials, including at least one non-nucleic acid analyte, and the different agents are assayed for simultaneously. For example, some embodiments provide kits comprising standard mixtures of internal standards for at least about 2, at least about 5, at least about 10, at least about 50, at least about 100, at least about 200, at least about 500 or at least about 1,000 different biological and/or chemical warfare agents.

In some embodiments, exposure to a biological and/or chemical warfare agent can be assayed. For example, a subject's exposure to a noxious substance can be indicated by increased or decreased expression of mRNA transcripts and/or of protein products of one or more genes, e.g., genes that are targets of the agent. Some embodiments of the instant invention provide methods, compositions and/or kits for assaying an agent of biological and/or chemical warfare (and/or a metabolite thereof) in conjunction with one or more nucleic acids corresponding to such target genes. Such embodiments, e.g., can facilitate detection of the agent along with changes in expression of genes that are targets of the agent. In preferred embodiments, the biological and/or chemical warfare agent (or metabolite thereof) and gene products (transcripts and/or proteins) can be assayed for at the same time, e.g., measured from a given sample simultaneously.

EXAMPLES

Example I

The Following Example Illustrates Assaying Carcinoembryobic Antigen (CEA) with α-Fetoprotein (AFP) as a Reference, in Accordance with Some Embodiments of the Invention Preparation of Immobilized Receptors on a Thermocycler/Immunoassay Plate Monoclonal antibodies for CEA (anti-CEA) and AFP (anti-AFO) can be used as receptors for CEA and AFP sample analytes, and their corresponding internal standards. The high affinity monoclonal antibodies (mAbs) are commercially available from Fitzgerald Industries International Inc. (Concord, Mass.). The mAbs for CEA and AFP can each be diluted in carbonate-bicarbonate buffer (Sigma C3041) at 50 μg/ml and applied to wells of the first row of three TopYield strips. The mAbs can be serially diluted (1:2) down each column and the last row left containing only buffer. The mAbs can be allowed to bind to the plate by incubating overnight at 4° C.

The wells can be washed three times with Phosphate Buffered Saline, pH 7.4 (Sigma P3813) containing 0.1% Tween 20 (PBST). Unbound sites can be blocked. A variety of blocking agents can be used, including 5% non-fat milk (Sigma P4739), gelatin (Sigma, G8150) and Phosphate Buffered Saline (PBS) with bovine serum albumin (BSA), pH 7.4 (Sigma, P3688) containing 0.1% Tween 20 (PBST-BSA). The desired blocking agent can be applied to the plates for two hours at 37° C. Wells can then be washed with PBST three times.

Receptor binding can be detected by the addition of a 1:3000 dilution of goat anti-mouse IgG1 horse radish peroxidase (HRP) (Southern Biotech, 1070-05), followed by an incubation for 1 hour at 37° C. Plates can then be developed by the addition of o-phenylene diamine (OPD) in the appropriate buffer and the absorbance of the wells read at 465 nm. Absorbance can be plotted against concentration of mAbs and the optimal binding conditions determined for anti-CEA and anti-AFP (i.e. the lowest concentration of each mAb that yields maximal binding and lowest background).

In some experiments, receptors for both CEA and AFP can be immobilized per TopYield™ well. Differences in attachment of the different receptors can be determined as follows. 10 μg of anti-CEA and anti-AFP can be biotinylated using EZ-Link™ Sulfo-NHS-LC-Biotin (Pierce, Rockford, Ill.) according to the directions supplied by the manufacturer. The biotinylated mAbs can be dialyzed against PBS to remove any un-reacted biotin.

One set of TopYield™ strips can be coated with biotin-anti-CEA and anti-CEA and one set of strips with anti-AFP and biotin-anti-AFP. The mAbs can be serially-diluted to achieve a checkerboard dilution scheme, i.e. one mAb can be diluted across the plate and the other mAb can be diluted down the plate. The plate can be blocked and washed as described above. Immobilization of each mAb can be detected by applying a 1:3000 dilution of streptavidin-HRP (Southern-Biotech, Birmingham, Ala.) and developing color as described above. A plot of mAb concentration against OD can determine the appropriate concentration of each mAb for suitable coating purposes.

Selection of Tas and Corresponding Competitive Templates for CEA and AFP

Native template (NT) for β-actin can be used for tagging sample CEA, while the competitive template (CT) for β-actin can be coupled to CEA used as the internal standard. Native template for catalase can be used for tagging sample AFP, while the competitive template for catalase can be coupled to AFP used as the internal standard. NTs and CTs are available at www.geneexpressinc.com.

Preparation of Conjugated Antibodies

Different methods for conjugating DNA to antibodies, for preparing internal standards and/or for tagging sample analytes, can be used and the binding efficiencies of the conjugated antibodies assessed as follows.

SPR analysis can be performed using a BIAcore 3000 instrument with a computer interface for system control and data acquisition (BIAcore AB, Uppsala, Sweden). Experiments can be conducted at 25° C. with a flow rate of 10 μl/min and with HBS-EP (0.01 M HEPES pH 7.4, 0.15 M NaCl, 3 mM EDTA, 0.005% Surfactant P20) as the running buffer.

Figure 7:
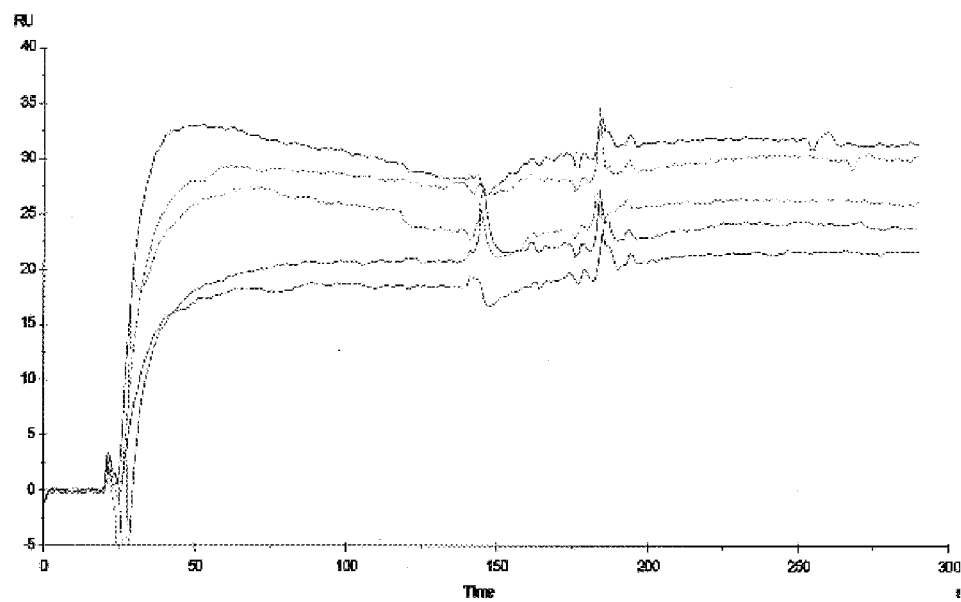
FIG. 7 illustrates results demonstrating the utility of SPR in determining binding affinities for monoclonal antibodies.

FIG. 7 illustrates results demonstrating the utility of SPR in determining binding affinities for monoclonal antibodies. The binding affinity of mAb PN31-1 was evaluated, which has specificity for the pneumococcal polysaccharide-conjugate, Type 4 (PPS4) (Wyeth, Rochester, N.Y.), ranging from 33 nM to 133 nM. PPS4 is known to bind recombinant human Heparin-Binding Epidermal Growth Factor (HB-EGF). To demonstrate the applicability of SPR techniques, recombinant human HB-EGF (R&D Systems, Minneapolis, Minn.) was diluted to 25 μg/ml in Borate Buffer pH 8.5 and immobilized to the surface of a CM5 sensor chip (BIAcore AB, Uppsala, Sweden) using standard amine coupling chemistry. PPS4 was diluted to 50 μg/ml in running buffer and injected over the surface for 2 min., allowing capture by HB-EGF and producing no change in refractive index. Dilutions of mAb PN31-1 were then injected for 2 min. to determine the binding affinity of the mAb. PN31-1 was titrated at concentrations of 33, 47, 67, 100 and 133 nM. Regeneration was achieved by injection of 0.5% SDS for 5 min. Data was analyzed using BIAevaluation Software 3.0 (BIAcore AB, Uppsala, Sweden) and a bivalent analyte model. The analysis of data using this model is appropriate when the antigen is immobilized and the analyte has two binding sites. Based on a series of overlay sensograms, preliminary results indicated that the $K_D$ of PN31-1 is 100 pM.

A similar technique can be used with the anti-CEA and anti-AFP mAbs. Briefly, CEA or AFP antigens can be diluted to various concentrations of 5-100 g/ml in 10 mM sodium acetate pH 5.0 and immobilized on the surface of a CM5 sensor chip (BIAcore AB, Uppsala, Sweden) using standard amine coupling chemistry. Dilutions of the mAbs, either conjugated or unconjugated, ranging from 100 μM to 1 mM can then be injected for 2 min. to determine the binding affinity of the mAbs. Regeneration can be achieved by injection of glycine-HCl pH 2.5 for 5 min. Data can be analyzed using BIAevaluation Software 3.0 (BIAcore AB, Uppsala, Sweden) and a bivalent analyte model. All flow rates, injection times and regeneration conditions can be improved or optimized as necessary.

Preparation of Internal Standards

Internal standards for CEA and AFP analytes can be prepared by combining solutions containing the following. For CEA, anti-CEA conjugated to DNA corresponding to CT for β-actin is combined with CEA. For AFP, anti-AFP conjugated to DNA corresponding to CT for catalase is combined with AFP. The molarities of the solutions can be calculated to determine that mAb-CT conjugates can be saturated with antigen (Ag). The known molecular weights (kDa) are: CEA 180, AFP=70, anti-CEA=146, anti-AFP=146, 100 bp DNA fragment=66, 300 bp DNA fragment 198. The concentration of antigen that is 10M excess compared to its antibody conjugate can be calculated. The antigen and mAb-CT solutions can be combined and mixed overnight at 4° C.

The Ag-mAb-CT complexes can then be purified by utilizing gel filtration chromatography with Sephacryl®400-HR (Sigma, S400HR). To test that there is neither free mAb-CT nor free Ag in solution, SPR technology can again be used. To determine whether there is free mAb-CT in solution, a chip surface can be coated with Ag as described above. In the absence of free mAb-CT, a binding signal should not be detected, as all mAb-CT will be bound to Ag in solution. To determine the presence of free Ag in solution, a chip surface can be coated with mAb, essentially as described above. In the absence of free Ag, a binding signal should not be detected, as all Ag will be bound to mAb-CT in solution.

Comparison of Binding of Ag-mAb-CT and Free Ag to Immobilized Receptors

Binding affinities of Ag-mAb-CT relative to free antigen for forming complexes with immobilized receptors can be determined using SPR technology. The method used can be similar to that outlined above, with some modifications. For example, anti-CEA or anti-AFP can be diluted to various concentrations between 5-100 µg/ml in 10 mM sodium acetate pH 5.0 and immobilized to the surface of a CM5 sensor chip (BIAcore AB, Uppsala, Sweden) using standard amine coupling chemistry. A serial dilution of Ag relative to Ag-mAb-CT, ranging from 100 µM to 1 mM, can then injected for 2 minutes to determine the binding affinity of the antigen or Ag-mAb-CT complexes to immobilized antibody.

Initial Assessment of Prepared Reagents

Known quantities of internal standard Ag-mAb-CT and free Ag, in varying amounts relative to each other, can be applied to the plates prepared above with immobilized receptors. Following a wash, a saturating amount of mAb-NT conjugates can be added, followed again by washing. NT and CT for each antigen can be co-amplified and relative amounts of the amplified products determined, as described herein. This can allow determination of how the Ag-mAb-CT and free Ag titrate relative to each other based on varying CT: NT ratios obtained. A 100% sensitivity (i.e., signal changing to the same extent as the amount the analyte changes) can be observed.

As a negative control, the experiment can be carried out as described above, but on a surface without bound receptors. The negative control will indicate whether Ag-mAb-CT or Ag bind non-specifically to the surface or if they can be removed by washing, and if no, do they bind in proportion to their representation in the solution.

Assay of Unknown Amount of CEA in Blood Sample

Blood or serum samples can be collected from patients, preferably where some samples are expected to contain CEA and others would not be expected to contain CEA. The samples can be serially diluted with known amounts of internal standard Ag-mAb-CT for CEA and AFP (containing known numbers of molecules of the internal standards). The dilutions can be applied to the plates prepared with immobilized receptors. Following a wash, a saturating amount of. mAb-NT conjugates for CEA and for AFP can be added, followed again by washing. NT and CT for each antigen can be co-amplified and relative amounts of the amplified products determined, as described herein. This can indicate that the methods are robust in the context of complex protein-rich mixtures, such as those of blood samples, e.g., with limited non-specific binding of proteins in the mixture to reagents or to the surface. The assay can be repeated using various dilutions of serum samples to improve such robustness.

Example II

The Following Example Provides Additional Details of an Overall Process of Evaluating Gene Expression Measurements that can be Used with Some Embodiments of the Instant Invention Materials 1. Standardized RT-PCR reagents, including primers and standardized mixtures are purchased from Gene Express, Inc. (GEI, Toledo, Ohio).

2. Buffer for Idaho Rapidcycler air thermocycler: 500 mMTris-HCl, pH 8.3, 2.5 µg/µL, BSA, 30 mMMgCl$_2$ (Idaho Technology, Inc., Idaho Falls, Id.).

3. Buffer for block thermocyclers, Thermo 10×, 500 mM KCl, 100 mM Tris-HCl, pH 9.0, 1.0% Triton X-100 (Promega, Madison, Wis.).

4. Taq polymerase (5 U/µL), Moloney Murine Leukemia Virus (MMLV) reverse transcriptase, MMLV RT 5× first strand buffer: 250 mM Tris-HCl, pH 8.3, 375 mMKCl, 15 mM MgCl$_2$, 50 mM dithiothreitol, oligo dT primers, Rnasin, pGEM size marker, and deoxynucleotide triphosphates (dNTPs) also are obtained from Promega.

5. TriReagent is obtained from Molecular Research Center, Inc. (Cincinnati, Ohio).

6. Ribonuclease (Rnase)-free water and TOPO TA cloning kits are obtained from Invitrogen (Carlsbad, Calif.). The quality of the RNase-free water can be important for the efficient extraction of intact RNA. For example, inadequate DEPC treatment and/or inadequate removal of DEPC after treatment can inhibit reverse transcription and PCR.

7. GigaPrep plasmid preparation kits are purchased from Qiagen (Texas).

8. Caliper AMS 90SE chips are obtained from Caliper Technologies, Inc. (Mountain View, Calif.).

9. DNA purification columns are obtained from QiaQuick (Qiagen, Valencia, Calif.).

RNA Extraction and Reverse Transcription

RNA Extraction: Cell suspensions can be pelleted, the supernatant poured off, and the pellet dissolved in TriReagent and extract (according to manufacturer's instructions and previously described methods, see, e.g., Bustin, et al., *J. Mol. Endorinol.* 25, 169-193 (2000). The RNA pellet can be stored under ethanol at −80° C., or suspended in RNAse free water and frozen at −80° C. It may be stored in this condition for years. The quality of the RNA can be evaluated on an Agilent 2100 using the RNA chip, according to manufacturer's instructions.

Reverse Transcription: 1 µg total RNA can be reverse transcribed using MMLV RT and an oligo dT primer as previously described. See, e.g., Willey et al., *Am. J. Respir. Cell Mol. Biol.* 17, 114-124 (1997). For small amounts of RNA (e.g. less than about 100 ng), the efficiency of reverse transcription may be improved with using Sensicript™ rather than MMLV reverse transcriptase, e.g., efficient reverse transcription may be obtained about 50 ng of RNA with Sensiscript™. The reaction can be incubated at 37° C. for 1 h.

Synthesis and Cloning of Competitive Templates

Internal standard competitive templates (CTs) can be constructed based on previously described methods. See, e.g., Willey et al., supra, (1998); Crawford et al., supra, (1997); Celi et al., supra, (1993).

Native Template Primer Design

Before a CT for a gene is constructed, a primer pair can be designed that amplifies (preferably, efficiently amplifies) native cDNA corresponding to the expressed gene. For example, primers can be designed with one or more of the following characteristics: (1) an ability to amplify from about 200 to about 850 bases of the coding region of genes of interest; (2) an annealing temperature of about 58° C. (tolerance of +/−1° C.). Primer 3.1 software (Steve Rozen, Helen J. Skaletsky, 1996, 1997) Primer 3 can be used to design the primers (code available at http://www-genome.wi.net.edu/genome_software/other/primer3.html) in some embodiments. Primers were initially designed using Primer 3.1 software to amplify from about 200 to about 800 bases of the coding region of targeted genes with an annealing temperature of about 58° C. (tolerance of +/−about 1° C.). This allowed the PCR reactions in this example to be run under identical or nearly identical conditions and further allows for automation and high throughput applications, including microfluidic capillary gel electrophoresis. For example, primer sequences and Genbank accession numbers for genes certain genes are available at www.geneexpressinc.com. Primers can also be designed to amplify from about 20 to about 2,000 bases, in other examples.

Native Template Primer Testing

Designed primers can be synthesized and used to amplify native template of cDNA corresponding to the gene(s) of interest. The presence of a single strong band after 35 cycles of PCR can verify that the primers are sufficiently efficient and/or specific for some embodiments. For example, primers can be tested using reverse transcribed RNA from a variety of tissues and/or cDNA clones known to represent the gene(s) of interest. In some embodiments, primer pairs that fail to amplify the target gene in any tissue or individual cDNA clone, e.g., less than about 10% of the time, can be redesigned and the process repeated.

Competitive Template Primer Design

Figure 8:
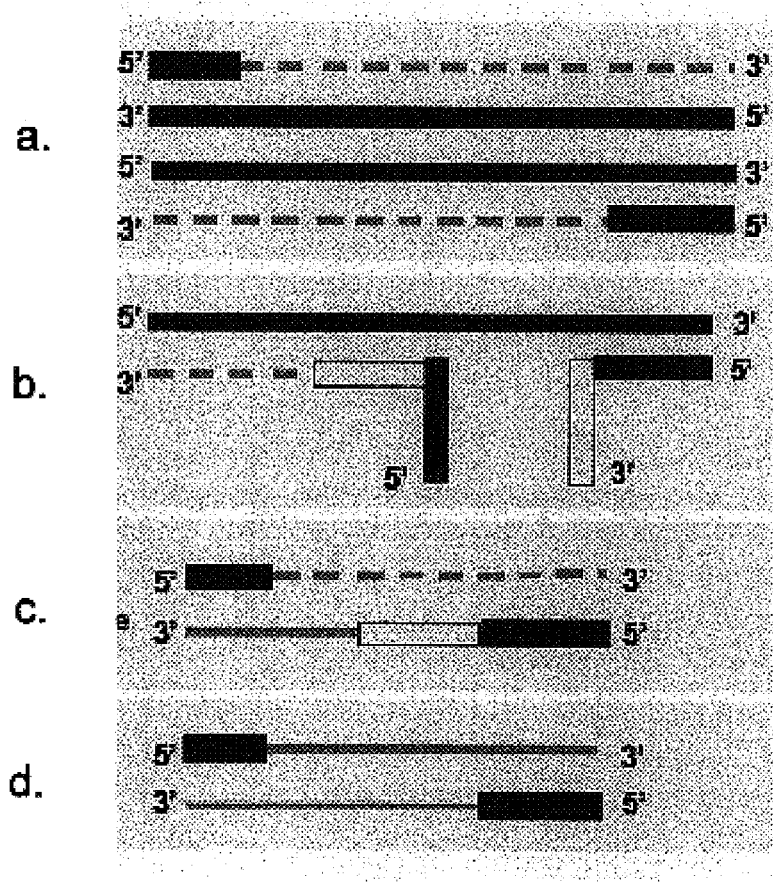
FIG. 8a illustrates Forward (striped bar) and reverse (black bar) primers (approx 20 bp in length) that span a 150-850 by region can be used to amplify the native template (NT) from cDNA.
FIG. 8b illustrates that after testing that native template primers work, a CT primer can be designed to be about 40 bp primer with the sequence for the reverse primer (black bar) at the 5'end, and a 20 bp sequence homologous to an internal native template sequence (white bar) at the 3'end, collinear with the reverse primer sequence.
FIG. 8c illustrates that in the next PCR cycle, the DNA newly synthesized using the about 40 bp primer hybridized to the internal sequence can be bound to forward primer (striped bar), and a homologous strand can be synthesized.
FIG. 8d illustrates that this can generate a double stranded CT with the reverse primer sequence about 100 bp closer to the forward primer than occurs naturally in the NT.

A CT primer can be prepared according to previously described methods and/or as illustrated in FIG. 8. FIG. 8a illustrates Forward (striped bar) and reverse (black bar) primers (approx 20 bp in length) that span a 150-850 bp region can be used to amplify the native template (NT) from cDNA. Taq polymerase can synthesize DNA from these primers (dashed lines) using the NT.

FIG. 8b illustrates that after testing that native template primers work, a CT primer can be designed to be about 40 bp primer with the sequence for the reverse primer (black bar) at the 5' end, and a 20 bp sequence homologous to an internal native template sequence (white bar) at the 3' end, collinear with the reverse primer sequence. The 3' end of this 40 bp primer can be designed to be homologous to a region about 50 to about 100 bp internal to the reverse primer. The 5' end of this about 40 bp primer can hybridize to the region homologous to the reverse primer, while the 3' end can hybridize to the internal sequence. Furthermore, Taq polymerase can synthesize DNA using the primers bound at the 3' end (dashed line) and not the primer bound at the 5' end.

FIG. 8c illustrates that in the next PCR cycle, the DNA newly synthesized using the about 40 bp primer hybridized to the internal sequence can be bound to forward primer (striped bar), and a homologous strand can be synthesized. FIG. 32d illustrates that this can generate a double stranded CT with the reverse primer sequence about 100 bp closer to the forward primer than occurs naturally in the NT. See, e.g., Chomczynski et al., *Anal. Biochem.* 62, 156-159 (1993); Celi et al., supra, (1993).

Competitive Template Primer Testing

The prepared CT may be tested. For example, the CT primer can be paired with the designed forward primed and used to amplify CT from native cDNA. Before each competitive template in this example was constructed, each primer pair in this example was tested using reverse transcribed RNA from a variety of tissues or individual cDNA clones known to represent the gene of interest as a quality control. For primer pairs that failed (about 10% of the time), new ones were designed and the process repeated. For each gene, a competitive template primer (a fusion oligo of about 40 bp) then was prepared. The 3' end of each fusion primer consisted of an about 20 base sequence homologous to a region about 50 to about 100 bases 3' to the reverse primer. The 5' end was the 20 bp reverse primer.

Competitive Template-Internal Standard Production

For each of a number of genes to be assay, five 10 µL PCR reactions can be set up, using the designed NT forward primer and the CT primer, and amplified for 35 cycles. The products of the five PCR reactions can be combined, electrophoresed on a 3% NuSieve gel in 1×TAE, and the band of correct size cut from the gel and extracted using a QiaQuick method (Qiagen, Valencia, Calif.). The purified PCR products can be cloned into PCR 2.1 vector using TOPO TA cloning kits (Invitrogen, Carlsbad, Calif.) then can be transformed into HS996 (a T 1-phage resistant variant of DH10B). After cloning, transformation, and colonies can be plating on LB plates containing X-Gal, IPTG, and carbenicillin and 3 isolated white colonies selected. Plasmid minipreps can be prepared, EcoRI digestion performed and the digested products electrophoresed on 3% SeaKem agarose. For those clones showing an insert based on EcoRI digestion, it can be confirmed that the insert is the desired one by sequencing the same undigested plasmid preparation using vector specific primers. The clones with homology to the correct gene sequence and having 100% match for the primer sequences can be used in large-scale CT preparation and can be included in standardized mixtures. For example, those that pass this quality control assessment can be used in the following steps.

Plasmids from each quality-assured clone then were prepared in quantities large enough (about 1.5 L) to allow for about 1 billion assays (approximately 2.6 mg). The plasmids were purified from the resultant harvested cells using the Qiagen GigaPrep kit. Plasmid yields were assessed using a Hoeffer DyNAQuant 210 fluorometer.

In this example, an aliquot of each plasmid preparation was again sequenced as a quality control. For each competitive template that passed the quality control steps outlined in this example, the sensitivity of the cloned CT and primers was assessed by performing PCR reactions on serial dilutions and determining the limiting concentration that still yielded a PCR product. In this example, only those preparations and primers that allow for detection of 60 molecules or less (e.g., a product obtained with $10^{-16}$ CT in 10 µl PCR reaction volume) were allowed to be included into standardized competitive template mixtures. In this example, most of the assays that were developed had a sensitivity of about 6 molecules or less (e.g., more than 80% of the CTs that were developed had a sensitivity of 6 molecules or less or $10^{-17}$ M CT).

Preparation of Standardized Mixtures

Plasmids from quality-assured preparations were mixed into competitive template mixtures representing either 24 or 96 genes. The concentration of the competitive templates in the 24 gene standardized mixtures were $4 \times 10^{-9}$ M for β-actin CT, $4 \times 10^{-10}$ M for GAPD (CT1), $4 \times 10^{-11}$ M for GAPD (CT2), and $4 \times 10^{-8}$ M for each of the other CTs in this example.

The 24 gene competitive template mixes can be linearized by NotI digestion prior to preparation of a series of serially-diluted standardized mixtures described below. For example, the mixes can be incubated with NotI enzyme at a concentration of 1 unit/µg of plasmid DNA in about 15 mL of buffer at 37° C. or 12-16 hours. Four linearized 24-gene competitive template mixes were combined in equal amounts to yield 96-gene competitive template mixes having concentrations of $10^{-9}$ M for β-actin, $10^{-10}$ M GAPD (CT1), $10^{-11}$ M GAPD (CT2), and $10^{-8}$ M for the other CTs. These mixes then can be serially diluted with a reference gene CT mix, e.g., comprising the $10^{-9}$ M β-actin, $10^{-10}$ M GAPDH (CT1), $10^{-11}$ M GAPDH (CT2) mix, yielding a stock series at concentrations of $10^{-9}$ M for β-actin, $10^{-10}$ M for GAPD CT1, $10^{-11}$ M for GAPD CT2, and $10^{-8}$, $10^{-9}$, $10^{-10}$, $10^{-11}$, $10\times^{-12}$, and $10^{-13}$ M for the other CTs used in this example.

These stock concentrations can be diluted 1,000-fold to provide working dilutions, e.g., to yield a series of six serially-diluted standardized mixtures (A-F) at concentrations of $10^{-12}$ M for β-actin, $10^{-13}$ M for GAPD CT1, $10^{-14}$ M for GAPD CT2, and $10^{-11}$ (A), $10^{-12}$ (B), $10^{-13}$ (C), $10^{-14}$ (D), $10^{-15}$ (E), and $10^{-16}$ M (F) for the other CTs used in this example.

The following illustrates use of a series of serially-diluted standardized mixtures, in accordance with some embodiments of the instant invention. In this example, "SMIS" refers to a standardized mixture of internal standards, prepared in accordance with embodiments of the instant invention.

A volume of cDNA sample (diluted to a level in balance with the amount of β-actin CT molecules in 1 μL of SMIS ($6\times10^5$) molecules) can be combined and mixed with an equal volume of the appropriate SMIS A-F, such that the NT/CT ratio for a nucleic acid being measured will be greater than about 1/10 and less than about 10/1. For example, if among previous samples, a gene has been expressed within a range of 101-103 molecules/$10^6$ β-actin molecules, the gene will be measured using SMIS E. In contrast, if among previous samples, a gene has been expressed within a range of $10^5$-$10^7$ molecules/$10^6$ β-actin molecules, the gene will be measured using SMIS B. If the appropriate SMIS is not known for a particular gene in a sample from a particular type of tissue, expression can be measured using both SMIS C and E. This allows measurement over four orders of magnitude. For the rare samples that express the gene outside of the expected ranges, a follow-up analysis with the appropriate CT mix can be performed. For example, for the few genes expressed at very high or low level, analysis can be repeated with SMIS A or F.

A 1 μL volume of the cDNA/SMIS mixture can be used for each gene expression assay to be performed and can be combined with other components of the PCR reaction mixture (e.g., buffer, dNTPs, Mg++, Taq polymerase, $H_2O$). Tubes or wells can be prepared with a primer pair for a single gene to be measured. If products are to be analyzed by PE 310 device, the primers can be labeled with appropriate fluor. Aliquots of this PCR reaction mixture can be placed into individual tubes each containing primers for a single gene. Using this approach, the ratio of CT for every gene in the mixture relative to its corresponding NT in the cDNA is fixed simultaneously. When aliquots of this mixture are transferred to PCR reaction vessels, although there may be variations in loading volumes resulting from pipeting, variation is controlled in the NT/CT ratio for any gene relative to the NT/CT ratio for a reference gene. This approach also enables standardized expression measurement.

PCR Amplification

Each reaction mixture can be cycled either in an air thermocycler (e.g., Rapidcycler (Idaho Technology, Inc., Idaho Falls, Id.) or block thermocycler (e.g., PTC-100 block thermal cycler with heated lid, MJ Research, Inc., Incline Village, Nev.) for 35 cycles. In either thermocycler, the denaturation temperature is 94° C., the annealing temperature is 58° C., and the elongation temperature is 72° C.

Separation and Quantification of NT and CT PCR Products a. Agarose gel. Following amplification, the entire volume of PCR product (typically 10 μL) can be into wells of 4% agarose gels (3/1 NuSieve: Sea Kem) containing 0.5 μg/mL ethidium bromide. Gels can be electrophoresed for approx 1 h at 225 V in continuously chilled buffer, and then visualized and quantifying with an image analyzer (products available from Fotodyne, BioRad). Following electrophoresis, the relative amount of NT and CT can be determined by densitometric quantification of bands that have been stained by an intercalating dye (e.g., ethidium bromide).

b. PE Prism 310 Genetic Analyzer CE Device. PCR products can be amplified with fluor-labeled primers. One microliter of each PCR reaction can be combined with 9 μL of formamide and 0.5-0.1 μL of ROX size marker. Samples can be heated to 94° C. for 5 min and flash cooled in an ice slurry. Samples can be loaded onto the machine and electrophoresed at 15 kV, 60° C. for 35-45 min using POP4 polymer and filter set D. The injection parameters can be 15 kV, 5 sec. Fragment analysis software, GeneScan (Applied Biosystems, Inc., Foster City, Calif.) can be used to quantify peak heights that are used to calculate NT/CT ratios. No size correction need be performed where each DNA molecule was tagged with one fluorescent marker from one labeled primer.

c. Agilent 2100 Bioanalyzer Microfluidic CE Device. The DNA 7500 or DNA 1000 LabChip kit may be used. Following amplification, 1 μL of each 10 μL PCR reaction can be loaded into a well of a chip prepared according to protocol supplied by manufacturer. DNA assay can be run, which applies a current to each sample sequentially to separate NT from CT. DNA can be detected by fluorescence of an intercalating dye in the gel-dye matrix. NT/CT ratios can be calculated from area under curve (AUC) and one or more size corrections can be made.

d. Caliper AMS 90 Microfluidic CE Device. The PCR reactions can be set up in wells of a 96- or 384-well microplate. Following amplification, the microplate can be placed in a Caliper AMS 90 and protocol recommended by the manufacturer followed. The AMS 90 can remove and electrophorese a sample from each well sequentially every 30 sec. The NT and CT PCR products can be separated and quantified. Where detection is through fluorescent intercalating dye, size correction need not be necessary.

e. MALDI-TOF separation. A method for separating PCR products recently was described. Ding et al., supra, (2003). This method may be used to quantify products resulting from amplification of cDNA in the presence of SMIS.

Figure 9:
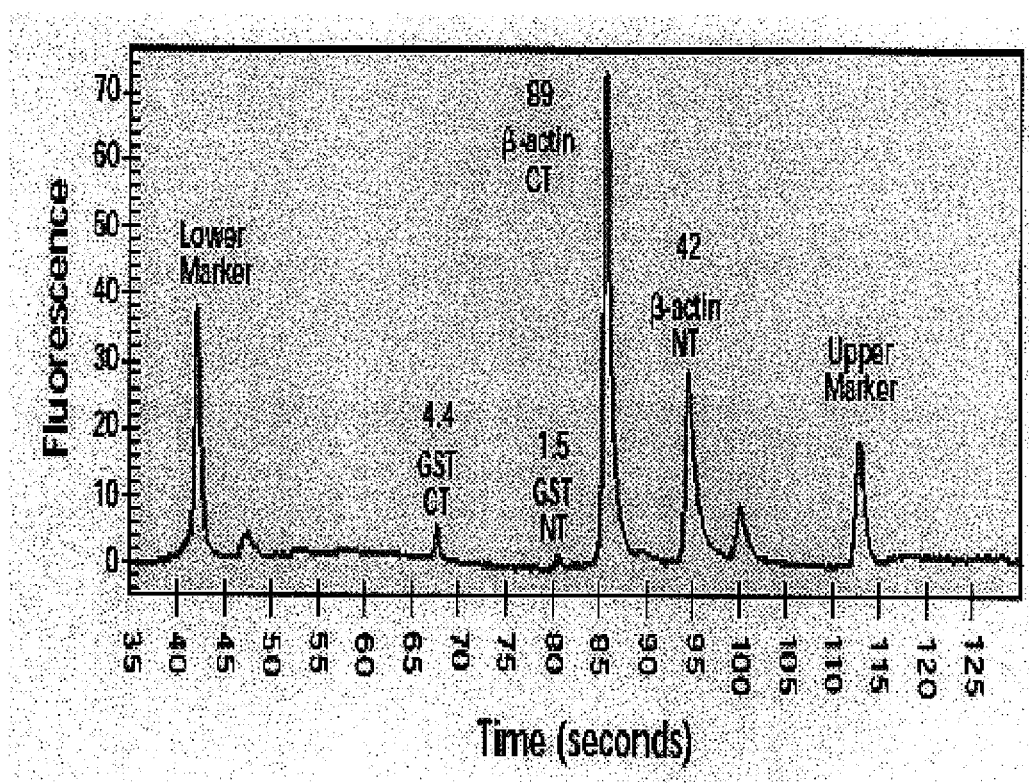
FIG. 9 illustrates a calculation of gene expression based on densitometric values for electrophoretically separated amplified product of GST NT and CT.

Calculation of Gene Expression—Calculating the Number of NT Molecules Present at the Beginning of PCR for Each Gene The steps taken to calculate gene expression can be based on densitometric measurement values for electrophoretically separated NT and CT PCR products such as those presented in FIG. 9. The calculations below are based on the example in FIG. 9, measuring GST gene expression relative to β-actin in an actual bronchial epithelial cell (BEC) sample. A volume of SMIS containing 600,000 competitive template molecules for β-actin and 6000 competitive template molecules for GST was included at the beginning of the PCR reaction. For each gene, the NT and competitive template amplify with the same efficiency. Thus, the β-actin gene NT/CT PCR product ratio allows determination of the number of β-actin NT copies at the beginning of PCR and the target gene NT/CT ratio allows determination of the number of target gene copies of the beginning of PCR, as detailed in the steps below:

1. Correct NT PCR product area under the peak (AUP) to length of CT DNA.
2. Determine ratio of corrected NT AUP relative to CT AUP.
3. Multiply NT/CT value×number of CT molecules at beginning of PCR.

A calculation of β-actin molecules using above protocol is outlined below:

1. 416/532 (β-actin CT bp/NT bp)×42 (NT AUP)=33 (corrected NT value).

2. Correct β-actin NT AUP divided by β-actin CT AUP=0.37.

3. 0.37 (β-actin NT/CT)×600,000 (number of β-actin CT molecules at beginning of PCR)=222,000 NT molecules at beginning of PCR.

A calculation of GST molecules using above protocol is outlined below:

1. 227/359 (GST CT bp/NT bp)×1.5 (NT AUP)=0.95 (corrected NT AUP).

2. 0.95 (GST corrected NT AUP) divided by 4.4 (GST CT AUP)=0.22.

3. 0.22 (GST NT/CT)×6000 (number of GST CT molecules at beginning of PCR)=1290 GST NT molecules at beginning of PCR.

Calculation of molecules of GST/$10^6$ β-actin molecules is 1290 GST NT molecules/222,000 β-actin NT molecules=580 GST molecules/$10^6$ β-actin molecules.

Example III

Blinded Inter-Laboratory Study to Evaluate Reproducibility

In a first study, six laboratories participated in triplicate measurement of five genes in cDNA derived from a bronchogenic carcinoma tissue sample 16009T. A variety of electrophoresis methods and imaging software programs were used in different laboratories to analyze amplified product. Study 1 Laboratory 2 used an Agilent 2100 Bioanalyzer. The intra-laboratory average CV for all gene expression measurements was 0.36, which is comparable to that previously reported (Willey et al, 1998; Rots et al, 1999; Rots et al; 2000; Mollerup et al, 1999; Loitsch et al, 1999). The inter-laboratory variation showed an average CV of 0.71.

In a second study, slab gel electrophoresis and NIH Image software was used to measure expression of 10 genes (the 5 previously measured plus 5 additional genes) in A549 cDNA. Four of the original laboratories were able to participate in the second study. The combined average CV for all nine genes that could be measured was 0.27 and 0.48 for intra-lab and inter-lab comparison, respectively. For TNF alpha, each laboratory determined that the expression was too low to be quantified. Of the four laboratories, three laboratories were able to quantify HNF3α while the fourth lab was not. The lower limit of detection of a PCR product above background was established for the second study as an NIH image arbitrary densitometric value of 5 above background. Although the fourth laboratory observed NT and CT PCR products for HNF3 α, they were below the cut-off level of 5 and therefore not included in the analysis. A CT mix that contributed 60 molecules of nucleic acid CT (F mix) was used to detect HNF3α.

The above detailed description of the present invention is given for explanatory purposes. It will be apparent to those skilled in the art that numerous changes and modifications can be made without departing from the scope of the invention. Accordingly, the whole of the foregoing description is to be construed in an illustrative and not a limitative sense, the scope of the invention being defined solely by the appended claims.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and compositions within the scope of these claims and their equivalents be covered thereby.

All publications, patents, and patent applications mentioned in this specification are herein incorporated by reference to the same extent as if each individual publication, patent or patent application was specifically and individually indicated as being incorporated by reference.

What is claimed is:

1. A method for assaying an analyte in a sample, comprising: allowing said analyte to couple to a first nucleic acid; mixing said analyte with a known amount of an antagonist for said analyte wherein said antagonist is coupled to a competitive template for said first nucleic acid; exposing said mixture to a receptor that can form complexes with both said antagonist and said analyte; amplifying said mixture to obtain an amplified product of said first nucleic acid that complexed with said receptor and a co-amplified product of said competitive template for said first nucleic acid that complexed with said receptor; obtaining a first relation, said first relation comparing amplified product of said first nucleic acid that complexed with said receptor to co-amplified product of said competitive template for said first nucleic acid that complexed with said receptor; mixing a reference nucleic acid in said first sample with a known amount of a competitive template for said reference nucleic acid wherein said reference nucleic acid is a control for loading; obtaining a second relation, said second relation comparing amplified product of said reference nucleic acid to co-amplified product of said competitive template for said reference nucleic acid; and comparing said first and said second relations, thereby assaying said analyte.

2. The method as recited in claim 1 wherein said antagonist comprises said analyte.

3. The method as recited in claim 1 wherein said receptor is immobilized on a substrate.

4. The method as recited in claim 1 wherein said reference nucleic acid comprises a sequence identical to said first nucleic acid.

5. The method as recited in claim 1, further comprising: diluting said co-amplified products of said first nucleic acid and of said competitive template for said first nucleic acid; and further co-amplifying said diluted amplified products.

6. The method as recited in claim 1 wherein said allowing step follows said first mixing and/or said exposing step.

7. The method as recited in claim 1 wherein said receptor is a peptoid.

8. The method as recited in claim 1 wherein said analyte is coupled to said first nucleic acid via a peptoid and/or said antagonist is coupled to said competitive template for said first nucleic acid via a peptoid.

9. The method as recited in claim 1 wherein obtaining said first and said second relations does not involve taking real-time measurements.

10. The method as recited in claim 1 wherein at least one of said amplified products is obtained from beyond an exponential phase of amplification.

11. A method for assessing a first analyte in a sample, comprising: allowing said first analyte to couple to a first nucleic acid; allowing a second analyte in said sample to couple to a second nucleic acid; mixing said first and said second analytes with known amounts of an antagonist for said first analyte coupled to a competitive template for said first nucleic acid and an antagonist for said second analyte coupled to a competitive template for said second nucleic acid; exposing said mixture to a first receptor that can form complexes with said antagonist for said first analyte and with said first analyte and to a second receptor that can form complexes with said antagonist for said second analyte and with said second analyte; amplifying said mixture to obtain an amplified product of said first nucleic acid that complexed with said receptor and a co-amplified product of said competitive template for said first nucleic acid that complexed with said receptor; obtaining a first relation, said first relation comparing amplified product of said first nucleic acid that complexed with said first receptor to co-amplified product of said competitive template for said first nucleic acid that complexed with said first receptor; obtaining a second relation, said second relation comparing amplified product of said second nucleic acid that complexed with said second receptor to co-amplified product of said competitive template for said second nucleic acid that complexed with said second receptor; and comparing said first and said second relations; thereby assessing an amount of said first analyte.

12. The method as recited in claim 11 wherein said second analyte serves as a reference analyte to control for loading.

13. The method as recited in claim 12 wherein said reference analyte is alpha-fetoprotein.

14. The method as recited in claim 11 wherein said known amounts of said antagonists are provided in a standardized mixture.

15. The method as recited in claim 14 wherein said antagonist for said first analyte is at a known concentration relative to said antagonist for said second analyte in said standardized mixture.

16. The method as recited in claim 14 wherein said antagonist for said first analyte is at a series of known concentrations relative to said antagonist for said second analyte in a series of said standardized mixtures.

17. The method as recited in claim 11 wherein said first receptor or said second receptor is immobilized on a substrate.

18. The method as recited in claim 11 wherein at least one of said amplified products is obtained from beyond an exponential phase of said amplification.

19. The method as recited in claim 11 wherein said method can enumerate less than about 100 molecules of said first analyte in said sample.

20. The method as recited in claim 11 wherein said method can enumerate less than about 10 molecules of said first analyte in said sample.

21. The method as recited in claim 11 wherein at least one step is computer implemented.

22. The method as recited in claim 11 wherein said assessed amount is provided as a numerical value that indicates a biological state.

23. The method as recited in claim 11 wherein said assessed amount is used to provide a numerical index that indicates a biological state.

24. A method for assessing an analyte in a sample, comprising: allowing said analyte to couple to a first nucleic acid; mixing said analyte with a known amount of an antagonist for said analyte wherein said antagonist is coupled to a competitive template for said first nucleic acid; exposing said mixture to a receptor that can form complexes with both said antagonist and said analyte; co-amplifying said first nucleic acid that complexed with said receptor and said competitive template for said first nucleic acid that complexed with said receptor; and obtaining a relation wherein said relation is substantially constant beyond an exponential phase of said co-amplification; thereby assessing an amount of said analyte.

25. The method as recited in claim 24 wherein obtaining said substantially constant relation comprises:
  obtaining a first relation, said first relation comparing amplified product of said first nucleic acid that complexed with said receptor to co-amplified product of said competitive template for said first nucleic acid that complexed with said receptor;
  obtaining a second relation, said second relation comparing amplified product of a reference nucleic acid to co-amplified product of a competitive template for said reference nucleic acid; and comparing said first and said second relations.

* * * * *

UNITED STATES PATENT AND TRADEMARK OFFICE
CERTIFICATE OF CORRECTION

PATENT NO.       : 7,476,502 B2
APPLICATION NO.  : 11/103397
DATED            : January 13, 2009
INVENTOR(S)      : James C. Willey It is certified that error appears in the above-identified patent and that said Letters Patent is hereby corrected as shown below:

At column 78, line 39, replace "claim I" with "claim 1".

Signed and Sealed this

Eighteenth Day of August, 2009

David J. Kappos
*Director of the United States Patent and Trademark Office*